(12) United States Patent
Aroian et al.

(10) Patent No.: US 10,940,170 B2
(45) Date of Patent: Mar. 9, 2021

(54) ANTHELMINTIC PROBIOTIC COMPOSITIONS AND METHODS

(71) Applicant: UNIVERSITY OF MASSACHUSETTS, Boston, MA (US)

(72) Inventors: Raffi Van Aroian, Worcester, MA (US); Yan Hu, Shrewsbury, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 659 days.

(21) Appl. No.: 15/321,642

(22) PCT Filed: Jul. 1, 2015

(86) PCT No.: PCT/US2015/038881
§ 371 (c)(1),
(2) Date: Dec. 22, 2016

(87) PCT Pub. No.: WO2016/007355
PCT Pub. Date: Jan. 14, 2016

(65) Prior Publication Data
US 2017/0348362 A1 Dec. 7, 2017

Related U.S. Application Data

(60) Provisional application No. 62/021,576, filed on Jul. 7, 2014.

(51) Int. Cl.
| | | |
|---|---|---|
| *A61K 35/747* | (2015.01) | |
| *A61K 35/742* | (2015.01) | |
| *A61K 35/744* | (2015.01) | |
| *A61K 38/16* | (2006.01) | |
| *A61K 45/06* | (2006.01) | |
| *A61K 31/506* | (2006.01) | |
| *A61K 31/155* | (2006.01) | |
| *A61K 35/00* | (2006.01) | |

(52) U.S. Cl.
CPC .......... *A61K 35/747* (2013.01); *A61K 31/155* (2013.01); *A61K 31/506* (2013.01); *A61K 35/742* (2013.01); *A61K 35/744* (2013.01); *A61K 38/164* (2013.01); *A61K 45/06* (2013.01); *A61K 2035/11* (2013.01)

(58) Field of Classification Search
CPC ............................ A61K 35/747; A61K 31/155
See application file for complete search history.

(56) References Cited

U.S. PATENT DOCUMENTS

| | | | |
|---|---|---|---|
| 4,865,981 A | 9/1989 | Herrnstadt et al. | |
| 5,591,433 A | 1/1997 | Gabriel et al. | |
| 5,596,071 A | 1/1997 | Payne et al. | |
| 7,351,881 B2 | 4/2008 | Carozzi et al. | |
| 7,923,602 B2 | 4/2011 | Carozzi et al. | |
| 2001/0010932 A1* | 8/2001 | Schnepf ................. | A01N 63/10 435/252.33 |
| 2006/0014942 A1 | 1/2006 | Lereclus et al. | |
| 2009/0260107 A1 | 10/2009 | English et al. | |
| 2010/0024075 A1 | 1/2010 | Aroian et al. | |
| 2010/0203521 A1 | 8/2010 | Klapperich et al. | |
| 2011/0263489 A1* | 10/2011 | Aroian ................. | A61K 31/506 514/4.6 |
| 2015/0079203 A1 | 3/2015 | Thomas et al. | |

FOREIGN PATENT DOCUMENTS

| | | | |
|---|---|---|---|
| WO | 2007/062064 A2 | 5/2007 | |
| WO | WO-2007062064 A2 * | 5/2007 | ............. A01N 63/00 |
| WO | 2010/053517 A2 | 5/2010 | |
| WO | WO 2016/007355 A1 | 1/2016 | |
| WO | WO 2016/100128 A1 | 6/2016 | |
| WO | WO 2017/123946 A1 | 7/2017 | |
| WO | WO 2018/217807 A1 | 11/2018 | |

OTHER PUBLICATIONS

Wei, et al. (Bacillus thuringiensis crystal proteins that target nematodes, PNAS 2003, 100:2760-2765) (Year: 2003).*
Battcock (FAO Agricultural Services Bulletin No. 134, 1998) (Year: 1998).*
Hu (Bacillus subtilis Strain Engineered for Treatment of Soil-Transmitted Helminth Diseases, Applied and Environmental Microbiology 2013, 79: 5527-5532, of record Jun. 9, 2017 IDS, in 41) (Year: 2013).*
NCBI Q45712.1, provided in the text (Year: 2019).*
Wei (Bacillus thuringiensis crystal proteins that target nematodes, PNAS 2003, vol. 100) (Year: 2003).*
Ferrer-Miralles (Bacterial cell factories for recombinant protein production; expanding the catalogue, Microbial Cell Factories 2013, 12:113) (Year: 2013).*
Iatsenko (Molecular Mechanisms of Caenorhabditis elegans—Bacillus Interactions, Dissertation, der Eberhard Karls Universität Tübingen, Jun. 23, 2014) (Year: 2014).*

(Continued)

*Primary Examiner* — Lianko G Garyu

(74) *Attorney, Agent, or Firm* — Lathrop GPM LLP; James H. Velema, Esq.

(57) ABSTRACT

Compositions and methods for treating or reducing the severity or likelihood of occurrence of a parasitic worm or helminth infection in a subject are described. The methods include administering to the subject a therapeutically effective amount of a recombinant bacterium expressing a crystal protein such as a *Bacillus thuringiensis* crystal protein (Cry). The crystal proteins may be full length, truncated, variant, or sub-variant Cry proteins. Examples of crystal proteins include Cry5B, Cry21, Cry14A, Cry6A, and Cry13A. The recombinant bacterium may be, for example, a *Bacillus subtilis* or other Gram-positive bacterium, for instance, a lactic acid fermenting bacterium such as *Lactococcus* or *Lactobacillus*. Related compositions and recombinant microorganisms are also described.

29 Claims, 21 Drawing Sheets

Specification includes a Sequence Listing.

(56) References Cited

OTHER PUBLICATIONS

Beveridge (Cellular Responses of Bacillus subtilis and *Escherichia coli* to the Gram Stain, Journal of Bacteriology 1983, 156: 846-858) (Year: 1983).*
Coêlho et al. "Probiotic Therapy: A Promising Strategy for the Control of Canine Hookworm", Journal of Parasitology Research, 2013, 6 pages (Year: 2013).*
Hu et al. "Bacillus thuringiensis Cry5B Protein Is Highly Efficacious as a Single-Dose Therapy against an Intestinal Roundworm Infection in Mice", PLoS Neglected Tropical Diseases, 2011, e614; pp. 1-7 (Year: 2011).*
Bermúdez-Humarán et al. "Lactococci and lactobacillin as mucosal delivery vectors for therapeutic proteins and DNA vaccines", Microbial Cell Factories, 2011, pp. 1-10 (Year: 2011).*
Kho et al. "The Pore-Forming Protein Cry5B Elicits the Pathogenicity of *Bacillus* sp. against Caenorhabditis elegans", PLoS One, 2011, pp. 1-10 (Year: 2011).*
International Search Report of PCT/US2017/013436 dated May 24, 2017, 4 pp.
Durmaz et al., (Dec. 18, 2015), "Intracellular and Extracellular Expression of Bacillus thuringiensis Crystal Protein Cry5B in Lactococcus lactis for Use as an Anthelminthic", Applied and Environmental Microbiology, vol. 82, No. 4, pp. 1286-1294.
Hotez PJ. 2008. Forgotten people, forgotten diseases: the neglected tropical diseases and their impact on global health and development. ASM Press, Washington, DC.
National Research Council. 1996. Guide for the care and use of laboratory animals. National Academies Press, Washington, DC.
Fujiwara RT, Geiger SM, Bethony J, Mendez S. 2006. Comparative immunology of human and animal models of hookworm infection. Parasite Immunol., 28:285-293.
Stepek G, Lowe AE, Buttle DJ, Duce IR, Behnke JM. 2007. Anthelmintic action of plant cysteine proteinases against the rodent stomach nematode, Protospirura muricola, in vitro and in vivo. Parasitology, 134:103-112.
Hu Y, Ellis BL, Yiu YY, Miller MM, Urban JF, Shi LZ, Aroian RV. 2013. An extensive comparison of the effect of anthelmintic classes on diverse nematodes. PLoS One, 8(7):e70702, 12 pages.
Lee AC, Epe C, Simpson KW, Bowman DD. 2011. Utility of capsule endoscopy for evaluating anthelmintic efficacy in fully conscious dogs. Int. J. Parasitol., 41:1377-1383.
Lee AC, Epe C, Bowman DD. 2015. Determination of anthelmintic efficacy against Toxocara canis in dogs by use of capsule endoscopy. Vet. Parasitol., 212:227-231.
Agaisse H, Lereclus D. 1994. Structural and functional analysis of the promoter region involved in full expression of the cryIIIA toxin gene of Bacillus thuringiensis. Mol. Microbiol., 13(1):97-107.
Krings U, Berger RG. 1998. Biotechnological production of 0avours and fragrances. Appl. Microbiol. Biotechnol., 49:1-8.
Chan AC, Ager D, Thompson IP. 2013. Resolving the mechanism of bacterial inhibition by plant secondary metabolites employing a combination of whole-cell biosensor. J. Microbiol. Methods, 9 Pages.
Agaisse H, Lereclus D. 1994. Expression in Bacillus subtilis of the Bacillus thuringiensis cryIIIA toxin gene is not dependent on a sporulation-specific sigma factor and is increased in a spo0A mutant. J. Bacteriol., 176(15):4734-4741.
Urban et al. (2013) "Bacillus thuringiensis-derived Cry5B has potent anthelmintic activity against Ascaris suum," PLoS Negl. Trop. Dis., 7(6):e2263, 7 pages.
Silvaggi, J., et al. Unmasking novel sporulation genes in Bacillus subtillus. J Bacteriol. 186, 8089-8095, 2004.
Sandman, K., et al. Genetic Analysis of Bacillus subtilis spo Mutations Generated by Tn917-Mediated Insertional Mutagenesis. Genetics. 117, 603-617, 1987.
Malvar and Baum, Tn5401 Disruption of the spoOF Gene, Identified by Direct Chromosomal Sequencing, Results in CryIIIIA Overproduction in Bacillus thuringiensis. J Bacteriol. 176, 4750-4753, 1994.

Lereclus D. et al. (1995) "Overproduction of Encapsulation Insecticidal Crystal Proteins in a Bacillus thuringiensis spo0A Mutant," Bio/Technology, 13:67-71.
Xiaohu Shao et al. (2009) "Surface display of heterologous proteins in Bacillus thuringiensis using a peptidoglycan hydrolase anchor," Microbial Cell Factories, 8:48, 17 pages.
Xiang-Qian Li et al. (2008) "Expression of Cry5B protein from Bacillus thuringiensis in plant roots confers resistance to root-knot nematode," Biological Control, 47:97-102.
Rudd A. de Maagd et al. (2001) "How Bacillus thuringiensis has evolved specific toxins to colonize the insect world," Trends in Genetics, 17(4):193-199.
Trang Thi Phuong Phan et al. (2006) "Novel plasmid-based expression vectors for intra- and extracellular production of recombinant proteins in Bacillus subtilis," Protein Expression and Purification, 46:189-195.
Ge et al. (1990) "Hyperexpression of a Bacillus thuringiensis delta-endotoxin gene in *Escherichia coli*: properties of the product," Gene, 93:49-54.
Peng et al. (2003) "A Delta-endotoxin encoded in Pseudomas fluorescens displays a high degree of insecticidal activity," Appl. Microbiol. Biotechnol., 63:300-306.
International Preliminary Report on Patentability with Written Opinion for International Application PCT/US2015/038881, dated Jan. 10, 2017 (22 pages).
Ashikaga et al. (2000) "Natural genetic competence in Bacillus subtilis natto OK2," J Bacteriol. 182(9)2411-5.
Baum et al. (1995) "Regulation of insecticidal crystal protein production in Bacillus thuringiensis," Mol. Microbiol. 18:1-12.
Beasley et al. (2004) "Nisin-producing Lactococcus lactis strains isolated from human milk," Appl Environ Microbiol. 70(8):5051-3.
Berrelli et al. (Nov. 16, 2012) "Interactions between parasites and microbial communities in the human gut," Front Cell Infect Microbiol. 2:141. pp. 1-6.
Bethony et al. (2006) "Soil-transmitted helminth infections: ascariasis, trichuriasis, and hookworm," Lancet 367:1521-1532.
Betz et al. (2000) "Safety and advantages of Bacillus thuringiensis-protected plants to control insect pests," Regul. Toxicol. Pharmacol. 32(2):156-73.
Bischof et al. (2006) "Assays for toxicity studies in C. elegans with Bt crystal proteins," Methods Mol. Biol. 351:139-154.
Braat et al. (2006) "A phase I trial with transgenic bacteria expressing interleukin-10 in Crohn's disease," Clin. Gastroenterol. Hepatol. 4:754-759.
Brans et al. (2004) "New integrative method to generate Bacillus subtilis recombinant strains free of selection markers," Appl. Environ. Microbiol. 70:7241-7250.
Brooker et al. (2008) "Hookworm-related anaemia among pregnant women: a systematic review," PLoS Negl. Trop. Dis. 2:e291. pp. 1-9.
Buasri et al. (Jan. 20, 2012) "Large crystal toxin formation in chromosomally engineered *Bacillus thuringiensis* subsp. *aizawai* due to σE accumulation," Appl. Environ. Microbiol. 78:1682-1691.
Cannon (1996) "Bacillus thuringiensis use in agriculture: a 30 molecular perspective," Biol. Rep. 71:561-636.
Cappello et al. (2006) "A purified Bacillus thuringiensis crystal protein with therapeutic activity against the hookworm parasite Ancylostoma ceylanicum," Proc. Natl. Acad. Sci. USA. 103:15154-15159.
Casula et al. (2002) "Bacillus probiotics: spore germination in the gastrointestinal tract," Appl. Environ. Microbiol. 68:2344-2352.
Conlan et al. (Apr. 2012) "Soil-transmitted helminthiasis in Laos: a community-wide cross-sectional study of humans and dogs in a mass drug administration environment," Am. J. Trop. Med. Hyg. 86:624-634.
Crickmore et al. (1998) "Revision of the Nomenclature for the Bacillus thuringiensis Pesticidal Crystal Proteins," Microbiology and Molecular Biology Reviews. 62(3):807-813.
Cutting (2011) "Bacillus probiotics," Food Microbiol. 28:214-220.
D'Arienzo et al. (2006) "Bacillus subtilis spores reduce susceptibility to Citrobacter rodentium-mediated enteropathy in a mouse model," Res. Microbiol. 157:891-897.

(56) References Cited

OTHER PUBLICATIONS

Dubnau et al. (1971) "Fate of transforming DNA following uptake by competent Bacillus subtilis. I. Formation and properties of the donor-recipient complex," J. Mol. Biol. 56:209-221.
Duc et al. (2003) "Bacterial spores as vaccine vehicles," Infect. Immun. 71:2810-2818.
Duc et al. (2004) "Characterization of Bacillus probiotics available for human use," Appl. Environ. Microbiol. 70 (4):2161-2171.
El-Bendary (2006) Bacillus thuringiensis and Bacillus sphaericus biopesticides production, J. Basic Microbiol. 46:158-170.
Geary et al. (2010) Unresolved issues in anthelmintic pharmacology for helminthiases of 30 humans, Int. J. Parasitol. 40:1-13.
Geertsma et al. (2007) "High-throughput cloning and expression in recalcitrant bacteria," Nat Methods. 4:705-707.
Genbank Database [Online] (Sep. 23, 2008) "truncated Cry5B [synthetic construct]," Accession No. ACI01644. National Center for Biotechnology Information. Accessible on the Internet at URL: https://www.ncbi.nlm.nih.gov/protein/ACI01644. [Last Accessed May 4, 2017].
Goh et al. (2009) "Development and application of a upp-based counterselective gene replacement system for the study of the S-layer protein SlpX of Lactobacillus acidophilus NCFM," Appl. Environ. Microbiol. 75(10):3093-105.
Griffitts et al. (2001) "Bt toxin resistance from loss of a putative carbohydrate-modifying enzyme," Science. 293 (5531):860-4.
Griffitts et al. (2005) "Glycolipids as receptors for Bacillus thuringiensis crystal toxin," Science. 307:922-925.
Griffitts et al. (2005) "Many roads to resistance: how invertebrates adapt to Bt toxins," Bioessays. 27:614-624.
Hall et al. (2008) "A review and metaanalysis of the impact of intestinal worms on child growth and nutrition," Matern. Child Nutr. 4(Suppl 1):118-236.
Hoa et al. (2000) "Characterization of *Bacillus* species used for oral bacteriotherapy and bacterioprophylaxis of gastrointestinal disorders," Appl. Environ. Microbiol. 66:5241-5247.
Hoa et al. (2001) "Fate and dissemination of Bacillus subtilis spores in a murine model," Appl. Environ. Microbiol. 67:3819-3823.
Hoang et al. (2008) "Recombinant Bacillus subtilis expressing the Clostridium perfringens alpha toxoid is a candidate orally delivered vaccine against necrotic enteritis," Infect. Immun. 76:5257-5265.
Holck et al. (1992) "Cloning, sequencing and expression of the gene encoding the cell-envelope-associated proteinase from *Lactobacillus paracasei* subsp. *paracasei* NCDO 151," J. Gen. Microbiol. 138(7):1353-64.
Holden-Dye et al. (2007) "Anthelmintic drugs," WormBook. 2:1-13.
Hong et al. (2008) "The safety of Bacillus subtilis and Bacillus indicus as food probiotics," J. Appl. Microbiol. 105:510-520.
Hu et al. (2009) "The new anthelmintic tribendimidine is an L-type (levamisole and pyrantel) nicotinic acetylcholine receptor agonist," PLoS Negl. Trop. Dis. 3:e499. pp. 1-9.
Hu et al. (2010) "Bacillus thuringiensis Cry5B protein is highly efficacious as a single-dose therapy against an intestinal roundworm infection in mice," PLoS Negl. Trop. Dis. 4:e614. pp. 1-7.
Hu et al. (2010) "Discovery of a highly synergistic anthelmintic combination that shows mutual hypersusceptibility," Proc. Natl. Acad. Sci. USA. 107:5955-5960.
Hu et al. (2012) "Promise of Bacillus thuringiensis crystal proteins as anthelmintics," In; Parasitic Helminths: Targets, Screens, Drugs and Vaccines. Ed.: Caffery. Wiley-VCH Verlag Gmh & Co. Weinheim, Germany. pp. 267-281.
Hu et al. (Jul. 8, 2013) "Bacillus subtilis strain engineered for treatment of soil-transmitted helminth diseases," Appl. Environ. Microbiol. 79(18):5527-5532.
Hu et al. (Nov. 8, 2012) "Mechanistic and single-dose in vivo therapeutic studies of Cry5B anthelmintic action against hookworms," PLoS Negl. Trop. Dis. 6:e1900. pp. 1-8.
Humphries et al. (2011) "Epidemiology of hookworm infection in Kintampo North Municipality, Ghana: patterns of malaria coinfection, anemia, and albendazole treatment failure," Am. J. Trop. Med. Hyg. 84:792-800.
Keiser et al. (2008) "Efficacy of current drugs against soil-transmitted helminth infections: systematic review and meta-analysis," JAMA 299:1937-48.
Keiser et al. (2010) "The drugs we have and the drugs we need against major helminth infections," Adv. Parasitol. 73:197-230.
Kho et al. (2011) "The pore-forming protein Cry5B elicits the pathogenicity of *Bacillus* sp. against Caenorhabditis elegans," PLoS One 6:e29122. pp. 1-9.
Knopp et al. (Apr. 20, 2012) "Nematode infections: soil-transmitted helminths and trichinella," Infect. Dis. Clin. North Am. 26:341-358.
La Ragione et al. (2001) "Bacillus subtilis spores competitively exclude *Escherichia coli* O78:K80 in poultry," Vet. Microbiol. 79:133-142.
La Ragione et al. (2003) "Competitive exclusion by Bacillus subtilis spores of *Salmonella enterica* serotype Enteritidis and Clostridium perfringens in young chickens," Vet. Microbiol. 94:245-256.
Law et al. (1995) "A system to generate chromosomal mutations in Lactococcus lactis which allows fast analysis of targeted genes," J. Bacteriol. 177:7011-7018.
Lereclus et al. (1989) "Transformation and expression of a cloned delta-endotoxin gene in Bacillus thuringiensis," FEMS Microbiol. Lett. 51:211-217.
Li et al. (2008) "Expression of Cry5B protein from Bacillus thuringiensis in plant roots confers resistance to root-knot hematode," Biol. Control. 47(1):97-102.
Los et al. (2011) "RAB-5- and RAB-11-dependent vesicle-trafficking pathways are required for plasma membrane repair after attack by bacterial poreforming toxin," Cell Host Microbe 9:147-157.
Maagd et al. (2001) "How Bacillus thuringiensis has evolved specific toxins to colonize the insect world." Trends in Genetics. 17(4):193-99.
Marroquin et al. (2000) "Bacillus thuringiensis (Bt) toxin susceptibility and isolation of resistance mutants in the hematode Caenorhabditis elegans," Genetics. 155:1693-1699.
McClemens et al. (Jun. 2013) "Lactobacillus rhamnosus Ingestion Promotes Innate Host Defense in an Enteric Parasitic Infection," Clinical and Vaccine Immunology. 20(6):818-826.
Mohamadzadeh et al. (2009) "Dendritic cell targeting of Bacillus anthracis protective antigen expressed by Lactobacillus acidophilus protects mice from lethal challenge," Pproc. Natl. Acad. Sci. USA. 106: 4331-4336.
Moran et al. (2009) G-finder Report: Neglected Disease Research and Development: New Times, New Trends. Global Fund of Innovation for Neglected Diseases.
Norton et al. (1996) "Factors affecting the immunogenicity of tetanus toxin fragment C expressed in Lactococcus lactis," FEMS Immunol. Med. Microbiol. 14:167-177.
Oddone et al. (2009) "Incorporation of nisI-mediated nisin immunity improves vector-based nisin-controlled gene expression in lactic acid bacteria," Plasmid. 61:151-158.
Permpoonpattana et al. (2011) "Immunization with Bacillus spores expressing toxin A peptide repeats protects against infection with Clostridium difficile strains producing toxins A and B," Infect. Immun. 79:2295-2302.
Phan et al. (2006) "Novel plasmid-based expression vectors for intra- and extracellular production of recombinant proteins in Bacillus subtilis," Protein Expr. Purif. 46(2)189-95.
Pusch et al. (2005) "Bioengineering Lactic Acid Bacteria to Secrete the HIV-1 Virucide Cyanovirin," J. Acquir. Immune. Defic. Syndr. 40(5):512-20.
Pusch et al. (2006) "An anti-HIV microbicide engineered in commensal bacteria: secretion of HIV-1 fusion inhibitors by lactobacilli," AIDS. 20:1917-1922.
Roh et al. (2007) "Bacillus thuringiensis as a specific, safe, and effective tool for insect pest control," J. Microbiol. Biotechnol. 17(4):547-59.

(56) References Cited

OTHER PUBLICATIONS

Romero et al. (2006) "Transformation of undomesticated strains of Bacillus subtilis by protoplast electroporation," J. Microbiol. Meth. 66(3):556-9.

Russell et al. (2001) "Identification and cloning of gusA, encoding a new beta-glucuronidase from Lactobacillus gasseri ADH," Appl. Environ. Microbiol. 67(3):1253-61.

Schallmey et al. (2004) "Developments in the use of Bacillus species for industrial production," Can. J. Microbiol. 50:1-17.

Schnepf et al. (1998) "Bacillus thuringiensis and Its Pesticidal Crystal Proteins," Microbiology and Molecular Biology Reviews 62(3):775-806.

Schroeder et al. (2006) "Preventive effects of the probiotic *Escherichia coli* strain Nissle 1917 on acute secretory diarrhea in a pig model of intestinal infection," Dig. Dis. Sci. 51:724-731.

Shao et al. (2009) "Surface display of heterologous proteins in Bacillus thuringiensis using a peptidoglycan hydrolase anchor," Microb. Cell Fact. 8:48. pp. 1-17.

Shevchenko et al. (1996) "Mass spectrometric sequencing of proteins silver-stained polyacrylamide gels," Anal. Chem. 68:850-858.

Shkoporov et al. (2008) "Production of human basic fibroblast growth factor (FGF-2) in Bifidobacterium breve using a series of novel expression/secretion vectors," Biotechnol. Lett. 30:1983-1988.

Sierro et al. (2008) "DBTBS: a database of transcriptional regulation in Bacillus subtilis containing upstream intergenic conservation information," Nucleic Acids Res. 36:D93-D96.

Song et al. (Mar. 22, 2012) "Killed Bacillus subtilis spores as a mucosal adjuvant for an H5N1 vaccine," Vaccine 30:3266-3277.
Soukhathammavong et al. (Jan. 3, 2012) Low efficacy of single-dose albendazole and mebendazole against hookworm and effect on concomitant helminth infection in Lao PDR, PLoS Negl. Trop. Dis. 6(1):e1417. pp. 1-8.
Steidler et al. (2000) "Treatment of murine colitis by Lactococcus lactis secreting interleukin-10," Science. 289:1352-1355.
Steidler et al. (2003) "Biological containment of genetically modified Lactococcus lactis for intestinal delivery of human interleukin 10," Nat. Biotechnol. 21:785-789.
Stothard et al. (2009) "A spot-check of the efficacies of albendazole or levamisole, against soil-transmitted helminthiases in young Ungujan children, reveals low frequencies of cure," Ann. Trop. Med. Parasitol. 103:357-360.
Tchuem Tchuenté (2011) "Control of soil-transmitted 5 helminths in sub-Saharan Africa: diagnosis, drug efficacy concerns and challenges," Acta Trop. 120(Suppl 1):S4-S11.
Tritten et al. (2011) "In vitro and in vivo efficacy of monepantel (AAD 1566) against laboratory models of human intestinal nematode infections," PLoS Negl. Trop. Dis. 5:e1457. pp. 1-7.
Tritten et al. (Dec. 24, 2011) "In vitro and in vivo efficacy of tribendimidine and its metabolites alone and in combination against the hookworms Heligmosomoides bakeri and Ancylostoma ceylanicum," Acta Trop. 122:101-107.
Urban et al. (Jun. 20, 2013) "Bacillus thuringiensis-derived Cry5B has potent anthelmintic activity against Ascaris suum," PLoS Negl Trop Dis. 7(6):e2263. pp. 1-7.
Waeytens et al. (2008) "Paracellular entry of interleukin-10 producing Lactococcus lactis in inflamed intestinal mucosa in mice," Inflamm. Bowel Dis. 14(4):471-9.
Walker et al. (1996) "Electrotransformation of Lactobacillus acidophilus group A1," FEMS Microbiol. Lett. 138 (2-3):233-7.
Wang et al. (Aug. 3, 2012) "Improvement of crystal solubility and increasing toxicity against Caenorhabditis elegans by asparagine substitution in block 3 of Bacillus thuringiensis crystal protein Cry5Ba," Appl. Environ. Microbiol. 78:7197-7204.
Wei et al. (2003) "Bacillus thuringiensis crystal proteins that target nematodes," Proc Natl. Acad. Sci. USA. 100(5):2760-5.
Wells et al. (2008) "Mucosal delivery of therapeutic and prophylactic molecules using lactic acid bacteria," Nat Rev Microbiol. 6(5):349-62.
Yang et al. (1996) "Cloning and expression of full-length delta-endotoxin cryIA(c) gene in three kinds of prokaryotic systems using shuttle vector pHT3101," Wei Sheng Wu Xue Bao. 36:173-180.—English Abstract Only.
Youngman et al. (1984) "Construction of a cloning site near one end of Tn917 into which foreign DNA may be inserted without affecting transposition in Bacillus subtilis or expression of the transposonborne erm gene," Plasmid 12:1-9.
International Search Report with Written Opinion corresponding to International Patent Application No. PCT/US2015/038881, dated Oct. 14, 2015.

* cited by examiner

FIGURE 2
Cry5Ba1

```
   1  MATINELYFV PYNVLAHPIK EVDDPYSWSN LLKGIQEGWE EWGKTGQKKL FEDHLTIAWN
  61  LYKTGKLDYF ALTKASISLI GFIPGAEAAV PFINMFVDFV WPKLFGANTE GKDQQLFNAI
 121  MDAVNKMVDN KFLSYNLSTL NKTIEGLQGN LGLFQNAIQV AICQGSTPER VNFDQNCTPC
 181  NPNQPCKDDL DRVASRFDTA NSQFTQHLPE FKNPWSDENS TQEFKRTSVE LTLPMYTTVA
 241  TLHLLLYEGY IEFMTKWNFH NEQYLNNLKV ELQQLIHSYS ETVRTSFLQF LPTLNNRSKS
 301  SVNAYNRYVR NMTVNCLDIA ATWPTFDTHN YHQGGKLDLT RIILSDTAGP IEEYTTGDKT
 361  SGPEHSNITP NNILDTPSPT YQHSFVSVDS IVYSRKELQQ LDIATYSTNN SNNCHPYGLR
 421  LSYTDGSRYD YGDNQPDFTT SNNNYCHNSY TAPITIVNAR HLYNAKGSLQ NVESLVVSTV
 481  NGGSGSCICD AWINYLRPPQ TSKNESRPDQ KINVLYPITE TVNKGTGGNL GVISAYVPME
 541  LVPENVIGDV NADTKLPLTQ LKGFPFEKYG SEYNNRGISL VREWINGNNA VKLSNSQSVG
 601  IQITNQTKQK YEIRCRYASK GDNNVYFNVD LSENPFRNSI SFGSTESSVV GVQGENGKYI
 661  LKSITTVEIP AGSFYVHITN QGSSDLFLDR IEFVPKIQFQ FCDNNNLHCD CNNPVDTDCT
 721  FCCVCTSLTD CDCNNPRGLD CTLCCQVENQ LPSFVTLTDL QNITTQVNAL VASSEHDTLA
 781  TDVSDYEIEE VVLKVDALSG EVFGKEKKAL RKLVNHTKRL SKARNLLIGG NFDNLDAWYR
 841  GRNVVNVSDH ELFKSDHVLL PPPTLYSSYM FQKVEESKLK ANTRYTVSGF IAHAEDLEIV
 901  VSRYGQEVKK VVQVPYGEAF PLTSRGAICC PPRSTSNGKP ADPHFFSYSI DVGTLDVEAN
 961  PGIELGLRIV ERTGMARVSN LEIREDRPLK KNELRNVQRA ARNWRTAYDQ ERAEVTALIQ
1021  PVLNQINALY ENEDWNGAIR SGVSYHDLEA IVLPTLPKLN HWFMSDMLGE QGSILAQFQE
1081  ALDRAYTQLE ESTILHNGHF TTDAANWTIE GDAHHAILED GRRVLRLPDW SSSVSQTIEI
1141  ENFDPDKEYQ LVFHAQGEGT VSLQHGEEGE YVETHPHKSA NFTTSHRQGV TFETNKVTVE
1201  ITSEDGEFLV DHIALVEAPL PTDDQSSDGN TTSNTNSNTS MNNNQ
```

FIGURE 3
Cry13Aa1

1 MTCQLQAQPL IPYNVLAGVP TSNTGSPIGN AGNQFDQFEQ TVKELKEAWE AFQKNGSFSL
61 AALEKGFDAA IGGGSFDYLG LVQAGLGLVG TLGAAIPGVS VAVPLISMLV GVFWPKGTNN
121 QENLITVIDK EVQRILDEKL SDQLIKKLNA DLNAFTDLVT RLEEVIIDAT FENHKPVLQV
181 SKSNYMKVDS AYFSTGGILT LGMSDFLTDT YSKLTFPLYV LGATMKLSAY HSYIQFGNTW
241 LNKVYDLSSD EGKTMSQALA RAKQHMRQDI AFYTSQALNM FTGNLPSLSS NKYAINDYNV
301 YTRAMVLNGL DIVATWPTLY PDDYSSQIKL EKTRVIFSDM VGQSESRDGS VTIKNIFDNT
361 DSHQHGSIGL NSISYFPDEL QKAQLRMYDY NHKPYCTDCF CWPYGVILNY NKNTFRYGDN
421 DPGLSGDVQL PAPMSVVNAQ TQTAQYTDGE NIWTDTGRSW LCTLRGYCTT NCFPGRGCYN
481 NSTGYGESCN QSLPGQKIHA LYPFTQTNVL GQSGKLGLLA SHIPYDLSPN NTIGDKDTDS
541 TNIVAKGIPV EKGYASSGQK VEIIREWING ANVVQLSPGQ SWGMDFTNST GGQYMVRCRY
601 ASTNDTPIFF NLVYDGGSNP IYNQMTFPAT KETPAHDSVD NKILGIKGIN GNYSLMNVKD
661 SVELPSGKFH VFFTNNGSSA IYLDRLEFVP LDQPAAPTQS TQPINYPITS RLPHRSGEPP
721 AIIWEKSGNV RGNQLTISAQ GVPENSQIYL SVGGDRQILD RSNGFKLVNY SPTYSFTNIQ
781 ASSSNLVDIT SGTITGQVQV SNL

FIGURE 4
Cry14Aa1

```
   1  MDCNLQSQQN IPYNVLAIPV SNVNALVDTA GDLKKAWEEF QKTGSFSLTA LQQGFSASQG
  61  GAFNYLTLLQ SGISLAGSFV PGGTFVAPIV NMVIGWLWPH KNKTADTENL IKLIDEEIQK
 121  QLNKALLDQD RNNWTSFLES IEDTSATVSN AIIDAQWSGT VDTTNRQQKT PTTSDYLNVV
 181  GKFDSADSSI ITNENQIMNG NFDVAAAPYF VIGATLRLSL YQSYIKFCNS WIDAVGFSTN
 241  DANTQKANLA RTKLTMRTTI NEYTQRVMKV FKDSKNMPTI GTNKFSVDAY NVYVKGMTLN
 301  VLDMVAIWSS LYPNDYTSQT AIEQTRVTFS NMVGQEEGTD GTLKIYNTFD SLSYQHSLIP
 361  NNNVNLISYY TDELQNLELA VYTPKGGSGY AYPYGFILNY ANSNYKYGDN DPTGKPLNKQ
 421  DGPIQQINAA TQNSKYLDGE TINGIGASLP GYCTTGCSAT EQPFSCTSTA NSYKASCNPS
 481  DTNQKINALY AFTQTNVKGS TGKLGVLASL VPYDLNPKNV FGELDSDTNN VILKGIPAEK
 541  GYFPNNARPT VVKEWINGAS AVPFYSGNTL FMTATNLTAT QYKIRIRYAN PNSDTQIGVL
 601  ITQNGSQISN SNLTLYSTTD SSMSSNLPQN VYVTGENGNY TLLDLYSTTN VLSTGDITLK
 661  LTGGNQKIFI DRIEFIPTMP VPAPTNNTNN NNGDNGNNNP PHHGCAIAGT QQLCSGPPKF
 721  EQVSDLEKIT TQVYMLFKSS SYEELALKVS SYQINQVALK VMALSDEKFC EEKRLLRKLV
 781  NKANQLLEAR NLLVGGNFET TQNWVLGTNA YINYDSELFN GNYLSLQPAS GFFTSYAYQK
 841  IDESTLKPYT RYKVSGFIGQ SNQVELIISR YGKEIDKILN VPYAGPLPIT ADASITCCAP
 901  EIDQCDGGQS DSHFFNYSID VGALHPELNP GIEIGLKIVQ SNGYITISNL EIIEERPLTE
 961  MEIQAVNRKD QKWKREKLLE CASVSELLQP IINQIDSLFK DANWYNDILP HVTYQTLKNI
1021  IVPDLPKLKH WFIDHLPGEY HEIEQKMKEA LKHAFTQLDE KNLIHNGHFA TNLIDWQVEG
1081  DARMKVLENN ALALQLSNWD SSVSQSIDIL EFDEDKAYKL RVYAQGSGTI QFGNCEDEAI
1141  QFNTNSFVYK EKIIYFDTPS INLHIQSEGS EFVVSSIDLV ELSDDE
```

FIGURE 5A

Cry21Aa1

MTNPTILYPSYHNVLAHPIRLDSFFDPFVETFKDLKGAWEEFGKTGYMDPLKQHLQIAWD
TSQNGTVDYLALTKASISLIGLIPGADAVVPFINMFVDFIFPKLFGRGSQONAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPMLSTNDNTPDFNSDTVLLTLPMYTTGATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVTGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLITSYQVLQMEVTNQTTQKYRIR
IRYATGDTAASIWFHIIGPSGNDLTNEGHNFSSVSSRNKMFVQGNNGKYVLNLITDSIE
LPSGQQTILIQNTNSQDLFLDRIEFISLPSTSTPTSTNFVEPESLEKIINQVNQLFSSSS
QTELAHTVSDYKIDQVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPASDYQHLSAVVVPTLPKQRHWFMEGREGE
HVVLTQQFQQALDRAFQQIEEQNLIHNGNLANGLTDWTVTGDAQLTIFDEDPVLELAHWD
ASISQTIEIMDFEGRHRIQTACTWKRQRNSYRSTWRKRLETMTFNTTSFTTQEQTFYFEG
DTVDVHVQSENNTFLIDSVELIEIIEE

FIGURE 5B
Cry21Aa2
(98% identical to Cry21Aa1)

MTNPTILYPSYHNVLAHPIRLDSFFDPFVETFKDLKGAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPMLSTNDNTPDFNSDTVLLTLPMYTTAATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVAGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLKMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPHVTYQHLSAVVVPTLPKQRHWFMEDREGE
HVVLTQQFQQALDRAFQQIEEQNLIHNGNFANGLTDWTVTGDAQLTIFDEDPVLELAHWD
ASISQTIEIMDFEEDTEYKLRVRGKGKGTVTVQHGEEELETMTFNTTSFTTQEQTFYFEG
DTVDVHVQSENNTFLIDSVELIEIIEE

FIGURE 5C

MIIDSKTTLPRHSLIHTIKLNSNKKYGPGDMTNGNQFIISKQEWATIGAYIQTGLGLPVNEQQLRTHVNL
SQDISIPSDFSQLYDVYCSDKTSAEWWNKNLYPLIIKSANDIASYGFKVAGDPSIKKDGYFKKLQDELDN
IVDNNSDDDAIAKAIKDFKARCGILIKEAKQYEEAAKNIVTSLDQFLHGDQKKLEGVINIQKRLKEVQTA
LNQAHGESSPAHKELLEKVKNLKTTLERTIKAEQDLEKKVEYSFLLGPLLGFVVYEILENTAVQHIKNQI
DEIKKQLDSAQHDLDRDVKIIGMLNSINTDIDNLYSQGQEAIKVFQKLQGIWATIGAQIENLRTTSLQEV
QDSDDADEIQIELEDASDAWLVVAQEARDFTLNAYSTNSRQNLPINVISDSCNCSTTNMTSNQYSNPTTN
MTSNQYMISHEYTSLPNNFMLSRNSNLEYKCPENNFMIYWYNNSDWYNNSDWYNN

TIR, translation initiation region
Usp45, signal secretion peptide of the *L. lactis* secreted protein
D, propeptide DTNSD (representing the first five amino acids of the mature protein)
SPCS, the signal peptidase cleavage site
TT, transcription terminator

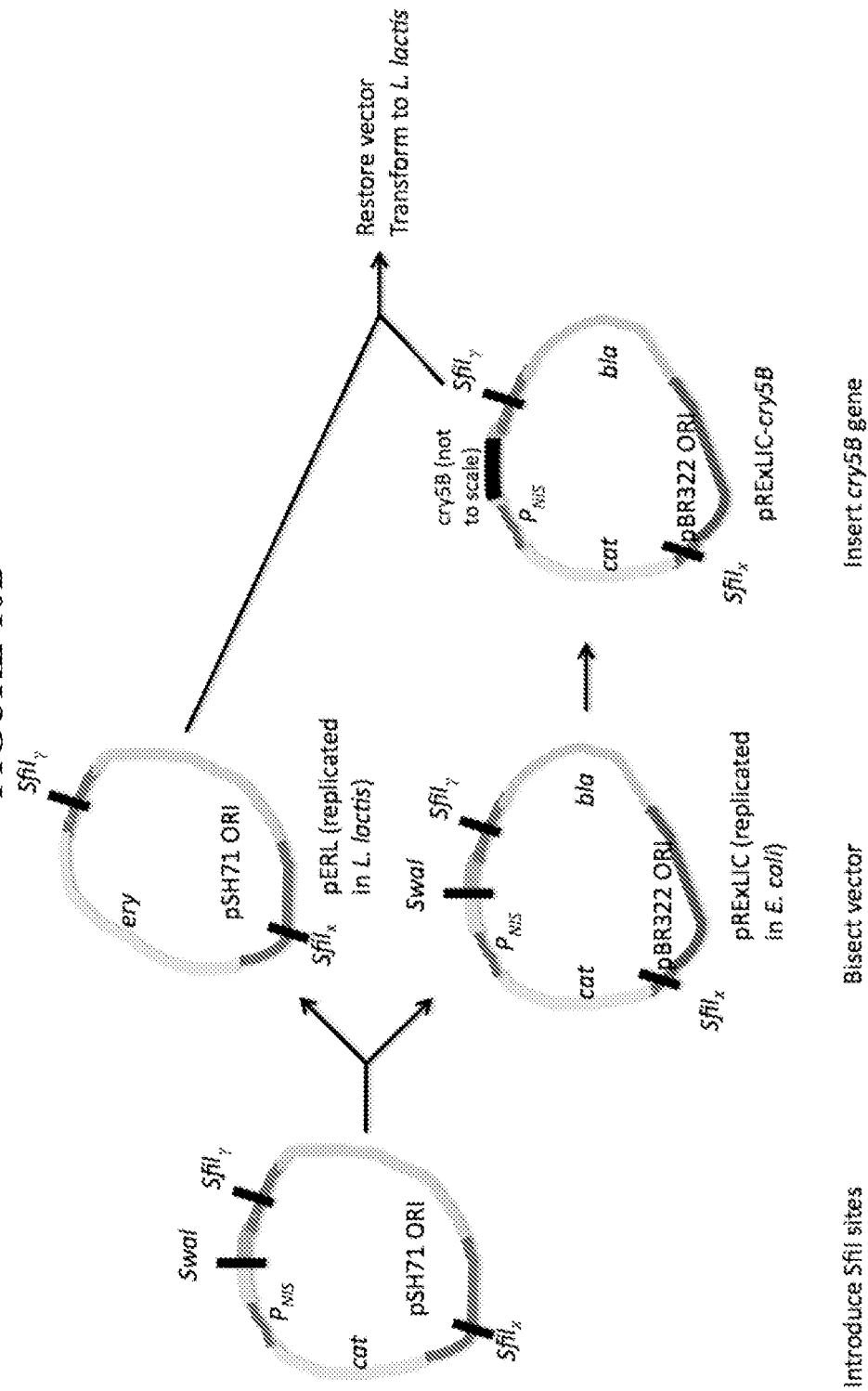

HD1Cry5B SCL

FIGURE 16

PY79 spores/ HD1 Cry5B spores

HD1: 160 x 10^8 CFU/mL
PY79: 120 X 10^8 CFU/mL

Set up a repeat with
L1 control assay

ANTHELMINTIC PROBIOTIC COMPOSITIONS AND METHODS

CROSS REFERENCE TO RELATED APPLICATIONS

This application is a 35 U.S.C. § 371 filing of international application number PCT/US2015/038881, filed Jul. 1, 2015, which claims the benefit under 35 U.S.C. § 119(e) to U.S. Provisional Application No. 62/021,576 filed Jul. 7, 2014, each of which is hereby incorporated by reference in its entirety.

STATEMENT OF GOVERNMENT INTEREST

This invention was made with government support under Grant No. AI056189 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 780093_401WO_SEQUENCE_LISTING.txt. The text file is 50.6 KB, was created on Jun. 30, 2015, and is being submitted electronically via EFS-Web.

BACKGROUND

Technical Field

The presently disclosed invention embodiments relate to delivery by probiotic bacteria of anthelmintic proteins to the lower gastrointestinal (GI) tracts of mammals to treat, reduce the severity of, or reduce the likelihood of occurrence of infection by parasitic soil-transmitted helminthes (STHs).

More specifically, the present disclosure relates to artificial compositions that comprise probiotic bacteria (e.g., *Bacillus subtilis, Lactobacillus, Lactococcus*, and/or others) and heterologous *Bacillus thuringiensis* pesticidal crystal (Cry) proteins, including recombinantly engineered probiotic bacteria that are capable of expressing such heterologous Cry proteins and additionally or alternatively, mixtures of probiotic bacteria with heterologous purified *B. thuringiensis* Cry proteins, that effectively deliver protein anthelmintics to the small and large intestines of mammals to protect against the acquisition, progression, and transmission of STH infections, including gastrointestinal (GI) nematode parasites known as hookworm, whipworm, *Ascaris*, and *Strongyloides*.

Description of the Related Art

Soil-transmitted helminthes (STHs) that parasitize the GI tract of humans infect 2.3 billion of the poorest peoples and 400,000,000 of the poorest children worldwide. (Hall, A., et al. *Matern Child Nutr* 4 Suppl 1, 118-236 (2008)) Infected children can exhibit growth stunting, retarded cognitive development, lethargy, malnutrition, increased school absenteeism, and vulnerability to secondary infections. (Bethony, J. et al. *Lancet* 367, 1521-32 (2006); Hotez, P. J. Forgotten people, Forgotten diseases. (2008)) Pregnant women who are infected are at increased risk for low birth-weight babies and for maternal and infant mortality. (Brooker et al., *PLoS Negl Trop Dis* 2, e291 (2008)). Infected individuals have lower energy, lower productivity, and immune defects that result in increased virulence of HIV/AIDS and a higher likelihood of contracting malaria and tuberculosis (Stothard et al., *Ann Trop Med Parasitol* 103, 357-60 (2009); Moran, M. et al., G-finder Report (2009)); STHs thus trap large populations of the developing world in poverty. The common link of STH transmission is poor sanitation, which requires a massive investment in infrastructure and public health.

Conventional chemotherapy approved by the World Health Organization for STH infections in humans involves treatment with benzimidazoles (e.g., albendazole, mebendazole) or nicontinic acetylcholine receptor (nAChR) agonists (pyrantel, levamisole). (Keiser and Utzinger, *JAMA* 299, 1937-48 (2008)). These compounds, however, lack full efficacy against most human STH parasites. Reports in humans of resistance to both classes of drugs are increasing (e.g., Tanzania, 2010 (Stothard et al., *Ann Trop Med Parasitol* 103, 357-60 (2009)), potentially rendering ineffective current strategies for controlling STH infections. A notable challenge in this field is that the infected populations are among the poorest in the world, and economic incentives to develop new drugs are low (~$700,000/year is spent to develop new drugs against human STHs (Moran, M. et al. G-finder Report (2009)). The poverty of infected populations demands that STH therapeutics be safe, effective, and also inexpensive; highly stable; transportable through distribution routes to infected populations; and amenable to culturally acceptable delivery systems.

Crystal (Cry) proteins made by the soil bacterium *Bacillus thuringiensis* (Bt) may be candidate agents that provide safe and effective treatment of STHs. Cry proteins have been in use for 60+ years as safe, natural, organic insecticides for control of crop pests, mosquitoes, and black flies. (Roh, J. Y., et al. J MICROBIOL BIOTECHNOL 17, 547-59 (2007)). They are also effective against nematodes. (Wei, J. Z. et al. PROC NATL ACAD SCI 100, 2760-5 (2003)). Cry proteins are non-toxic to vertebrates and are EPA approved for expression in transgenic food (e.g., corn, potato). (Mohamadzadeh et al. PNAS 106, 4331-6 (2009); Betz F. S., et al. REGUL TOXICOL PHARMACOL 32, 156-73 (2000)). They are stable and cheap to mass-produce. Activity of Cry proteins against nematode plant parasites and against helminthes has been described, e.g., in WO2007/062064; US2010/0024075; WO2010/053517; and US2011/0263489; see also, e.g., Li, X.-Q. et al., 2008 *Biol. Control* 47:97-102, which describes activity of a Cry5B protein truncated at amino acid residue 698 against *C. elegans* and plant parasitic nematodes.

Two Cry proteins, Cry5B and Cry21A, are highly potent anthelmintics in vivo. (See Cappello, M. et al. *Proc Natl Acad Sci USA* 103, 15154-9 (2006); Hu, Y., et al. PLoS NEGL TROP DIS 4, e614 (2010); and Hu, Y., et al. *Proc Natl Acad Sci USA* 107, 5955-60 (2010)). Cry5B is effective against three intestinal nematodes, *Ancylostoma ceylanicum* hookworms in hamsters, *Heligmosomoides bakeri* in mice, and *Ascaris suum* parasites in pigs, and is 3×-60,0000× more potent than known chemical anthelmintics in a single dose. (See Cappello, M. et al. *Proc Natl Acad Sci* 103, 15154-9 (2006); Hu, Y., et al. *PLoS Negl Trop Dis* 4, e614 (2010); Hu, Y., et al. *PLoS Negl Trop Dis* 6(11), e1900 (2012); and Urban, J., et al *PLoS NEIL TROP DIS* 7(6), e2263 (2013)). Importantly, screens for Cry-resistance mutations in the nematode *Caenorhabditis elegans* indicate that nematodes are 3-20× less likely to develop resistance to Cry proteins than to benzimidazoles or nAChR agoinsts. (Hu, Y., et al. *Proc Natl Acad Sci* 107, 5955-60 (2010)).

Despite the established anthelmintic biological activity of Cry proteins, significant challenges remain with respect to effective delivery of intact, biologically active Cry proteins into the gastrointestinal (GI) tract for treating STHs. These proteins typically have molecular weights of ~135 kDa in their protoxin (unprocessed) forms and ~70 kDa in their active (processed) forms, creating technical difficulties for delivery to the GI lumen via known routes of administration, including problems arising from degradation, poor absorption, clearance mechanisms and other impediments. Clearly there remains a need for new approaches to delivering protein therapeutics such as anthelmintic proteins to the GI tract. The presently disclosed embodiments address this need by providing anthelmintic probiotic compositions and methods, and offer other related advantages.

BRIEF SUMMARY

In certain embodiments of the presently disclosed invention, there are provided methods for delivering crystal proteins to the GI tract of subjects for the treatment of STHs using probiotic bacteria. In particular, Generally Recognized as Safe (GRAS) probiotic lactobacilli and/or *bacillus* strains may be used for delivery of crystal (Cry) proteins (such as one or more *B. thuringiensis* Cry proteins) to the mammalian GI tract. Delivery may be effected by administration to the GI tract of GRAS probiotic bacteria that have been artificially engineered to express one or more heterologous Cry protein(s) before, during, or after administration to the GI tract. Alternatively, GRAS probiotic bacteria that have not been genetically engineered, such as GRAS lactobacilli and/or *bacillus*, may be combined with purified crystal (Cry) proteins from a heterologous source to obtain a mixture that can be administered to the GI tract.

In another embodiment, a method of treating a parasitic worm or helminth infection in a subject is provided. The method includes administering to the subject a therapeutically effective amount of a recombinant bacterium (Gram-positive or Gram-negative) that is capable of expressing a crystal (Cry) protein.

In another embodiment, methods of treating a parasitic worm or helminth infection in a subject are described. The method includes administering to the subject a medicament comprising an amount of a crystal protein-producing genetically modified bacterium (Gram-positive or Gram-negative).

In another embodiment, compositions comprising a non-invasive or non-pathogenic bacterium are described. The non-invasive or non-pathogenic bacterium has a nucleic acid construct or vector having one or more constitutive promoters and coding sequences for the expression of one or more crystal proteins.

In another embodiment, a recombinant microorganism for delivering a crystal protein in vivo is described. The recombinant microorganism includes a coding sequence of the crystal protein under the control of a suitable promoter sequence.

In another embodiment, a probiotic bacterium that is not recombinant is combined with a purified crystal protein and delivered in vivo.

The crystal proteins may be full length, truncated, variants, or subvariants. The truncated crystal protein may include any truncation of the N- and C-termini that still retains toxin activity. The truncated form is not full-length but retains at least 5%, 10%, 20%, 30%, 40%, 50%, 60%, 70%, 80%, or 90% or more of the toxic activity of a corresponding full-length Bt toxin protein. For example, the truncated portion may be truncated between the end of conserved block 5 and the C-terminus of the full length protein.

In one embodiment, the truncated crystal protein may contain the toxin domain of the crystal protein and optionally include up to 5, 10, or 20 additional amino acids. The truncated crystal protein may be truncated after a conserved amino acid sequence of block 5 and optionally include up to 5, 10, or 20 additional amino acids. The conserved amino acid sequence of block 5 may contain the motif DRIEF (SEQ ID NO: 23), DRLEF (SEQ ID NO: 24), or some other related sequence as well as surrounding amino acid residues, e.g., three amino acids upstream and two amino acids downstream of this motif. Table 1 shows the block 5 sequences for various Cry proteins. See e.g., Schnepf, E., et al., *Bacillus thuringiensis* and Its Pesticidal Crystal Proteins, *Microbiology and Molecular Biology Reviews* 62(3): 775-806, (e.g., at p. 781, FIG. 3) (September 1998); and Crickmore et al., Revision of the Nomenclature for the *Bacillus thuringiensis* Pesticidal Crystal Proteins, *Microbiology and Molecular Biology Reviews* 62(3): 807-813 (September 1998). The truncated crystal protein may also be truncated at the N-terminus. For example, the truncated crystal protein may not contain the first about 1, 2, 3, 4, 5, 6, 7, 8, 9, 10, 15, 20, 25, 30, 35, 40, 45, or 50 amino acids at the N-terminus. "Variants" or "subvariants" of Cry proteins include polypeptides with one or more substitutions, e.g., no more than 20 substitutions, alternatively no more than 10 substitutions, or substitutions at 10% or fewer of the residues, relative to a corresponding wild-type polypeptide or truncated version thereof.

Also contemplated according to certain presently disclosed embodiments are Cry protein variants that exhibit at least 50, 55, 60, 65, 70, 75, 80, 85, 86, 87, 88, 89, 90, 91, 92, 93, 94, 95, 96, 97, 98, or 99 percent amino acid sequence identity to a known Cry protein sequence such as any that are disclosed in Crickmore et al., 1998 *Microbiology and Molecular Biology Reviews* 62(3): 807-813, or in Schnepf et al., 1998 *Microbiology and Molecular Biology Reviews* 62(3): 775-806, including full length Cry proteins and truncated Cry proteins, Cry protein variants or subvariants thereof. Also contemplated according to certain embodiments are polynucleotides encoding such Cry proteins and truncations and variants thereof.

TABLE 1

| Protein | Block 5 Conserved Group | |
|---------|------------------------|---|
| Cry1A   | VYIDRIEFVP | (SEQ ID NO: 7) |
| Cry3A   | VYIDKIEFIP | (SEQ ID NO: 8) |
| Cry4A   | VLIDKIEFLP | (SEQ ID NO: 9) |
| Cry5A   | VFLDRIEFIP | (SEQ ID NO: 10) |
| Cry5B   | LFLDRIEFVP | (SEQ ID NO: 11) |
| Cry7A   | FYVDSIEFIP | (SEQ ID NO: 12) |
| Cry8A   | VYIDRIEFIP | (SEQ ID NO: 13) |
| Cry9A   | VYVDRIEFIP | (SEQ ID NO: 14) |
| Cry10A  | IYIDKIEFIP | (SEQ ID NO: 15) |
| Cry12A  | MVLDRIEFVP | (SEQ ID NO: 16) |
| Cry13A  | IYLDRLEFVP | (SEQ ID NO: 17) |

TABLE 1-continued

| Protein | Block 5 Conserved Group | |
|---|---|---|
| Cry14A | IFIDRIEFIP | (SEQ ID NO: 18) |
| Cry19A | LILDKIEFLP | (SEQ ID NO: 19) |
| Cry20A | FVLDKIELIP | (SEQ ID NO: 20) |
| Cry21A | LFLDRIEFIS | (SEQ ID NO: 21) |
| Consensus | i-iDkIEFiP | (SEQ ID NO: 22) |

In Table 1, the consensus sequence denotes the positions at which at least 75% of the aligned proteins in the group have an identical or conserved amino acid sequence. An uppercase letter in the sequence indicates that at least 75% of the residues at that position are identical. A lowercase letter indicates that at least 75% of the residues at that position are conserved. Conserved amino acids fall into the following groups: a (A, G, S, T, or P); d (D, E, N, or Q); f (F, W, or Y)l l(I, L, M, or V), and k (K or R).

The truncated crystal protein may be a truncated form of Cry5B such as *B. thuringiensis* Cry5B (FIG. 2). Truncated Cry5B may extend from about amino acid 1, 2. 3, 4, 5, 6, 7, 8, 9, 10, 15, 20, 25, 30, 35, 40, 45, or 50 to at least about amino acid 693. The truncated form of Cry5B may optionally include up to an additional 5, 10, 20, 30, 40, or 50 amino acids from the C-terminus after conserved block 5, e.g., through about 698, 703, 713, 723, 733, or 743.

The truncated crystal protein may be a truncated form of Cry13A such as *B. thuringiensis* Cry13A (FIG. 3). Truncated Cry13A may extend from about amino acid 1, 2. 3, 4, 5, 6, 7, 8, 9, 10, 15, 20, 25, 30, 35, 40, 45, or 50 to at least about amino acid 688. The truncated form of Cry13A may optionally include up to an additional 5, 10, 20, 30, 40, or 50 amino acids from the C-terminus after conserved block 5, e.g., through about 693, 698, 708, 718, 728, or 738.

The truncated crystal protein may be a truncated form of *B. thuringiensis* Cry14A (FIG. 4). Truncated Cry14A may extend from about amino acid 1, 2. 3, 4, 5, 6, 7, 8, 9, 10, 15, 20, 25, 30, 35, 40, 45, or 50 to at least about amino acid 675. The truncated form of Cry14A may optionally include up to an additional 5, 10, 20, 30, 40, or 50 amino acids from the C-terminus after conserved block 5, e.g., through about 680, 685, 695, 705, 715, or 725.

The truncated crystal protein may be a truncated form of Cry21A such as *B. thuringiensis* Cry21Aa1 (FIG. 5A) or Cry21Aa2 (FIG. 5B). Truncated Cry21A may extend from about amino acid 1, 2. 3, 4, 5, 6, 7, 8, 9, 10, 15, 20, 25, 30, 35, 40, 45, or 50 to at least about amino acid 685. The truncated form of Cry21A may optionally include up to an additional 5, 10, 20, 30, 40, or 50 amino acids from the C-terminus after conserved block 5, e.g., through about 690, 695, 705, 715, 725, or 735.

In certain embodiments of the herein-described methods, compositions, and microorganisms, the bacterium may be a recombinant food-grade bacterium. The bacterium may in certain embodiments be a lactic acid fermenting bacterium, e.g., a member of the *Lactococcus* or *Lactobacillus* species. In certain preferred embodiments the bacterium may be a strain of *Bacillus subtilis*. In certain preferred embodiments the bacterium may be *Bacillus subtilis natto*.

The crystal proteins may in certain embodiments be delivered through in situ synthesis in the subject by the gram-positive bacterium, but the present disclosure is not intended to be so limited and also contemplates, by way of non-limiting example, embodiments in which bacterial synthesis of a Cry protein may have occurred prior to administration of the composition which comprises at least one Cry protein and at least one non-toxic, non-invasive or non-pathogenic bacterium. The Cry protein may in certain embodiments be present within the administered bacterium or exposed on the surface of the administered bacterium or present as a crystalline inclusion produced during stationary phase/sporulation and separate from the bacterium, and may in certain embodiments be secreted by the administered bacterium prior to, during, and/or following administration.

In certain embodiments the Cry protein may be synthesized prior to administration and recovered as an isolated protein or polypeptide, for example, as a spore-crystal lysate or in another form, such that the recovered Cry protein may be admixed with the bacterium prior to simultaneous administration of the Cry protein and the bacterium, or alternatively, such that the Cry protein and the bacterium may be administered sequentially and in either order (i.e., Cry protein followed by bacterium or vice versa). In this context, "isolated" or "purified" may refer to the Cry protein being removed or otherwise physically separated from the intact cell in which it has been synthesized, as is the case for a Cry protein that is present in a spore-crystal lysate as described herein and known in the art. In preferred embodiments the Cry protein is heterologous to the administered bacterium, which refers to any situation in which the Cry protein is not encoded by a polynucleotide sequence that is found naturally in the bacterium.

The recombinant bacterium may also be administered with at least one additional therapeutic agent. The at least one additional therapeutic agent may be a nicotinic acetylcholine receptor agonist. Nicotinic acetylcholine receptor agonists include, but are not limited to, levamisole (or members of the levamisole family), pyrantel, or tribendimidine.

The parasitic worm or helminth infection may be caused by a parasitic worm or helminth that includes but is not limited to Roundworm, Whipworm, Hookworm, *Ascaris*, Pinworm, *Strongyloides, Schistosome*, and *Trematodes*.

The methods may be used to treat mammals including but not limited to humans. Other mammals that can be treated by the methods described herein include but are not limited to feline, rodent, canine, bovine, equine, swine, caprine, ovine, and primate.

Accordingly, in certain embodiments of the presently disclosed invention there is provided a method of treating or reducing severity or likelihood of occurrence of a parasitic worm or helminth infection in a subject, the method comprising administering to the subject a therapeutically effective amount of a composition comprising a recombinant bacterium that has expressed or that is capable of expressing a crystal protein. In certain embodiments the crystal protein is selected from the group consisting of Cry5B, Cry21A, Cry14A, Cry13A, and Cry6A. In certain embodiments the recombinant bacterium is a Gram-positive bacterium and in certain other embodiments the recombinant bacterium is a Gram-negative bacterium. In certain embodiments the recombinant bacterium is a recombinant food grade Gram-positive bacterium. In certain embodiments the recombinant bacterium is a lactic acid fermenting bacterium, which in certain further embodiments is a *Lactococcus* or *Lactobacillus* species, which in certain still further embodiments is *Lactococcus lactis*. In certain embodiments the *Lactobacillus* species is selected from *Lactobacillus acidophilus, Lactobacillus gasseri, Lactobacillus johnsonii*, and *Lactobacillus reuteri*. In certain embodiments the recombinant bacterium is administered in combination with at least one additional therapeutic agent, which in certain embodiments is a nicotinic acetylcholine receptor agonist. In certain embodiments the at least one additional therapeutic agent is administered simultaneously or sequentially (and in either order) with the therapeutically effective amount of the recombinant bacterium expressing the crystal protein. In certain embodiments the nicotinic acetylcholine receptor agonist is from the levamisole family of nicotinic acetylcholine receptor agonists, and in certain embodiments the nicotinic acetylcholine receptor agonist is levamisole. In certain embodiments the levamisole is administered in an amount of about 0.1 mg/kg to about 5.0 mg/kg. In certain embodiments the nicotinic acetylcholine receptor agonist is pyrantel or tribendimidine. In certain embodiments the pyrantel is administered in an amount of about 1.0 mg/kg to about 15.0 mg/kg. In certain embodiments the tribendimidine is administered in an amount of about 0.25 mg/kg to about 10 mg/kg.

In certain embodiments of the present methods the parasitic worm or helminth infection is caused by a parasitic worm or helminth selected from Roundworm, Whipworm, Hookworm, *Ascaris, Pinworm, Strongyloides, Schistosome, and Trematodes*. In certain embodiments the parasitic worm or helminth infection is caused by a parasitic worm or helminth selected from hookworm *Ancylostoma duodenale*, hookworm *Necator americanus*, whipworm *Trichuris trichiura*, roundworm *Ascaris lumbricoides*, threadworm *Strongyloides stercoralis*, and pinworm *Enterobius vermiculari*. In certain embodiments the subject is a human being. In certain embodiments the subject is a mammal selected from feline, rodent, canine, bovine, equine, swine, caprine, ovine, and primate.

In certain embodiments the crystal protein is delivered through in situ synthesis in the subject by the bacterium. In certain embodiments the crystal protein is a truncated crystal protein. In certain embodiments the crystal protein is a variant crystal protein. In certain embodiments the truncated crystal protein is truncated after a conserved amino acid sequence of block 5. In certain embodiments the truncated crystal protein is missing the last 10 amino acids of the C-terminus. In certain embodiments the truncated crystal protein is truncated between the end of conserved block 5 and the C-terminus of the full length protein. In certain embodiments the conserved amino acid sequence of block 5 is DRIEF (SEQ ID NO: 23) or DRLEF (SEQ ID NO: 24). In certain embodiments the truncated crystal protein has toxic activity that is at least 10% or more of the toxic activity of a corresponding full-length protein. In certain embodiments the truncated crystal protein is truncated at the N-terminus. In certain embodiments the truncated crystal protein does not contain the first 5 amino acids of the N-terminus. In certain embodiments the truncated crystal protein is truncated at the C-terminus. In certain embodiments the crystal protein is Cry5B and the Cry5B includes at least amino acids 30 through about 693 of SEQ ID NO:1. In certain embodiments the crystal protein is Cry13A and the Cry13A includes at least amino acids 30 through about 688 of SEQ ID NO:2. In certain embodiments the crystal protein is Cry14A and the Cry14A includes at least amino acids 30 through about 675 of SEQ ID NO:3. In certain embodiments at least one of (a) the crystal protein is Cry21A and the Cry21A includes at least amino acids 30 through about 685 of SEQ ID NO:4, (b) the crystal protein is Cry21A and the Cry21A includes at least amino acids 30 through about 685 of SEQ ID NO:5, or the crystal protein is Cry6A and the Cry6A comprises the amino acid sequence set forth in SEQ ID NO:6 or includes at least amino acids 30 through about 395, 415 or 435 of SEQ ID NO:6.

Turning to another embodiment of the present disclosure there is provided a method of treating or reducing severity or likelihood of occurrence of a parasitic worm or helminth infection in a subject, the method comprising administering to the subject a composition that comprises (a) a therapeutically effective amount of a first recombinant bacterium that has expressed or that is capable of expressing a first crystal protein; and (b) a therapeutically effective amount of a second recombinant bacterium that has expressed or that is capable of expressing a second crystal protein. In certain embodiments the first and second recombinant bacteria are Gram-positive bacteria. In certain embodiments the first and second recombinant bacteria are Gram-negative bacteria. In certain embodiments the first and second recombinant bacteria are administered simultaneously. In certain embodiments the first and second recombinant bacteria are administered sequentially and in either order. In certain embodiments the first and second crystal proteins are different crystal proteins. In certain embodiments the first and second crystal proteins are independently selected from Cry5B, Cry21A, Cry14A, Cry13A, and Cry6A. In certain embodiments the bacterium is a recombinant food grade Gram-positive bacterium. In certain embodiments the bacterium is a lactic acid fermenting bacterium. In certain embodiments the lactic acid fermenting bacterium is a *Lactococcus* or *Lactobacillus* species. In certain embodiments the *Lactoccocus* species is *Lactococcus lactis*. In certain embodiments the *Lactobacillus* species is selected from *Lactobacillus acidophilus, Lactobacillus gasseri, Lactobacillus johnsonii*, and *Lactobacillus reuteri*.

According to certain other embodiments described herein there is provided a method of treating or reducing severity or likelihood of occurrence of a parasitic worm or helminth infection in a subject, the method comprising administering to the subject a medicament comprising a therapeutically effective amount of a bacterium that has been genetically modified to produce a heterologous crystal protein. In certain embodiments the crystal protein-producing genetically modified bacterium is a Gram-positive bacterium. In certain embodiments the crystal protein-producing genetically modified bacterium is a Gram-negative bacterium. In certain embodiments the crystal protein is selected from Cry5B, Cry21A, Cry14A, Cry13A, and Cry6A. In certain embodiments the bacterium is a recombinant food grade Gram-positive bacterium. In certain embodiments the bacterium is a lactic acid fermenting bacterium. In certain embodiments the lactic acid fermenting bacterium is a *Lactococcus* or *Lactobacillus* species. In certain embodiments the *Lactoccocus* species is *Lactococcus lactis*. In certain embodiments the *Lactobacillus* species is *Lactobacillus* selected from *Lactobacillus acidophilus, Lactobacillus gasseri, Lactobacillus johnsonii*, and *Lactobacillus reuteri*. In certain embodiments the crystal protein-producing genetically modified bacterium is administered in combination with at least one additional therapeutic agent, which in a further embodiment is a nicotinic acetylcholine receptor agonist. In certain embodiments the at least one additional therapeutic agent is administered simultaneously with the therapeutically effective amount of the crystal protein-producing genetically modified bacterium. In certain embodiments the at least one additional therapeutic agent is administered sequentially (and in either order) with the therapeutically effective amount of the crystal protein-producing genetically modified bacterium. In certain embodiments the nicotinic acetylcholine receptor agonist is from the levamisole family of nicotinic acetylcholine receptor agonists. In certain embodiments the nicotinic acetylcholine receptor agonist is levamisole. In certain embodiments the levamisole is administered in an amount of about 0.1 mg/kg to about 5.0 mg/kg. In certain embodiments the nicotinic acetylcholine receptor agonist is pyrantel or tribendimidine. In certain embodiments the pyrantel is administered in an amount of about 1.0 mg/kg to about 15.0 mg/kg. In certain embodiments the tribendimidine is administered in an amount of about 0.25 mg/kg to about 10 mg/kg.

In certain related embodiments the parasitic worm or helminth infection is caused by a parasitic worm or helminth selected from Roundworm, Whipworm, Hookworm, *Ascaris*, Pinworm, *Strongyloides, Schistosome*, and *Trematodes*. In certain other related embodiments the parasitic worm or helminth infection is caused by a parasitic worm or helminth selected from hookworm *Ancylostoma duodenale*, hookworm *Necator americanus*, whipworm *Trichuris trichiura*, roundworm *Ascaris lumbricoides*, threadworm *Strongyloides stercoralis*, and pinworm *Enterobius vermiculari*. In certain embodiments the subject is a human being, and in certain embodiments the subject is a mammal selected from feline, rodent, canine, bovine, equine, swine, caprine, ovine, and primate. In certain embodiments the heterologous crystal protein is synthesized by the bacterium in situ in the subject. In certain embodiments the crystal protein is a truncated crystal protein. In certain embodiments the crystal protein is a variant crystal protein. In certain embodiments the truncated crystal protein is truncated after a conserved amino acid sequence of block 5. In certain embodiments the truncated crystal protein is missing the last 10 amino acids of the C-terminus. In certain embodiments the truncated crystal protein is truncated between the end of conserved block 5 and the C-terminus of the full length protein. In certain embodiments the conserved amino acid sequence of block 5 is DRIEF (SEQ ID NO: 23) or DRLEF (SEQ ID NO: 24). In certain embodiments the truncated crystal protein has toxic activity that is at least 10% or more of the toxic activity of a corresponding full-length protein. In certain embodiments the truncated crystal protein is truncated at the N-terminus. In certain embodiments the truncated crystal protein does not contain the first 5 amino acids of the N-terminus. In certain embodiments the truncated crystal protein is truncated at the C-terminus.

In certain embodiments of the methods just described, the crystal protein is Cry5B and the Cry5B includes at least amino acids 1 through about 693 of SEQ ID NO:1. In certain other embodiments the crystal protein is Cry13A and the Cry13A includes at least amino acids 1 through about 688 of SEQ ID NO:2. In certain embodiments the crystal protein is Cry14A and the Cry14A includes at least amino acids 1 through about 675 of SEQ ID NO:3. In certain embodiments at least one of: (a) the crystal protein is Cry21A and the Cry21A includes at least amino acids 30 through about 685 of SEQ ID NO:4, (b) the crystal protein is Cry21A and the Cry21A includes at least amino acids 30 through about 685 of SEQ ID NO:5, or (c) the crystal protein is Cry6A and the Cry6A comprises the amino acid sequence set forth in SEQ ID NO:6 or includes at least amino acids 30 through about 395, 415 or 435 of SEQ ID NO:6.

Turning to certain other embodiments of the present invention there is provided a composition comprising a non-invasive or non-pathogenic bacterium having a nucleic acid construct or vector comprising one or more constitutive promoters operably linked to coding sequences for expression of one or more heterologous crystal proteins. In certain embodiments the one or more crystal proteins is selected from Cry5B, Cry21A, Cry14A, Cry13A, and Cry6A. In certain embodiments the one or more crystal proteins is a truncated crystal protein. In certain embodiments the one or more crystal proteins is a variant crystal protein. In certain embodiments the truncated crystal protein is truncated after a conserved amino acid sequence of block 5. In certain embodiments the truncated crystal protein is missing the last 10 amino acids of the C-terminus. In certain embodiments the truncated crystal protein is truncated between the end of conserved block 5 and the C-terminus of the full length protein. In certain embodiments the conserved amino acid sequence of block 5 is DRIEF (SEQ ID NO: 23) or DRLEF (SEQ ID NO: 24). In certain embodiments the truncated crystal protein has toxic activity that is at least 10% or more of the toxic activity of a corresponding full-length protein. In certain embodiments the truncated crystal protein is truncated at the N-terminus. In certain embodiments the truncated crystal protein does not contain the first 5 amino acids of the N-terminus. In certain embodiments the truncated crystal protein is truncated at the C-terminus. In certain embodiments the one or more crystal proteins is Cry5B and the Cry5B includes at least amino acids 1 through about 693 of SEQ ID NO:1. In certain embodiments the one or more crystal proteins is Cry13A and the Cry13A includes at least amino acids 1 through about 688 of SEQ ID NO:2. In certain embodiments the one or more crystal proteins is Cry14A and the Cry14A includes at least amino acids 1 through about 675 of SEQ ID NO:3. In certain embodiments at least one of: (a) the crystal protein is Cry21A and the Cry21A includes at least amino acids 30 through about 685 of SEQ ID NO:4, (b) the crystal protein is Cry21A and the Cry21A includes at least amino acids 30 through about 685 of SEQ ID NO:5, or (c) the crystal protein is Cry6A and the Cry6A comprises the amino acid sequence set forth in SEQ ID NO:6 or includes at least amino acids 30 through about 395, 415 or 435 of SEQ ID NO:6. In certain embodiments the non-invasive or non-pathogenic bacterium is a lactic acid fermenting bacterium. In certain embodiments the lactic acid fermenting bacterium is a *Lactococcus* or *Lactobacillus* species, which in certain further embodiments is *Lactococcus lactis*. In certain embodiments the *Lactobacillus* species is selected from *Lactobacillus acidophilus, Lactobacillus gasseri, Lactobacillus johnsonii*, and *Lactobacillus reuteri*.

In another embodiment of the present invention there is provided a recombinant microorganism for delivering a crystal protein in vivo, wherein said microorganism comprises a coding sequence of the crystal protein under the control of a suitable promoter sequence. In certain embodiments the microorganism is a gram-positive bacterium. In certain embodiments the microorganism is a Gram-negative bacterium. In certain embodiments the bacterium is a food grade bacterium. In certain embodiments the food grade bacterium is a lactic acid fermenting bacterium. In certain embodiments the lactic acid fermenting bacterium is *Lactococcus* or *Lactobacillus*. In certain embodiments the *Lactococcus* is *Lactococcus lactis*. In certain embodiments the *Lactobacillus* species is selected from *Lactobacillus acidophilus, Lactobacillus gasseri, Lactobacillus johnsonii*, and *Lactobacillus reuteri*. In certain embodiments the crystal protein is selected from Cry5B, Cry21A, Cry14A, Cry13A, and Cry6A. In certain embodiments the crystal protein is a truncated crystal protein. In certain embodiments the crystal protein is a variant crystal protein. In certain embodiments the truncated crystal protein is truncated after a conserved amino acid sequence of block 5. In certain embodiments the truncated crystal protein is missing the last 10 amino acids of the C-terminus. In certain embodiments the truncated crystal protein is truncated between the end of conserved block 5 and the C-terminus of the full length protein. In certain embodiments the conserved amino acid sequence of block 5 is DRIEF (SEQ ID NO: 23) or DRLEF (SEQ ID NO: 24). In certain embodiments the truncated crystal protein has toxic activity that is at least 10% or more of the toxic activity of a corresponding full-length protein. In certain embodiments the truncated crystal protein is truncated at the N-terminus. In certain embodiments the truncated crystal protein does not contain the first 5 amino acids of the N-terminus. In certain embodiments the truncated crystal protein is truncated at the C-terminus. In certain embodiments the crystal protein is Cry5B and the Cry5B includes at least amino acids 30 through about 693 of SEQ ID NO:1. In certain embodiments the crystal protein is Cry13A and the Cry13A includes at least amino acids 30 through about 688 of SEQ ID NO:2. In certain embodiments the crystal protein is Cry14A and the Cry14A includes at least amino acids 30 through about 675 of SEQ ID NO:3. In certain embodiments at least one of (a) the crystal protein is Cry21A and the Cry21A includes at least amino acids 30 through about 685 of SEQ ID NO:4, (b) the crystal protein is Cry21A and wherein the Cry21A includes at least amino acids 30 through about 685 of SEQ ID NO:5, or (c) the crystal protein is Cry6A and wherein the Cry6A comprises the amino acid sequence set forth in SEQ ID NO:6 or includes at least amino acids 30 through about 395, 415 or 435 of SEQ ID NO:6.

According to certain embodiments of the herein described invention there is provided a method wherein the bacterium is selected from *B. subtilis, B. subtilis* PY79, *B. subtilis natto, B. cereus, B. cereus* var. *Toyoi* (*Toyocerin*), *B. cereus* var. *toyoii*, or *B. toyonensis, Lactobacillus rhamnosus, Lactobacillus casei*, and *Lactococcus lactis*. According to certain herein described embodiments there is provided a method wherein first and second recombinant bacteria are administered and each of the first and second recombinant bacterium is independently selected from *B. subtilis, B. subtilis* PY79, *B. subtilis natto, B. cereus, B. cereus* var. *Toyoi* (*Toyocerin*), *B. cereus* var. *toyoii*, or *B. toyonensis, Lactobacillus rhamnosus, Lactobacillus casei*, and *Lactococcus lactis*.

In certain embodiments there is provided a composition as described herein which comprises a non-invasive or non-pathogenic bacterium wherein the non-invasive or non-pathogenic bacterium is selected from *B. subtilis, B. subtilis* PY79, *B. subtilis natto, B. cereus, B. cereus* var. *Toyoi* (*Toyocerin*), *B. cereus* var. *toyoii*, or *B. toyonensis, Lactobacillus rhamnosus, Lactobacillus casei*, and *Lactococcus lactis*. In certain embodiments there is provided a recombinant microorganism as described herein which is selected from *B. subtilis, B. subtilis* PY79, *B. subtilis natto, B. cereus, B. cereus* var. *Toyoi* (*Toyocerin*), *B. cereus* var. *toyoii*, or *B. toyonensis, Lactobacillus rhamnosus, Lactobacillus casei*, and *Lactococcus lactis*.

According to certain other herein disclosed embodiments there is provided an artificial probiotic composition, comprising (a) an isolated polypeptide having at least 50, 55, 60, 65, 70, 75, 80, 85, 86, 87, 88, 89, 90, 91, 92, 93, 94, 95, 96, 97, 98, 99, or 100 percent amino acid sequence identity to a *Bacillus thuringiensis* crystal protein that is selected from Cry5B comprising the amino acid sequence set forth in SEQ ID NO:1, Cry21A comprising the amino acid sequence set forth in SEQ ID NO:4 or SEQ ID NO:5, Cry14A comprising the amino acid sequence set forth in SEQ ID NO:3, Cry13A comprising the amino acid sequence set forth in SEQ ID NO:2, and Cry6A comprising the amino acid sequence set forth in SEQ ID NO:6; and (b) a non-invasive, non-pathogenic probiotic bacterium that is capable of remaining viable in a mammalian gastrointestinal tract following passage through a mammalian stomach and into mammalian small intestine, the probiotic bacterium being selected from *Bacillus subtilis, Lactobacillus* and *Lactococcus*. In certain embodiments the *Bacillus subtilis* is *B. subtilis, B. subtilis* PY79, *B. subtilis natto, B. cereus, B. cereus* var. *Toyoi* (*Toyocerin*), *B. cereus* var. *toyoii*, or *B. toyonensis*, (ii) the *Lactobacillus* is *Lactobacillus rhamnosus* or *Lactobacillus casei*, and (iii) the *Lactococcus* is *Lactococcus lactis*. According to certain presently disclosed embodiments there is provided an artificial probiotic composition, comprising (a) an isolated polypeptide that is selected from a *Bacillus thuringiensis* Cry5B protein and a *Bacillus thuringiensis* Cry14A protein; and (b) a non-invasive, non-pathogenic probiotic bacterium that is capable of remaining viable in a mammalian gastrointestinal tract following passage through a mammalian stomach and into mammalian small intestine, the probiotic bacterium being selected from *Bacillus subtilis, B. subtilis* PY79, *B. subtilis natto, B. cereus, B. cereus* var. *Toyoi* (*Toyocerin*), *B. cereus* var. *toyoii*, and *B. toyonensis*. In certain further embodiments the isolated polypeptide is heterologous to and admixed with the probiotic bacterium.

In another embodiment there is presently provided a method of treating or reducing severity or likelihood of occurrence of a parasitic worm or helminth infection in a gastrointestinal tract of a mammalian subject, the method comprising administering to the gastrointestinal tract of the subject a therapeutically effective amount of an artificial probiotic composition comprising (a) an isolated polypeptide having at least 50, 55, 60, 65, 70, 75, 80, 85, 86, 87, 88, 89, 90, 91, 92, 93, 94, 95, 96, 97, 98, 99, or 100 percent amino acid sequence identity to a *Bacillus thuringiensis* crystal protein that is selected from Cry5B comprising the amino acid sequence set forth in SEQ ID NO:1, Cry21A comprising the amino acid sequence set forth in SEQ ID NO:4 or SEQ ID NO:5, Cry14A comprising the amino acid sequence set forth in SEQ ID NO:3, Cry13A comprising the amino acid sequence set forth in SEQ ID NO:2, and Cry6A comprising the amino acid sequence set forth in SEQ ID NO:6; and (b) a non-invasive, non-pathogenic probiotic bacterium that is capable of remaining viable in the gastrointestinal tract following passage through a mammalian stomach and into mammalian small intestine, the probiotic bacterium being selected from *Bacillus subtilis, Lactobacillus* and *Lactococcus*. In certain further embodiments (i) the *Bacillus subtilis* is *B. subtilis, B. subtilis* PY79, *B. subtilis natto, B. cereus, B. cereus* var. *Toyoi* (*Toyocerin*), *B. cereus* var. *toyoii*, or *B. toyonensis*, (ii) the *Lactobacillus* is *Lactobacillus rhamnosus* or *Lactobacillus casei*, and (iii) the *Lactococcus* is *Lactococcus lactis*. In certain embodiments the artificial probiotic composition comprises (a) an isolated polypeptide that is selected from a *Bacillus thuringiensis* Cry5B protein and a *Bacillus thuringiensis* Cry14A protein; and (b) a non-invasive, non-pathogenic probiotic bacterium that is capable of remaining viable in the mammalian gastrointestinal tract following passage through a mammalian stomach and into mammalian small intestine, the probiotic bacterium being selected from *Bacillus subtilis, B. subtilis natto, B. cereus, B. cereus* var. *Toyoi* (*Toyocerin*), *B. cereus* var. *toyoii*, and *B. toyonensis*. In certain embodiments the isolated polypeptide is heterologous to the probiotic bacterium and is admixed with the probiotic bacterium prior to the step of administering.

In certain embodiments there is provided a method of treating or reducing severity or likelihood of occurrence of a parasitic worm or helminth infection in a gastrointestinal tract of a mammalian subject, the method comprising administering to the gastrointestinal tract of the subject a therapeutically effective amount of an artificial probiotic composition comprising (a) an isolated *Bacillus thuringiensis* Cry5B protein; and (b) *Bacillus subtilis* natto probiotic bacteria, wherein the isolated Cry5B protein is heterologous to the probiotic bacteria and is admixed with the probiotic bacteria prior to the step of administering. In a further embodiment, the isolated *Bacillus thuringiensis* Cry5B protein comprises a polypeptide having at least 50, 55, 60, 65, 70, 75, 80, 85, 86, 87, 88, 89, 90, 91, 92, 93, 94, 95, 96, 97, 98, 99, or 100 percent amino acid sequence identity to the amino acid sequence set forth in SEQ ID NO:1.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE SEVERAL VIEWS OF THE DRAWINGS

FIG. 1 (FIGS. 1A-16).

FIG. 2 illustrates the amino acid sequence of Cry5Ba1 [SEQ ID NO:1].

FIG. 3 illustrates the amino acid sequence of Cry13Aa1 [SEQ ID NO:2].

FIG. 4 illustrates the amino acid sequence of Cry14Aa1 [SEQ ID NO:3].

FIG. 5 (FIGS. 5A-5C). FIG. 5A illustrates the amino acid sequence of Cry21Aa1 [SEQ ID NO:4]. FIG. 5B illustrates the amino acid sequence of Cry21Aa2 (98% identical to Cry21Aa1) [SEQ ID NO:5]. FIG. 5C illustrates the amino acid sequence of Cry6A [SEQ ID NO:6].

FIG. 16 shows data obtained in vitro using the *C. elegans* mortality assay described in FIG. 11 to evaluate the effects on *C. elegans* of purified Cry5B protein (prepared according to Griffitts et al., 2001 *Science* 293:860; for sequence see FIG. 2) when combined in a mixture either with sporulated *B. thuringiensis* HD1 or with sporulated *B. subtilis* PY79. For each data point, the number of spores (HD1 or PY79) was held constant and the quantity of Cry5B was titrated (x-axis).

DETAILED DESCRIPTION

Figure 1A:
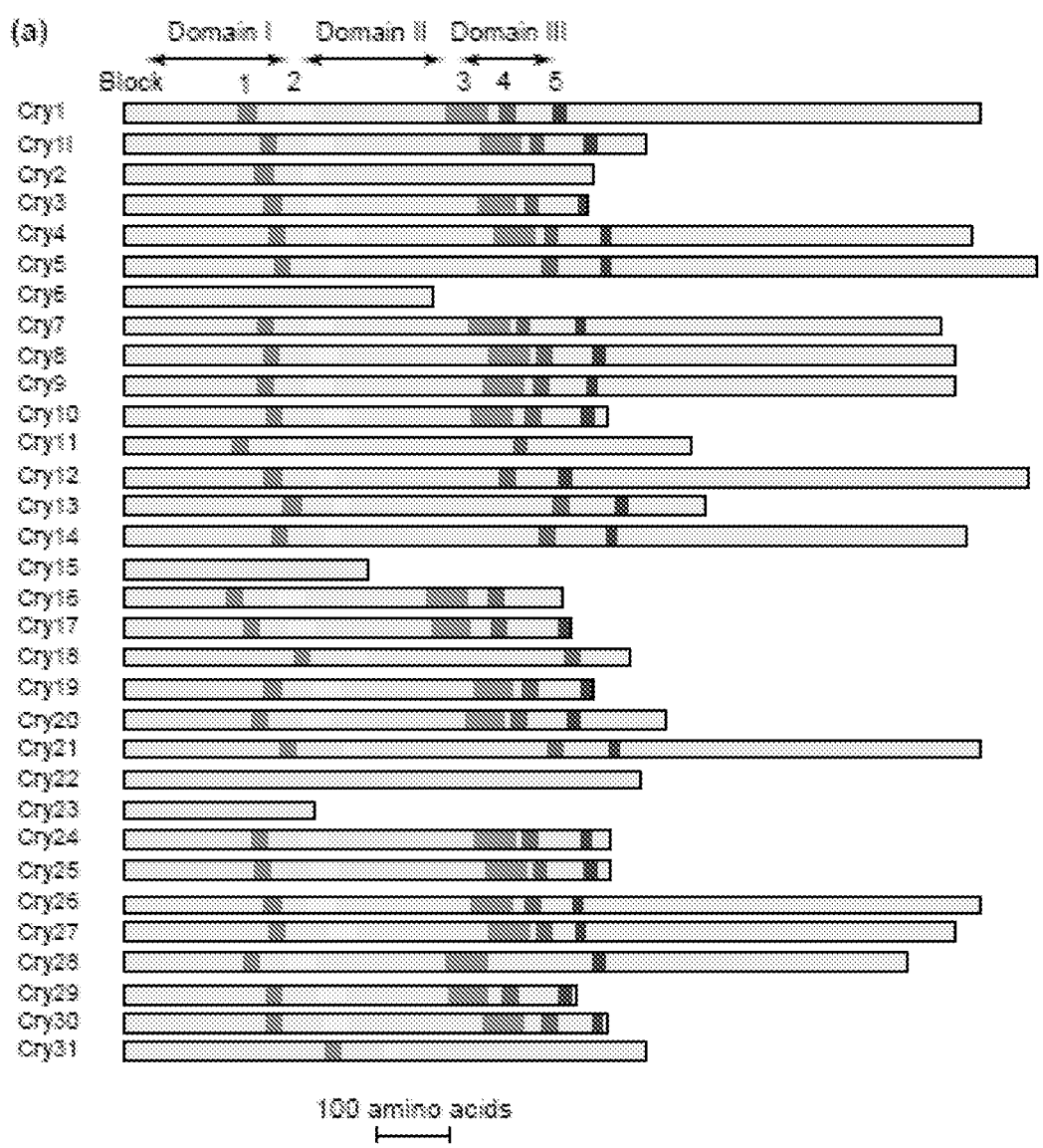
FIG. 1A illustrates the positions of conserved blocks among certain Cry proteins. de Maagd, R. A., et al. "How *Bacillus thuringiensis* has evolved specific toxins to colonize the insect world." TRENDS in Genetics 17(4): 193-99, 195 (FIG. 2*a*) (April 2001).

Certain presently disclosed embodiments relate to unprecedented advantages, described herein for the first time, that are provided by administering to the gastrointestinal (GI) tract of a mammalian subject a Cry protein as described herein and a probiotic bacterium as also described herein, to achieve unexpectedly potent anthelmintic effects against soil-transmitted helminths (STHs). The presently provided compositions and methods will thus find a wide variety of uses, such as for treating or reducing the severity or likelihood of occurrence of STH infections. Despite recognized anthelmintic properties of bacterial Cry proteins, effective therapeutic delivery of such proteins to GI sites of STH infection and parasite residence has not previously been achieved, where in vivo degradation and poor absorptive properties have heretofore precluded useful exploitation of Cry protein anthelmintic effects.

As described herein, orally administering the combination of a bacterial Cry protein with a non-pathogenic, non-toxic, non-invasive bacterium such as a probiotic bacterium surprisingly provides delivery of effective anthelmintic activity to the lower GI tract, where STH parasites reside. Artificial probiotic microbes that are engineered to express heterologous Cry proteins are thus hereby contemplated for anthelmintic therapy according to certain embodiments, which may include oral delivery of one or more of live engineered probiotic bacteria, killed bacteria, and/or bacterial spore-crystal lysates, optionally in further combination with purified Cry proteins and/or other therapeutic agents such as nicotinic acetylcholine receptor agonists or benzimidazole anthelmintic agents. In certain embodiments, unexpectedly superior anthelmintic potency may be achieved by administering the combination of sporulated probiotic bacteria and a heterologous Cry protein. Accordingly, certain herein disclosed embodiments relate to unexpectedly advantageous anthelmintic activity of orally administered artificial probiotic bacteria that have been engineered to express heterologous Cry proteins, and certain other herein disclosed embodiments relate to surprisingly potent anthelmintic effects that reside in a composition which comprises a mixture of certain unmodified probiotic bacteria (e.g., in preferred embodiments *Bacillus subtilis* natto or *Bacillus subtilis* PY79) with isolated heterologous Cry proteins (e.g., Cry5A, Cry14A, etc.).

Probiotic microbes, for example by way of illustration and not limitation, *Bacillus subtilis* (e. g., *Bacillus subtilis* natto, *Bacillus subtilis* PY79, or other strains described herein and known in the art) and *Lactobacillus*, are present in the human gastrointestinal tract at densities of up to $10^8$/gram (Wells and Mercenier, NAT REV MICROBIOL 6:349-362 (2008)). *Bacillus subtilis* has been extensively characterized as a safely ingested food additive in humans (see Example 14, infra, references 15-27). Braat et al., (2006) CLIN GASTROENTEROL HEPATOL 4:754-759 gave human patients orally $10^{10}$ *Lactococcus lactis* twice daily for 7 days as part of a phase I clinical trial. Mice can be given orally $2 \times 10^9$ *Lactococcus lactis* (Waeytens et al., INFLAMM BOWL DIS 14:471-479 (2008)). Therefore, these bacteria can be ingested safely at relatively large concentrations.

These *Lactobacillus* species are human commensal bacteria that naturally reside in the human mouth, intestine, and vagina. *Bacillus subtilis* and *Lactobacillus* are acid tolerant and bile resistant and therefore survive passage through the stomach and remain viable in the small intestine, where the Cry protein can be expressed and secreted to the intestinal mucosa. Thus, production of a *Bacillus subtilis* or *Lactobacillus* or other probiotic bacterial strain capable of expression and secretion of Cry proteins in the small and large intestines will according to certain herein disclosed embodiments provide a valuable delivery vehicle for Cry proteins. Lactobacilli or *Bacillus subtilis* genetically engineered to express Cry proteins can be propagated easily to high concentrations, isolated, lyophilized and stored indefinitely. These production technologies are widely used worldwide to produce "dried" starter cultures for food fermentations (e.g., dried baker's yeast). Furthermore, certain probiotic bacteria such as *Lactobacillus rhamnosus* and *Lactobacillus casei* have been shown to reduce the burden of intestinal helminthes (McClemens, J., et al *Clinical and Vaccine Immunology* 20(6) p. 818-826 (2013) and Berrelli, F., et al *Frontiers in Cellular and Infection Microbiology* 2 Article 141 (2012). Thus, as described herein for the first time, these or other Lactobacilli or probiotic bacteria, e.g., *Bacillus subtilis*, maybe combined with a Cry protein to achieve a surprisingly effective and synergistic anthelmintic effect.

A probiotic microbe, e.g., *Lactobacillus* or *Bacillus subtilis* (e.g., *B. subtilis* strain PY79 or *Bacillus subtilis* natto), which is known to survive gastric transit and which can act as a live oral delivery vector, may be used in certain embodiments for delivery of Cry proteins in the GI tract. Cry proteins may be cloned, expressed, and ultimately secreted in active form in the GI tract of the subject after administration. Recombinant probiotic bacteria that can successfully and safely express biotherapeutic proteins in humans for clinical benefit already exist, e.g., for secretion of the anti-inflammatory cytokine IL-10 for treatment of colitis. (Steidler, L. et al. *Science* 289, 1352-1355 (2000); Braat, H. et al. *Clin Gastroenterol Hepatol* 4, 754-759 (2006); and Steidler, L. et al. *Nat Biotechnol* 21, 785-789 (2003)). This study demonstrated the safety and tolerability of orally formulated genetically-modified bacteria in humans and also verified that the bacteria were environmentally contained (did not propagate outside the human host). These and other studies indicate that: 1) probiotic bacteria are generally safe; and 2) probiotic bacteria may be genetically modified to synthesize and secrete therapeutic proteins to the mammalian GI tract.

Probiotic bacteria are particularly applicable to the control of STHs because 1) probiotic bacteria can transiently (up to 3 weeks) pass through the small and large intestines, thereby secreting anthelmintics into the region where substantially all the STHs reside, 2) recombinant probiotic bacteria can cheaply express large amounts of Cry proteins prior to administration into the GI tract of a mammalian subject, and Cry proteins so expressed, independent of any Cry proteins that may be secreted by probiotic bacteria in the GI tract, have been shown to have a significant impact on STHs, and 3) studies using purified Cry protein to treat hookworms, whipworms, and *H. bakeri*, all in infected rodents, demonstrated that STHs in the mammalian GI tract can ingest and be killed/intoxicated by Cry proteins.

Probiotic bacterium for use in this invention include but are not limited to *Lactococcus* sp., *Lactobacillus* sp., *Bifidobacterium* sp., *Streptococcus* sp., *Leuconostoc* sp., *Pedicoccus* sp., *Enterococcus* sp. *Bacillus* sp., and *Escherichia* sp. *Lactococcus* sp. includes but is not limited to *L. lactis*. *Lactobacillus* sp. includes but is not limited to *L. casei, L. paracasei, L. acidophilus, L. bulgaricus, L. delbrueckii* subsp. *bulgaricus, L. helveticus, L. plantarum, L. salivarius, L. reuteri, L. gasseri*, and *L. animalis*. *Bifidobacterium* sp. includes but is not limited to *B. animalis, B. bifidum, B. breve, B. infantis*, and *B. longum*. *Streptococcus* sp. includes but is not limited to *S. thermophilus*. *Bacillus* sp. includes but is not limited to *B. subtilis, B. subtilis natto, B. cereus, B. cereus* var. *Toyoi* (*Toyocerin*), *B. cereus* var. *toyoii, B. toyonensis, B. thuringiensis, B. clausii*, and *B. pumilus*. *Escherichia* sp. includes but is not limited to *E. coli*.

Probiotic yeast for use in certain contemplated embodiments of this invention include but are not limited to *Saccharomyces* sp., e.g., *Saccharomyces boulardii*.

Crystal Proteins

One goal according to certain herein disclosed embodiments is expression of anthelmintic Cry proteins (e.g., Crickmore et al., 1998 *Microbiology and Molecular Biology Reviews* 62(3): 807-813; Schnepf et al., 1998 *Microbiology and Molecular Biology Reviews* 62(3): 775-806; including but not limited to the *B. thuringiensis* Cry proteins Cry5B (e.g., SEQ ID NO:1) and its subvariants, Cry13A (e.g., SEQ ID NO:2) and its subvariants, Cry14A (e.g., SEQ ID NO:3) and its subvariants, Cry21A (e.g., SEQ ID NOS:4-5) and its subvariants, and Cry6A and its subvariants (e.g., SEQ ID NO:6)) in probiotic bacterium for delivery into a helminth (e.g., roundworm)-infected vertebrate animal gastrointestinal tract via oral dosing (gavage, drinking, eating, pill, capsule, powder, etc.). The Cry protein may be expressed intracellularly in the bacterium, allowing access to the anthelmintic protein after the bacterium lyses or opens up either due to digestion within the gastrointestinal tract, sporulation of certain bacteria, death of bacteria, ingestion and digestion of bacteria by the parasitic helminths (e.g., roundworms such as hookworms, whipworms, *Ascaris, Strongyloides*, veterinary parasitic roundworms of the intestine), etc. The Cry protein may also be expressed and secreted extracellularly by the probiotic bacterium so that the protein would be deposited directly into the GI tract where it could be accessed and ingested by any helminth (e.g., roundworm) inhabiting the GI tract. The Cry proteins may also be expressed in such a way that they are exposed to the extracellular environment of the bacterium and remain anchored to the cell wall of the probiotic bacterium.

In certain embodiments, a probiotic bacterium as provided herein (which may in certain embodiments be LAB as described herein for certain illustrative purposes but which may in certain other embodiments be another probiotic bacterium such as *Bacillus subtilis* and others) may be introduced that expresses an individual Cry protein or that simultaneously expresses multiple Cry proteins. Additionally or alternatively, in certain embodiments multiple probiotic bacteria may be introduced, each of which expresses either a different individual Cry protein or simultaneously expresses multiple Cry proteins. In these and related embodiments, it is contemplated that the GI tract may be seeded with probiotic bacteria that express either one Cry protein or multiple Cry proteins at the same time. For example, due to the lack of cross-resistance between Cry5B-resistant roundworms and Cry21A-resistant roundworms, simultaneous expression of Cry5B and Cry21A in the gastrointestinal tract may inhibit the development of parasite resistance to the combination therapy.

In certain embodiments, a probiotic bacterium as provided herein (which may in certain embodiments be LAB as described herein for certain illustrative purposes but which may in certain other embodiments be another probiotic bacterium such as *Bacillus subtilis* and others) which has not been genetically modified to express a heterologous Cry protein may be admixed and introduced into a mammalian GI tract along with purified Cry5B protein, e.g., heterologous Cry5B that has been expressed and purified from *Bacillus thuringiensis*. As described herein for the first time, a composition so formed by such admixture exhibited heretofore unpredicted biological activity, in a manner such that the specific probiotic bacterium (e.g., *Bacillus subtilis natto, Bacillus subtilis* PY79) synergized with Cry5B protein to enhance its anthelmintic properties.

In the long run, removing antibiotic selection capability (e.g., genetic selection markers) from the plasmids that are employed to introduce heterologous Cry protein-encoding sequences, as well as using probiotic (e.g., *lactobacillus* or LAB) strains that are unable to replicate outside the vertebrate host, may be desirable in order to environmentally contain the genetically modified bacteria. For example, LAB bacteria have been engineered to be autotrophic in thymidine or thymine synthesis such that they can only grow in the vertebrate intestine where thymidine or thymine is present and not in the environment where thymidine or thymine is not present. See, e.g., Steidler L, et al. "Biological containment of genetically modified *Lactococcus lactis* for intestinal delivery of human interleukin 10." Nat Biotechnol 21: 785-789 (2003).

Cry-transformed probiotic bacteria such as Bacilli or LAB may be cultured and expression of intracellular, membrane-anchored, or secreted Cry protein by such bacteria may be confirmed using antibodies raised against each Cry protein and standard Western blotting or ELISA techniques.

To assess the bioactivity of all constructs, recombinant LAB-expressing Cry protein (full length, truncated, or variants) may be fed to the free-living nematode, *C. elegans*. Cry protein toxicity on *C. elegans* using LC50, brood-size, developmental inhibition assays on solid media and in liquid wells may then be quantitated. *C. elegans* can access the Cry proteins either via protein secreted onto the solid media/into the liquid well or by their ability to grind, open and digest bacteria. Confirmation that the lactobacilli are making bioactive Cry proteins may be obtained. Furthermore, the bioactivity (e.g., $LC_{50}$ in μg/mL) may be quantitated and the constructs giving the highest activity determined.

Truncations, Variants, and Sub-Variants

The crystal proteins may be truncated to enhance their effectiveness. The usefulness of Bt toxins (e.g., crystal proteins) for controlling STHs may be limited by the protein size that STHs can ingest. Some parasitic roundworms poorly ingest proteins larger than about 40 kD. Thus, the effectiveness of any particular Bt toxin may be limited by size exclusion of proteins that STHs take in and so should be small enough to be readily absorbed by the STH gut while retaining toxic activity. There are other compelling reasons to produce a toxin truncated from the full length version. A truncated toxin may be easier to express in probiotic bacteria or yeast. Producing a truncated toxin will also alleviate the requirement that the target STH has the proper proteases present to correctly process full length protoxin (which is inactive) to a truncated, active toxin form. Thus, a truncated toxin will be immediately available for intoxication independent of whether the proper protease processing enzymes are present in the STH target. Truncated toxin may also express at a higher level in probiotic bacteria or yeast because truncated toxins are soluble and less likely to form insoluble inclusions in the cell expressing them, which could be toxic to the cell or which could make the toxin fold incorrectly. Accordingly, it is desirable to produce truncated Bt toxin fragments (e.g., crystal protein fragments). Moreover, fragments of certain Bt toxins have been tested and shown to retain toxic activity and have improved biological properties. By "truncated," when referring to a Bt toxin protein (crystal protein) is meant a Bt toxin protein that is not full-length but retains at least 5%, 10%, 20%, 30%, 40%, 50%, 60%, 70%, 80%, or 90% or more of the toxic activity of a corresponding full-length Bt toxin protein.

"Variants" or "subvariants" of Cry proteins include polypeptides with one or more substitutions, e.g., no more than 20 substitutions, alternatively no more than 10 substitutions, or substitutions at 10% or fewer of the residues, relative to a corresponding wild-type polypeptide or truncated version thereof. The variant, subvariant, or truncated polypeptide has at least 5%, 10%, 20%, 30%, 40%, 50%, 60%, 70%, 80%, or 90% of the activity, e.g., toxic activity, of the corresponding wild-type polypeptide or truncated version. Conservative substitutions include substitutions within the following groups: glycine, alanine, threonine, valine, isoleucine, leucine; aspartic acid, glutamic acid, asparagine, glutamine; serine, cysteine; lysine, arginine; aspartic acid, glutamic acid; serine, threonine; asparagine, glutamine; phenylalanine, tyrosine.

Nucleic acid molecules encoding amino acid sequence variants, truncated versions, or both, of a Cry protein are prepared by a variety of methods known in the art. These methods include, but are not limited to, isolation from a natural source (in the case of naturally occurring amino acid sequence variants) or preparation by, for example, oligonucleotide-mediated (or site-directed) mutagenesis, PCR mutagenesis, and cassette mutagenesis of an earlier prepared variant or a non-variant version of protein. Moreover, the invention includes synthetic nucleic acid molecules where nucleotides are modified to include codons preferred in a particular organism, remove codons rarely used in a particular organism, or remove sequences that may inhibit transcription or RNA processing and the like.

Figure 1B:
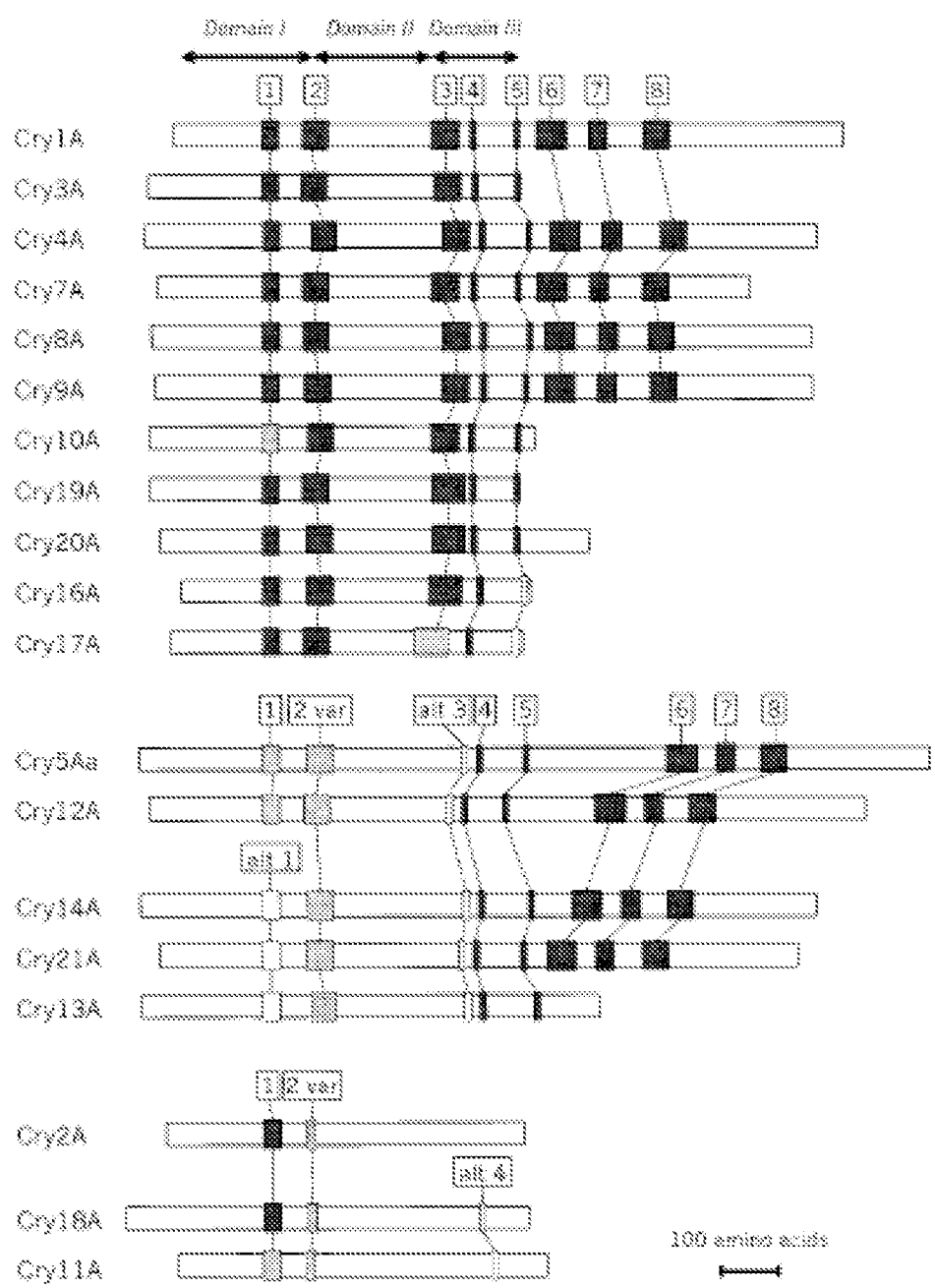
FIG. 1B illustrates the positions of conserved blocks among certain Cry proteins. Schnepf, E., et al. "*Bacillus thuringiensis* and Its Pesticidal Crystal Proteins." Microbiology and Molecular Biology Reviews 62(3): 775-806, 781 (FIG. 3) (September 1998).

Cry protein truncations may at least include conserved blocks 1-5. As seen in FIGS. 1A and 1B, alignment of known Cry toxins reveals five conserved sequence blocks (blocks 1-5) that are common to a majority of the proteins and are thought to be located in the active toxin domain. See de Maagd, R. A., et al. "How *Bacillus thuringiensis* has evolved specific toxins to colonize the insect world." TRENDS IN GENETICS 17(4): 193-99 (April 2001). Comparison of the carboxy-terminal halves of the sequences have suggested the presence of three additional blocks that lie outside of the active toxic core. See Schnepf, E., et al. "*Bacillus thuringiensis* and Its Pesticidal Crystal Proteins." MICROBIOLOGY AND MOLECULAR BIOLOGY REVIEWS 62(3): 775-806 (September 1998). Thus, Cry protein truncations may be truncated after the conserved amino acid sequence of block 5 (e.g., DRIEF (SEQ ID NO: 23) or DRLEF (SEQ ID NO: 24)). Alternatively, Cry protein truncations may be truncated after the conserved amino acid sequence of block 5 (e.g., DRIEF (SEQ ID NO: 23) or DRLEF (SEQ ID NO: 24)) plus an additional about 2, 3, 4, 5, 10, 15, 20, 25, 30, 35, 40, 45, or 50 amino acids of the c-terminal domain.

The complete amino acid sequence of Cry5Ba1 is listed in FIG. 2. The conserved amino acid sequence DRIEF (SEQ ID NO: 23) in Cry5B ends at amino acid number 693. Thus, a truncated form of Cry5B may include at least amino acids 50 through about 693. A truncated form of Cry5B may extend from about amino acid 1, 2. 3, 4, 5, 6, 7, 8, 9, 10, 15, 20, 25, 30, 35, 40, 45, or 50 to at least about amino acid 693. Alternatively or in addition to, a truncated form of Cry5B may include about 5, 10, 15, 20, 25, 30, 35, or 40 additional amino acids of the c-terminal domain.

The complete amino acid sequence of Cry13Aa1 is listed in FIG. 3. The conserved amino acid sequence DRLEF (SEQ ID NO: 24) in Cry13A ends at amino acid number 688. Thus, a truncated form of Cry13A may include at least amino acids 50 through about 688. A truncated form of Cry5B may extend from about amino acid 1, 2. 3, 4, 5, 6, 7, 8, 9, 10, 15, 20, 25, 30, 35, 40, 45, or 50 to at least about amino acid 688. Alternatively or in addition to, a truncated form of Cry13A may include about 5, 10, 15, 20, 25, 30, 35, or 40 additional amino acids of the c-terminal domain.

The complete amino acid sequence of Cry14Aa1 is listed in FIG. 4. The conserved amino acid sequence DRIEF (SEQ ID NO: 23) in Cry14A ends at amino acid number 675. Thus, a truncated form of Cry14A may include at least amino acids 50 through about 675. A truncated form of Cry5B may extend from about amino acid 1, 2. 3, 4, 5, 6, 7, 8, 9, 10, 15, 20, 25, 30, 35, 40, 45, or 50 to at least about amino acid 675. Alternatively or in addition to, a truncated form of Cry14A may include about 5, 10, 15, 20, 25, 30, 35, or 40 additional amino acids of the c-terminal domain.

Figure 5B:
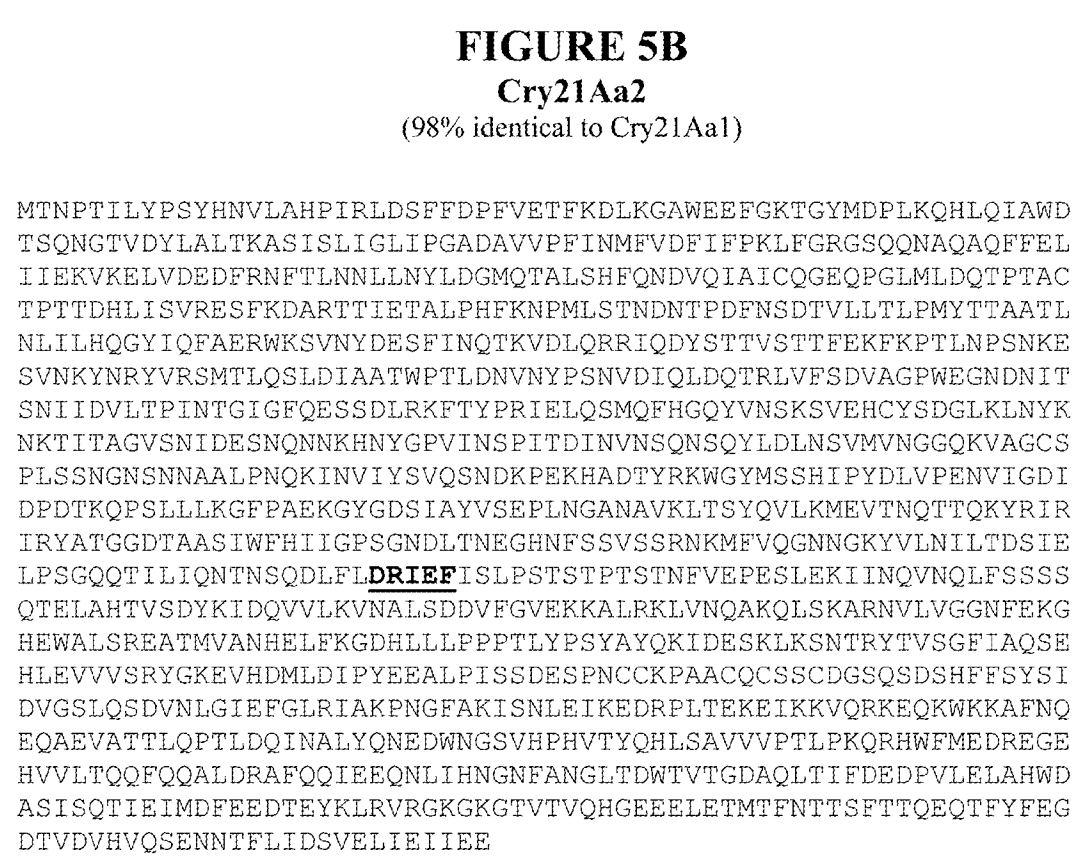

The complete amino acid sequence of Cry21Aa1 and Cry21Aa2 are listed in FIGS. 5A and 5B, respectively. The amino acid sequence of Cry21Aa2 is about 98% identical to the sequence of Cry21Aa1. The conserved amino acid sequence DRIEF (SEQ ID NO: 23) in Cry21A ends at amino acid number 685. Thus, a truncated form of Cry21A may include at least amino acids 50 through about 685. A truncated form of Cry5B may extend from about amino acid 1, 2. 3, 4, 5, 6, 7, 8, 9, 10, 15, 20, 25, 30, 35, 40, 45, or 50 to at least about amino acid 685. Alternatively or in addition to, a truncated form of Cry21A may include about 5, 10, 15, 20, 25, 30, 35, or 40 additional amino acids of the c-terminal domain.

Anthelmintic Experiments

Once heterologous Cry protein expression and bioactivity are confirmed in a desired probiotic bacterium, the modified bacteria may be used for curative-type and preventative-type anthelmintic experiments. By way of non-limiting example, the *Bacillus* or LAB strain expressing heterologous Cry protein may be any of the Bacilli or LAB mentioned above expressing either full length or truncated heterologous Cry protein (e.g., *B. thuringiensis* Cry5B, Cry13A, Cry14A, or Cry21A) with that Cry protein expressed intracellularly, anchored at the membrane, or secreted.

Antibody Production:

Antibodies against recombinant Cry proteins (e.g., Cry5B, Cry21A, Cry14A, Cry13A, and Cry6A, full length and truncated proteins) may be produced and purified according to standard methodologies (e.g., *Current Protocols in Immunology*, John Wiley & Sons, New York, N.Y. (2009).

Bioactivity Tests:

To assess the bioactivity of all constructs, recombinant bacilli or lactobacilli expressing heterologous Cry proteins are fed to the free-living nematode, *C. elegans. C. elegans* can access the Cry proteins either via protein secreted onto the solid media/into the liquid well or by their ability to grind and digest bacteria to open the bacterial cells.

Rodent and Parasite Tests:

Three intestinal parasitic nematodes—*H. bakeri* (small intestine nematode parasite) in mice, and *Trichuris muris* (whipworm) in mice, and *A. ceylanicum* (hookworm) in hamsters are tested. The tests address: 1) where in the GI tract do heterologous Cry-expressing bacilli or lactobacilli reside and for how long; and 2) how do these bacilli or lactobacilli affect the acquisition and progression of intestinal nematode parasites.

*Bacillus, Lactobacillus* or *Lactococcus* Tests:

Mice are gavaged with high doses of heterologous Cry-expressing *Bacillus subtilis, Lactobacillus* or *Lactococcus* ($10^9$ cfu). A portion of the mice are periodically (twice/week up to one month) euthanized. Small and large intestinal homogenates can be prepared after washing intact tissue with Hanks' balanced salt solution twice and after removing the mucous layer and epithelium by 1 mM DTT twice and then 10 mM EDTA. Plating of these homogenates on medium plates, such as GM17 agar supplemented with an antibiotic appropriate to the selectable marker used on the expression system, will select for the bacterium. In addition, immunoblotting of plate colonies, transferred to nitrocellulose membrane, with anti-Crystal protein antibodies will be used to reveal which of the colonies on the plate are Cry-expressing bacteria. From these experiments, the colony forming units from the homogenates can be determined, indicative of how well the Cry-transformed bacteria are able to colonize the gastrointestinal tract over time (For an example, see Waeytens et al., *Inflamm Bowel Dis* 2008: 14:471-479).

Parasite Tests:

Naïve (uninfected mice) are gavaged with the best heterologous Cry-protein expressing *Bacillus, Lactobacillus* or *Lactococcus* strain(s) based on expression and bioactivity. Protect against acquisition test: Control mice receive the native (unmodified) *Bacillus, Lactobacillus* or *Lactococcus* which is incapable of Cry protein expression. A few days later, both groups of mice are then challenged with *H. bakeri*. Two weeks later, intestinal worm burdens and fecal egg counts are used to determine if the probiotics protect the mice against a challenge with infectious parasites. Protest against progression test: Mice are infected with *H. bakeri*. Two weeks later, infected mice are treated with heterologous Cry-protein expressing or control bacilli, lactobacilli, or lactococci, respectively. Intestinal worm burdens and fecal egg counts are used to determine if the probiotics provide anthelmintic therapy in mice with pre-existing nematode infections.

Exemplary Parasites

The present invention relates in certain preferred embodiments to the control of parasitic worms, e.g., nematodes and platyhelminths, using crystal proteins from *Bacillus* and their derivatives. Parasitic worms within the scope of the invention include but are not limited to those in Class Adenophorea, e.g., Order Mononchida, Family Plectidae, and Order Stichosomida, Family Mermithidae and Tetradonematidae; Class Secernentea, e.g., Order Rhabditida, Family Carabonematidae, Cephalobidae, Chambersiellidae, Heterorhabditidae, Oxyuridae, Panagrolaimidae, Rhabditidae, Steinernematidae, Syrphonematidae, Syrphonematidae, or Thelastomatidae; Order Spirurida, Family Filariidae, Onchocercidae, Physalopteridae, Syngamidae, Spiruridae, Subuluridae, or Thelaziidae; Order Diplogasterida, Family Diplogasteridae; and Order Tylenchida, Family Allantonematidae, Aphelenchidae, Aphelenchoididae, Entaphelenchidae, Fergusobiidae, Phaenopsitylenchidae, Sphaerulariidae, Anguinidae, Dolichodoridae, Belonolaimidae, Pratylenchidae, Hoplolamidae, Heteroderidae, Criconematidae, Tylenchulidae or Tylenehidae. In one embodiment, the parasite is from Class Secernentea, Order Ascaridida, Family Ascarididae; Class Adenophorea, Order Trichurida, Family Trichuridae; Class Secernentea, Order Strongylida, Family Ancylostomatidae (ancylostomidae) or Trichostrongylidae; or Class Secernentea, Order Spirurida, Family Dracunculidae, Filariidae, or Onchocercidae.

The parasite may be a helminth. Helminths within the scope of the invention include but are not limited to those from Phylum Annelida, Class Polychaetae, Class Myzostomida, Class Clitellata, Subclass Hirudinea, Order Gnathobdellidae, Order Rhynchobdellidae; Phylum Platyhelminthes (Flatworms), Class Turbellaria, Class Monogenea, Order Monopisthocotylea, Order Polyopisthocotylea, Class Trematoda, Subclass Aspidogasrea, Subclass Digenea; Super Order Anepitheliocystida, Order Strigeatida, Family Schistosomatidae, Subfamily Schistosomatinae, Genus *Schistosoma*, Order Echinostomatida, Family Fasciolidae, Family Paramphistomatidae, Family Echinostomatidae; Super Order Epitheliocystida, Order Plagiorchiida, Family Dicrocoeliidae, Family Troglotrematidae, Order Opisthorchiida, Family Heterophyidae, Family Opisthorchiidae, Class Cestoda, Subclass Cestodaria, Subclass Eucestoda, Order Pseudophyllidea, Family Diphyllobothriidae, Order Cyclophyllidea, Family Taeniidae, Family Hymenolepididae, Family Dilepididae, Family Mesocestoididae, Order Tetraphyllidea, Order Proteocephalata, or Order Spatheobothridea. For example, Cry proteins with the scope of the invention may be employed to prevent, inhibit or treat Roundworm, Whipworm, Hookworm, Schistosome, or *Trematodes*.

The parasite may also be a gastrointestinal tract parasitic roundworms/nematodes. The gastrointestinal tract parasitic roundworms/nematodes may include but are not limited to the following species: *Haemonochus, Cooperia, Ostertagia, Trichostrongylus, Teladorsagia. Nematodirus, Ancylostoma, Cyathostominea/Cyathostomin/Cyathostome, Strongylus, Parascaris, Ascaris, Trichuris, Oesophagostomum/Oesophagustomum, Trichiuris, Bunostomum, Oxyuris, Chabertia, Habronema, Draschia, Triodontophorus, Toxocara, Toxascaris*, and *Uncinaria. Haemonochus* species includes but is not limited to *Haemonchus contortus* and *Haemonchus placei, Cooperia* species includes but is not limited to *Cooperia oncophora, Cooperia pectinata*, and *Cooperia curticei, Ostertagia* species includes but is not limited to *Ostertagia ostertagi, Ostertagia* (*Teladorsagia*) *circumcincta*, and *Ostertagia trifurcate. Trichostrongylus* species includes but is not limited to *Trichostrongylus axei, Trichostrongylus colubriformis*, and *T. circumcincta. Teladorsagia* species includes but is not limited to *Teladorsagia* (*Ostertagia*) *circumcincta. Nematodirus* species includes but is not limited to *Nematodirus spathiger. Ancylostoma* species includes but is not limited to *Ancylostoma caninum, Ancylostoma braziliense*, and *Ancylostoma tubaeforme*. Cyathostominea/Cyathostomin/Cyathostome nematodes are also included. *Strongylus* species (small and large) includes but is not limited to *Strongylus vulgaris, Strongylus equinus*, and *Strongylus edentatus. Parascaris* species includes but is not limited to *Parascaris equorum. Strongyloides* species includes but is not limited to *Strongyloides westeri*. *Ascaris* species includes but is not limited to *Ascaris suum*. *Trichuris* species includes but is not limited to *Trichuris globulosa, Trichuris suis, Trichuris campanula*, and *Trichuris vulpis*. *Oesophagostomum Oesophagustomum* species includes but is not limited to *Oesophagustomum dentatum, Oesophagustomum quadrispinulatum, Oesophagostomum columbianum*, and *Oesophagostomum venulosum*. *Trichiuris* species includes but is not limited to *Trichiuris ovis*. *Bunostomum* species includes but is not limited to *Bunostomum trigonocephalum*. *Oxyuris* species includes but is not limited to *Oxyuris equi* (pin worms). *Chabertia* species includes but is not limited to *Chabertia ovine*. *Habronema* species includes but is not limited to *Habronema microstoma* and *Habronema muscae*. *Draschia* species includes but is not limited to *Draschia megastoma*. *Triodontophorus* species includes but is not limted to *Triodontophorus minor* and *Triodontophorus serrates*. *Toxocara* species includes but is not limted to *Toxocara canis* and *Toxocara cati*. *Toxascaris* species includes but is not limted to *Toxascaris leonine*. *Uncinaria* species includes but is not limted to *Uncinaria stenocephala*. Human parasitic roundworms of the gastrointestinal tract include but are not limited to the hookworms *Ancylostoma duodenale* and *Necator americanus*, the whipworm *Trichuris trichiura*, the roundworm *Ascaris lumbricoides*, the threadworm *Strongyloides stercoralis*, and the pinworm *Enterobius vermiculari*.

As used herein, unless the context makes clear otherwise, "treatment," and similar words such as "treated," "treating" etc., indicates an approach for obtaining beneficial or desired results, including and preferably clinically desirable results. Treatment can involve optionally either the amelioration of symptoms of the disease or condition, or the delaying of the progression of the disease or condition.

As used herein, unless the context makes clear otherwise, "reducing the likelihood of occurrence," "prevention," and similar words such as "prevented," "preventing" etc., include approaches for preventing, inhibiting, or decreasing the likelihood of the onset or recurrence of a disease or condition, in a manner that exhibits statistical significance, for example, when compared to the results obtained when the indicated method steps are omitted. Similarly, also included are preventing, inhibiting, or decreasing the likelihood of the occurrence or recurrence of the symptoms of a disease or condition, or optionally delaying the onset or recurrence of a disease or condition, or delaying the occurrence or recurrence of the symptoms of a disease or condition. As used herein, "prevention" and similar words also include reducing the intensity, effect, symptoms and/or burden of a disease or condition prior to onset or recurrence of the disease or condition. Methods according to these and related embodiments may be practiced using an effective amount or a therapeutically effective amount of an agent that substantially eradicates, reduces the severity of, or reduces the likelihood of occurrence of a soil-transmitted helminth (STH) infection. As used herein, an "effective amount" or a "therapeutically effective amount" of a composition, agent or substance is that amount sufficient to obtain a desired biological effect, such as beneficial results, including clinical results.

In certain preferred embodiments, the herein described compositions for treating or reducing the severity or likelihood of occurrence of an STH infection will be formulated as pharmaceutical compositions, which will preferably be formulated for oral delivery. Pharmaceutical compositions are formulated so as to allow the agent(s) contained therein to be bioavailable upon administration of the composition to a human.

It will be appreciated that the practice of the several embodiments of the present invention will employ, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., *Current Protocols in Molecular Biology or Current Protocols in Immunology*, John Wiley & Sons, New York, N.Y. (2009); Ausubel et al., *Short Protocols in Molecular Biology*, $3^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

As used in this specification and the appended claims, the singular forms "a," "an" and "the" include plural references unless the content clearly dictates otherwise. Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment in this specification is to be applied mutatis mutandis to every other embodiment unless expressly stated otherwise.

EQUIVALENTS

While particular steps, elements, embodiments and applications of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

The following Examples are presented by way of illustration and not limitation.

Example 1

Expression of Cry Proteins in *Lactobacillus* (LAB)

Cry proteins (full length protoxins and truncated toxins; 4 constructs total) are cloned and expressed in two *Lactobacilli*, *L. acidophilus* and *L. gasseri*. The Klaenhammer group at North Carolina State University has sequenced the genome of *L. acidophilus* NCFM and *L. gasseri* ATCC33323 and developed numerous genetic tools for gene cloning and expression of proteins, enzymes, and vaccines in these microbes. See, e.g., Mohamadzadeh, et al. PNAS 106, 4331-6 (2009)) and Goh, Y. J. et al. APPL ENVIRON MICROBIOL 75, 3093-105 (2009))

To enhance translation efficiency and Cry protein expression, codon optimization can be employed in which the codon use of a given Cry protein is altered to match that of the most frequently used codons found in the probiotic bacterium of interest. An example of successful application of this technique is given in Pusch et al., J Acquir Immune Defic Syndr 40:512-520 (2005). An example of a codon optimization tool that can be found by simple googling "codon optimization tool" is the website http://www.jcat.de/, which includes genome information from probiotic bacteria. Thus, this website can be used to codon optimize a Cry protein for expression in a particular probiotic bacterium. Level of product and/or secretion of Cry proteins (e.g., Cry5B and Cry21A) are determined using Western blotting with antibodies. The use of different probiotic species, different Cry proteins (e.g., Cry5B and Cry21A), and different versions of each (full length and truncated constructs) will maximize likelihood of success in Cry protein expression. The genetic constructs may also include a genetic strategy for containment of genetically modified bacterium, e.g., a thymidine auxotroph. (Steidler, L. et al., Nat. Biotechnol. 21: 785-89 (2003))

Figure 6:
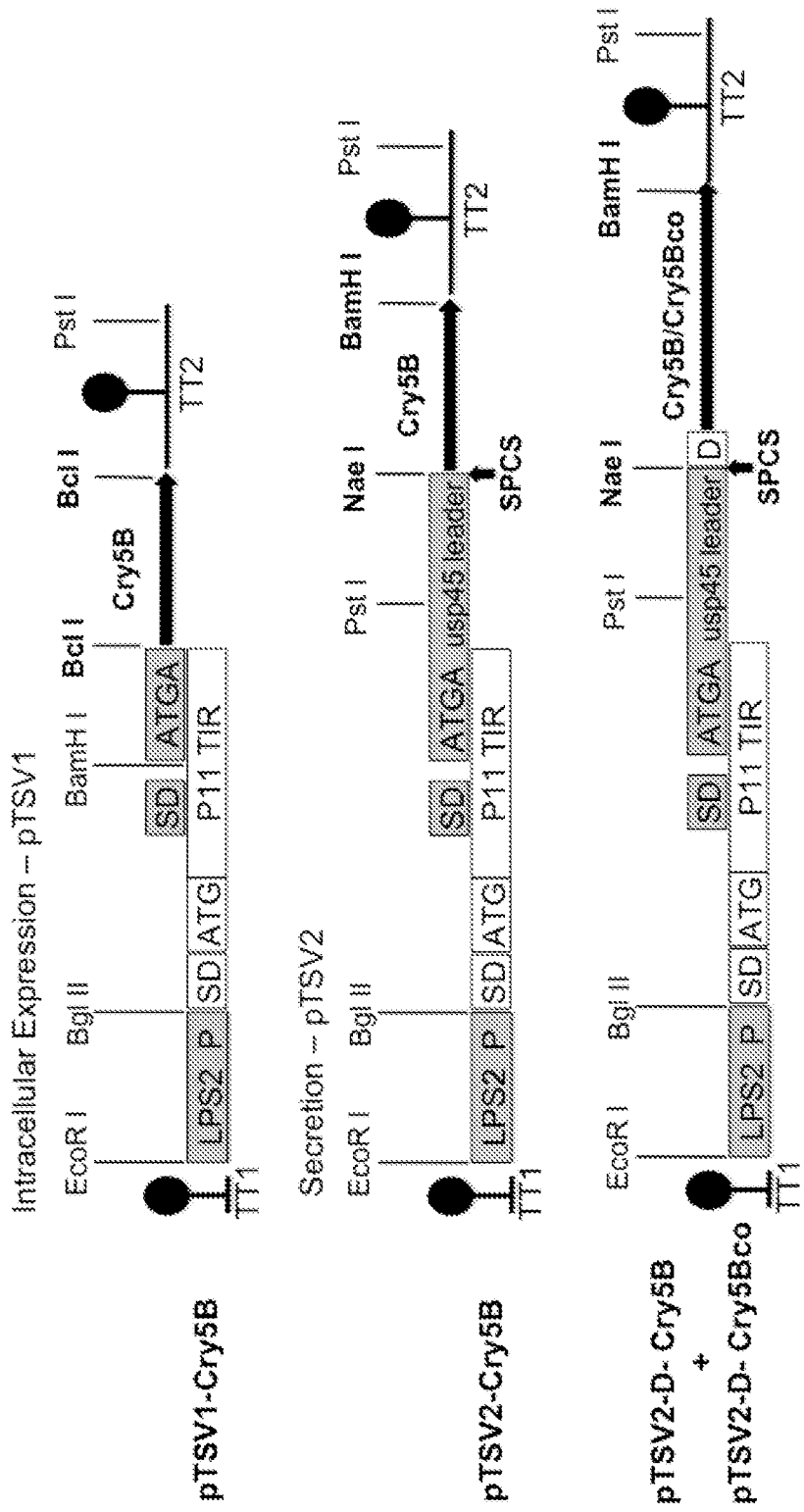
FIG. 6 illustrates the design of an expression system for heterologous protein secretion in LAB (Lactic Acid Bacteria). Expression cassettes for heterologous protein CV-N for intracellular expression (pTSV1-CVN) and secretion into the medium (pTSV1-CVN).
Figure 7:
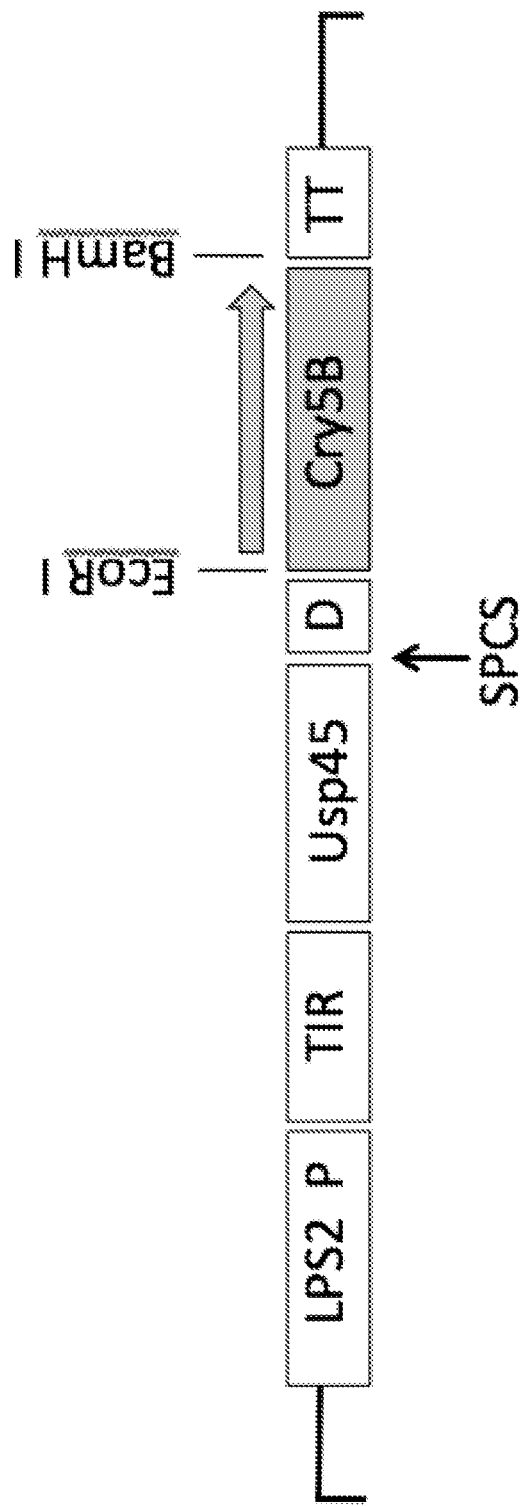
FIG. 7 illustrates secretion of HIV-1 fusion inhibitors by *Lactobacillus* spp.
Figure 8:
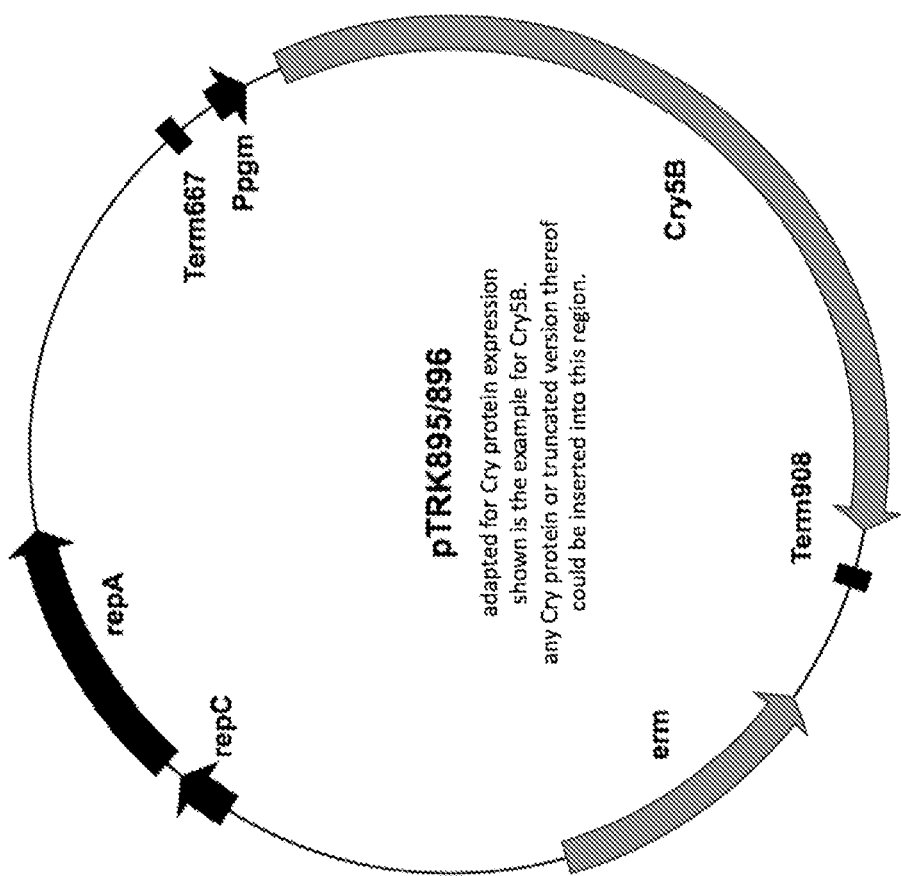
FIG. 8 shows an example of cloning the pag gene into the pgm promoter system.

Anthelmintic Cry proteins (including and not limited to Cry5B and its subvariants, Cry13A and its subvariants, Cry14A and its subvariants, and Cry21A and its subvariants) are expressed, as both intracellularly expressed and secreted forms, in lactic acid bacteria (LAB) such as *Lactobacillus plantarum* NCIMB8826 or ATCC 14917, *Lactococcus lactis* MG1363, and *Lactobacillus gasseri* ATCC 9857 using the pTSV1 and pTSV2 vectors. (See Pusch O, et al. "Bioengineering lactic acid bacteria to secrete the HIV-1 virucide cyanovirin." J ACQUIR IMMUNE DEFIC SYNDR 40: 512-520 (2005) and Pusch O, et al. "An anti-HIV microbicide engineered in commensal bacteria: secretion of HIV-1 fusion inhibitors by lactobacilli." AIDS 20: 1917-1922 (2006)) This expression system (pTSV1 and pTSV2 vectors) includes derivatives of the pTREX1 broad Gram-positive host range vector as well as the pUC origin of replication and ampicillin resistance gene to enable them to be used as shuttle vectors in *E. coli*. Expression is driven by the phage promoter LPS2 followed by the translation initiation region from *L. lactis* promoter 11. These elements contain Shine-Dalgarno as well as ATG and ATGA start/stop translation inititaiton codons. FIGS. 6 and 7 describe these vectors and their use for heterologous expression of other proteins. The vectors are assembled using PCR and restriction sites and common molecular biology techniques. See id.

FIG. 6 depicts the design of an expression system for heterologous protein secretion in LAB—expression cassettes for Cry5B for intracellular expression (pTSV1-Cry5B) and secretion into the medium (pTSV2-Cry5B). Restriction sites used for cloning are in bold. Usp45 leader indicates gene fusions with the leader sequence of the lactococcal secreted protein Usp45, followed by its original signal peptidase cleavage site DTNSD (SEQ ID NO: 25) (D) for enhanced secretion (pTSV2-Cry5B). Vertical black arrows indicate the signal peptidase cleavage site (SPCS), followed by Cry5B directly (pTSV2-Cry5B) or propeptide sequence DTNSD (SEQ ID NO: 25) (pTSV2-Cry5B/pTSV2-D-Cry5Bco). Cry5B co indicates codon optimization of Cry5B for expression in recombinant LAB. TT1 and TT2 indicate transcription terminators; LPS2 P, LPS2 bacteriophage promoter; SD, Shine-Dalgarno motif; ATG and ATGA (start/stop), translation initiation start codons; P11 TIR, translation initiation region from *L. lactis* promoter 11 See Pusch, O. et al., "Bioengineering Lactic Acid Bacteria to Secrete the HIV-1 Virucide Cyanovirin" J Acquir Immune Defic Syndr 40(5): 512-20 (Dec. 15, 2005).

FIG. 7 depicts a pTSV2 expression and secretion cassette. Fusion inhibitor sequences are codon adjusted to the codon usage of *L. plantarum* and are introduced into unique EcoRI and BamHI restriction sites. Expression is driven by the phage promoter LPS2. See Pusch, O et al., "An anti-HIV microbicide engineered in commensual bacteria: secretion of HIV-1 fusion inhibitors by lactobacilli." AIDS 20: 1917-22 (2006).

Using either a unique engineered restriction site (e.g., Bcl 1, Nae 1, or other appropriate restriction site compatible with each Cry gene and the vectors) or PCR sewing, the Cry gene is fused downstream in-frame of the ATGA sequence in the P11 TIR region. In the case of intracellular Cry protein expression, this pTSV1 vector system is sufficient. In the case of secreted Cry protein expression, the lactococcal signal leader derived from the usp45 gene of *L. lactis* is fused just downstream of the ATGA sequence (vector pTSV2) and upstream of the Cry gene, which will allow the Cry protein to be fused to the signal sequence. In all cases, the TT2 transcription terminator is placed downstream of the Cry gene sequence. Both full-length (pro-toxin) and truncated (e.g., amino acids 1-697 of Cry5B and similar truncations in Cry13A, Cry14A, and Cry21A, which removes the protoxin domain just after conserved block 5 (or box V)) Cry proteins are expressed this way. The advantage of truncated Cry proteins is that they may be easier to express or secrete due to their smaller size. To aid in secretion of the Cry protein, the negatively charged peptide DTNSD (SEQ ID NO: 25) (the first five amino acids of the secreted *L. lactis* Usp435 protein) may be fused (using recombinant DNA techniques) to the N-terminus of the Cry protein. See id. In addition, the codon usage of the Cry protein can be optimized using codon usage found in each LAB to permit higher levels of expression in that LAB. See id. Once assembled, the vectors (each Cry protein, full length and truncated versions, intracellular expression and extracellular secretion versions) are transformed into *L. lactis, L. plantarum, L. gasseri*, or other LAB using standard techniques. See id. It has been found that expression from these vectors are compatible with these three (and likely many more) LAB. See id.

In addition to expression of intracellular Cry protein and secreted Cry protein, the vectors are modified to allow expression of Cry protein anchored in the membrane of the LAB. For these studies, the Cry proteins (either full length or truncated) are fused at their C-termini to the C-terminal membrane anchoring domain of lactococcal cell surface-associated proteinase (PrtP). See Norton P M, et al. "Factors affecting the immunogenicity of tetanus toxin fragment C expressed in *Lactococcus lactis*." FEMS IMMUNOL MED MICROBIOL 14: 167-177 (1996). The domain is fused to the Cry protein using standard DNA recombinant techniques.

Example 2

Expression of Cry Proteins in *Bifidobacteria*

An expression system for *Bifidobacteria* has been described. See Shkoporov A N, et al. "Production of human basic fibroblast growth factor (FGF-2) in *Bifidobacterium breve* using a series of novel expression/secretion vectors." BIOTECHNOL LETT 30: 1983-1988 (2008). Cry proteins are cloned and expressed in *Bifidobacteria* such as *B. breve* UCC2003, *B. longum* VMKB44, and *B. bifidum* ATCC 15696 using a vector system (pESH46, pESH47, pESH86) that employs the promoter/TIR and terminator regions of the hup gene or the promoter/TIR region of the gap gene along with the terminator of the hup gene. Expression under these promoters allows for intracellular production of Cry proteins (full length and truncated). To allow for secretion, the first 11 N-terminal amino acids of a mature polypeptide of the bifidobacterial Sec2 secreted protein is fused to the N-terminus of the Cry proteins. These constructs are transformed into *Bifidobacteria* and are tested for expression and bioactivity as described below.

Example 3

Expression of Cry Proteins in *Bacillus*

Figure 9:
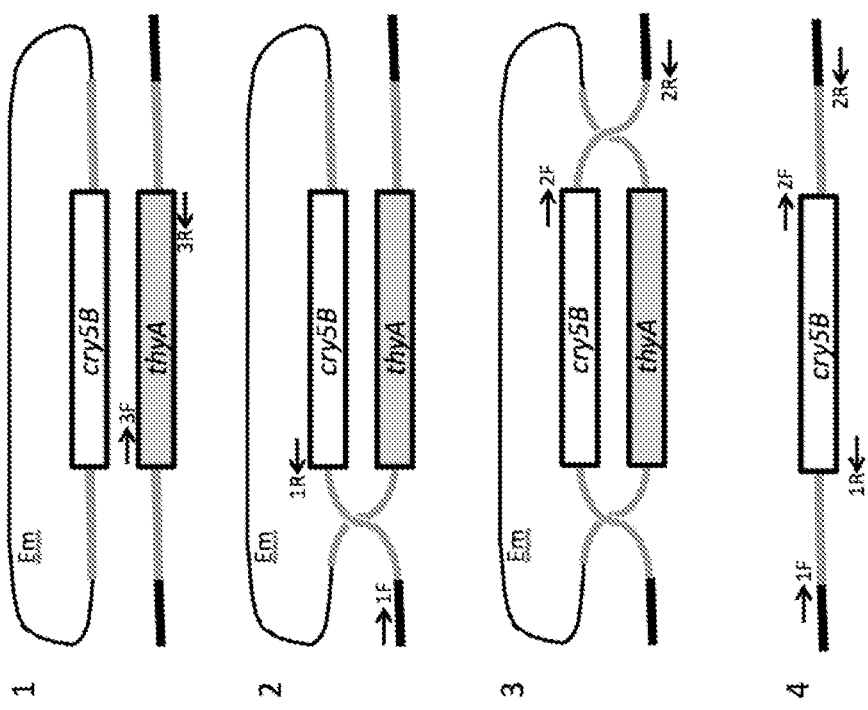
FIG. 9 illustrates recombinant *L. lactis* MG1363 strains in which the thyA gene is replaced by the respective full-length or truncated cry gene, with or without a leader sequence, via double homologous recombination.

*Bacillus cereus* (e.g., var. *toyo somal mutations in Lactococcus lactis which allows fast analysis of targeted genes." J BACTERIOL 177: 7011-7018 (1995)) to produce recombinant L. lactis MG1363 strains in which the thyA gene is replaced by the respective full-length or truncated cry gene, with or without a leader sequence, via double homologous recombination. Exchange between thyA and cry5B genes is depicted in FIG. 9. Gray lines represent target areas for recombination, thick black lines represent nontarget MG1363 chromosome fragments and thin black lines represent the exchange vector. 1, 2 and 3 represent PCR primer pairs (F and R), designed in such a way that PCR using primer pair 1 shows collinearity between chromosomal DNA located 5' of the target area and cry5B (PCR1), that PCR using primer pair 2 shows collinearity between chromosomal DNA located 3' of the target area and cry5B (PCR2), and that PCR using primer pair 3 shows the presence of thyA (PCR3). Stages include (1) introduction of the nonreplicative vector; (2) 5' crossover, forced by erythromycin selection and identified by PCR1; (3) second crossover in the absence of Em, identified through screening by PCR2; and (4) acquisition of desired transgenic chromosome organization. Steidler L, et al. NAT BIOTECHNOL 21: 785-789 (2003).

Figure 10A:
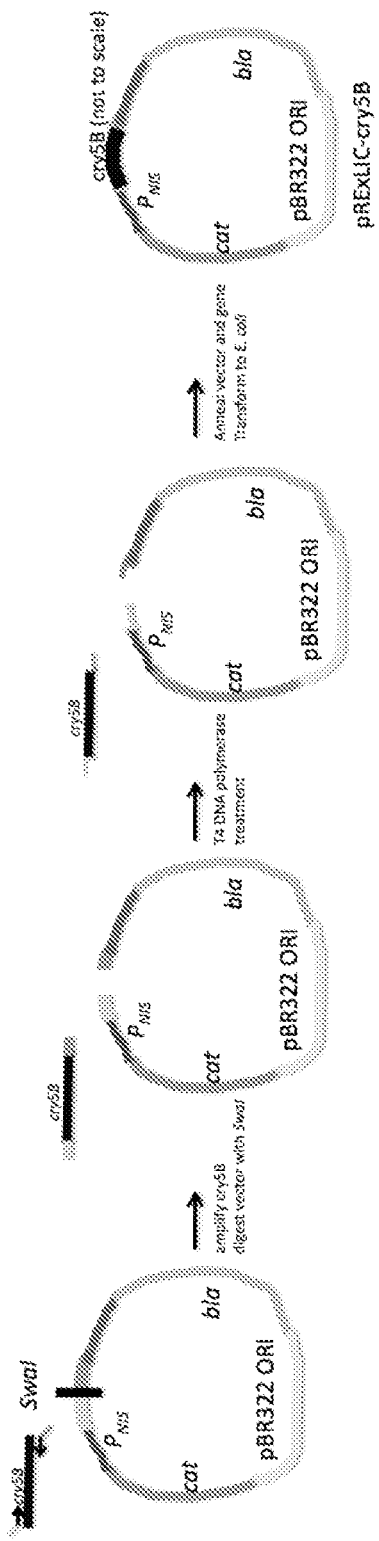
FIG. 10 (FIGS. 10A-10B) illustrate a cloning strategy with an inducible nisin promoter that uses a combination of vector-backbone exchange (VBEx) and ligation independent cloning (LIC).

Chromosomal mutants of L. lactis that are selected for the testing of the biological activity of expressed Cry proteins are those that contain the least amount of foreign DNA and contain an intact thyA promoter region directly upstream of the insertional deletion. Mutants of this sort are detected by southern blotting using a combination of thyA and cry gene probes. The ability of each strain to produce intracellular, secretory or membrane-bound Cry5B, Cry21A, Cry14A, or Cry13A and their truncated forms respectively are then tested in vivo. Expression and bioactivity are tested as described below.

exchange (VBEx) and ligation independent cloning (LIC), a cloning strategy that has been well characterized and shown in FIG. 10. In FIG. 10A, in the LIC procedure, cry5B is amplified using primers containing LIC-specific overhangs. The plasmid is linearized by SwaI restriction in the LIC cassette. Single-stranded overhangs of the PCR product and vector are generated using T4 DNA polymerase. The complementary overhangs of PCR product and vector anneal upon mixing. The resulting heteroduplex is transformed efficiently into E. coli. In FIG. 10B, in the VBEx strategy, the L. lactis expression vector pNZxLIC is cut at the two introduced SFiI sites. Plasmid pERL consists of the pSH71 replicon from pNZxLIC fused to an erythromycin marker. Plasmid pRExLIC consists of the cat marker and LIC sequence from pNZxLIC, fused to the E. coli pBR322 replicon and the bla marker. This vector is subjected to the LIC procedure (a); then the pNZxLIC vector is restored by mixing pERL and pRExLIC-cry5B, digestion with SfiI, ligation and selection on the ability to replicated in L. lactis in the presence of chloramphenical. Geertsma E R and Poolman B "High-throughput cloning and expression in recalcitrant bacteria." NAT METHODS 4: 705-707 (2007). This strategy eliminates the use of large shuttle vectors and generates genuine expression plasmids for recalcitrant bacteria. Using nLIC or cLIC primers, each respective full length or truncated cry gene is amplified and cloned into the appropriate vectors in Table 2 below for the VBEx procedure. See id. Expression, secretion, and bioactivity of Cry proteins in each recombinant L. lactis NZ9000 strain is then characterized. Expression and bioactivity are tested as described below. Nisin is included either in the growth medium (bacterial growth) or in the water/food (mice) to induce expression.

TABLE 2

| Vector name | Protein sequence | Protein sequence after TEV protease cleavage | Expression host |
| --- | --- | --- | --- |
| pREnLIC | M-His$_{10}$-G-TEV site-protein | G-protein | L. lactis NZ9000 |
| pREcLIC | MGGGFA-protein-TEV site-His$_{10}$ | MGGGFA-protein-ENLYFQ | L. lactis NZ9000 |
| pREcLIC-GFP | MGGGFA-protein-TEV site-GFP-His$_{10}$ | MGGGFA-protein-ENLYFQ | L. lactis NZ9000 |
| pRE-USP45-nLIC | M-ssUSP45$^{21}$-His$_{10}$-G-TEV site-protein | G-protein | L. lactis NZ9000 |
| pBADnLIC | M-His$_{10}$-G-TEV site-protein | G-protein | E. coli |
| pBADcLIC | MGGGFA-protein-TEV site-His$_{10}$ | MGGGFA-protein-ENLYFQ | E. coli |
| pBADcLIC-GFP | MGGGFA-protein-TEV site-GFP-His$_{10}$ | MGGGFA-protein-ENLYFQ | E. coli |
| pBAD-OmpA-nLIC | M-ssOmpA$^{21}$-His$_{10}$-G-TEV site-protein | G-protein | E. coli |

Example 6

NICE Driven Expression of CRY Proteins in Lactococcus Lactis

An alternative expression system for multidomain proteins in L. lactis is the highly inducible Nisin-controlled gene expression system sold by MoBiTec GmbH, Germany. Nisin is a natural food preservative produced by L. lactis and is nontoxic to humans. In fact, it has been show that 30% of consumer milk products contain substantial amounts of nisin. See Beasley S S and Saris P E "Nisin-producing Lactococcus lactis strains isolated from human milk." APPL ENVIRON MICROBIOL 70: 5051-5053 (2004). L. lactis NZ9000, a derivative of MG1363 in which the transduction signals nisR and nisK were inserted into the chromosome, is used as a host for the expression of Cry proteins. The full CDS or truncated forms of either Cry5B, Cry21A, Cry14A, or Cry13A will be placed downstream of the inducible nisin promoter by using a combination of vector-backbone exchange (VBEx) and ligation independent cloning (LIC), a Other vectors for the expression of the full length or truncated forms of either Cry5B, Cry21A, Cry14A, or Cry13A include the E. coli/Lactococcus shuttle vector pMSP3535H3, which incorporates the nisin immunity gene (nisI) and the NICE expression system on the same plasmid. See Oddone G M, et al. "Incorporation of nisI-mediated nisin immunity improves vector-based nisin-controlled gene expression in lactic acid bacteria." Plasmid 61: 151-158 (2009). This system has been used to express recombinant proteins in a variety of gram-positive organisms including L. lactis, Lactobacillus paracasei, Streptococcus mutans, Enterococcus faecalis, Streptococcus gordonii. See id. Full length or truncated forms of either Cry5B, Cry21A, Cry14A, or Cry13A, with and without leader peptide sequences for partial or full secretion, are cloned into pMSP3535H3 downstream of the nisin promoter. The constructs are transformed into plasmid free L. lactis MG1363 recombinant strains and are characterized for expression, secretion and bioactivity of Cry proteins. Expression and bioactivity are tested as described below.

Example 7

Expression of Cry Proteins in Probiotic *E. Coli* Using the Arabinose Operon The VBEx procedure also extends to other host organisms with plasmids. One of the most intensively studied probiotics is *Escherichia coli* Nissle 1917 (EcN). See, e.g., Schroeder B, et al. "Preventive effects of the probiotic *Escherichia coli* strain Nissle 1917 on acute secretory diarrhea in a pig model of intestinal infection." DIG DIS SCI 51: 724-731 (2006). Using the appropriate *E. coli* LIC/VBEx vectors in Table 2, probiotic EcN strains expressing the full length or truncated forms of either Cry5B, Cry21A, Cry14A, or Cry13A are generated in the same fashion as described above for *L. lactis*. Expression of these proteins is dependent upon arabinose, with the genes being placed downstream of the arabinose operon (pBAD). Expression and bioactivity are tested as described below.

Example 8

Curative Experiment A—Protocol for Infections, Anthelmintic Treatment, and Determination of Treatment Efficacy (Small Intestine Roundworm Parasite)

Six week old female Swiss Webster mice are infected per os with a suspension of 200±10 *Heligmosomoides bakeri* infective third-stage larvae in 0.1 mL of distilled water. The outbred strain Swiss Webster is used to better "mimic" treating a genetically diverse host (like humans). Each mouse is gavaged on day 15 post-infection (PI) with 0.1 mL of buffer, 0.1 mL of high dose LAB control (transformed with empty vector) or 0.1 mL of high dose LAB expressing Cry protein (6-10 animals/group). Progression of the infection is determined by fecal egg counts every other day beginning 3 days before treatment. Mice are placed individually in empty plastic cages for 1 h each morning, and the fecal pellets are collected into 50 mL centrifuge tubes. The number of eggs present is counted using the modified McMaster technique. See Hu Y, et al. "*Bacillus thuringiensis* Cry5B protein is highly efficacious as a single-dose therapy against an intestinal roundworm infection in mice." PLoS NEGL TROP DIS 4: e614 (2010). At 1, 2, or 3 weeks after treatment, the animals from all three groups are euthanized and the intestinal worm burdens are counted. Using fecal egg counts and intestinal worm burdens, the ability of Cry-expressing LAB to cure small intestinal roundworm infections are ascertained.

Example 9

Curative Experiment B—*Trichuris Muris*: Whipworm (Large Intestine Roundworm Parasite)

Twenty-one (21) 6-8 week old female AKR mice are infected per os with 200 infectious-staged *T. muris* eggs. Thirty (30) days post-infection, the mice are treated per os (7/group) with a single 0.1 mL dose of buffer, 0.1 mL high dose of LAB control (transformed with empty vector), or 0.1 mL of high dose LAB expressing Cry protein. Fecal egg counts are taken three days before treatment and then every other day until necropsy (same protocol to collect eggs as per *H. bakeri*). The mice are euthanized either 1, 2 or 3 weeks after treatment and worm burdens in the large intestine are determined. Using fecal egg counts and intestinal worm burdens, the ability of Cry-expressing LAB to cure large intestinal roundworm infections are ascertained.

Example 10

Curative Experiment C—*Ancylostoma Ceylanicum*: Hookworm (Blood Feeding, Small Intestinal Roundworm Parasite)

Twenty one (21) 4-week old Syrian hamsters are infected per os with 150 infectious staged L3 *A. ceylanicum* hookworm larvae. Fourteen (14) days post-infection, the hamsters are treated per os with a single 0.1 mL dose of buffer, 0.1 mL high dose of LAB control (transformed with empty vector), or 0.1 mL of high dose LAB expressing Cry protein. Body weight, hemoglobin levels, and fecal egg counts (beginning three days before treatment) are monitored every other day until day 21, 28, or 35, at which point the animals are euthanized and worm burdens in the small intestine are determined. Using fecal egg counts, hemoglobin levels, and intestinal worm burdens, the ability of Cry-expressing LAB to cure blood-feeding small intestinal roundworm infections are ascertained.

Example 11

Preventative-Type Experiment A

Swiss Webster mice as above (6-10 each group, three groups) receive either 0.1 mL buffer, 0.1 mL high dose empty vector-transformed LAB without Cry protein expression, or 0.1 mL high dose vector-transformed LAB with Cry protein expression. Some (about 2-21) days later, all groups of mice are then challenged with 200 *H. bakeri* infectious larvae as described above. Two weeks later after infection challenge, fecal egg counts are determined every other day for one to two weeks, after which time the mice are euthanized to determine intestinal roundworm burdens. Fecal egg counts and intestinal roundworm burdens are used to determine if the probiotics protected the mice against a challenge with a small intestine roundworm parasite (i.e., prevented infection).

Example 12

Preventative-Type Experiment B

AKR mice as above (6-10 each group, three groups) receive either 0.1 mL buffer, 0.1 mL high dose empty vector-transformed LAB without Cry protein expression, or 0.1 mL high dose vector-transformed LAB with Cry protein expression. Some (about 2-21) days later, all groups of mice are then challenged with 200 *T. muris* infectious eggs as above. Thirty (30) days after infection challenge, fecal egg counts are determined every other day for one to two weeks, after which time the mice are euthanized to determine intestinal roundworm burdens. Fecal egg counts and intestinal roundworm burdens are used to determine if the probiotics protected the mice against a challenge with a large intestine roundworm parasite (i.e., prevented infection).

Example 13

Preventative-Type Experiment C

Hamsters as above (6-10 each group, three groups) receive either 0.1 mL buffer, 0.1 mL high dose empty vector-transformed LAB without Cry protein expression, or 0.1 mL high dose vector-transformed LAB with Cry protein expression. Some (about 2-21) days later, all groups of hamsters are then challenged with 150 *A. ceylanicum* infectious larvae as above. Two weeks after infection challenge, fecal egg counts are determined every other day for one to two weeks, after which time the hamsters are euthanized to determine intestinal roundworm burdens. Fecal egg counts and intestinal roundworm burdens are used to determine if the probiotics protected the hamsters against a challenge with a small intestine blood-feeding roundworm parasite (i.e., prevented infection). In addition to experiments with rodents described above, similar experiments could be carried out with other mammals, e.g., felines, canines, bovines, equines, swines, caprines, ovines, and primates.

Example 14

*Bacillus Subtilis* Strain Engineered for Treatment of STHs

Construction and verification of strains and preparation of lysates. The *B. subtilis* strain PY79 was transformed with the plasmid vector pHT3101 (PY79-vector) or with a pHT3101-derived cry5B plasmid (PY79-Cry5B) (29). Natural competence was generated in PY79 by use of a standard medium shift protocol (30). To generate spore lysates and spore crystal lysates, PY79 strains were sporulated for 96 h at 37° C., spun down, washed once with prechilled 0.5MNaCl, and washed again with prechilled sterile double-distilled water. Final pellets were stored at −80° C. until use.

Transformants were screened by PCRs using the following primers on all three strains (PY79, PY79-vector, and PY79-Cry5B): Cry5B primer forward 1 (CGTTCAAAAT-CATCCGTAAATG) (SEQ ID NO: 26) with Cry5B primer reverse 1 (AAATGCATGAACCACTTCCAC) (SEQ ID NO: 27) (predicted product of 586 nucleotides [nt]), Cry5B primer forward 2 (TGGCAACAATTAATGAGT TGTATCCAG) (SEQ ID NO: 28) with Cry5B primer reverse 2 (CTGCCTTGACAAATGG CTACT) (SEQ ID NO: 29) (predicted product of 497 nt), and pHT3101 primer forward (CACCCCAGGCTTTACACTTTA) (SEQ ID NO: 30) with pHT3101 primer reverse (AGG CGAT-TAAGTTGGGTAACG) (SEQ ID NO: 31) (predicted product of 220 nt with empty vector pHT3101 and 6.5 kb with the cry5B insert). Templates were prepared as follows.

Single colonies of PY79, PY79-vector, and PY79-Cry5B were picked from plates and suspended in 50 μl of sterile double-distilled water. These bacterial solutions were boiled for 3 min and then snap-frozen in liquid nitrogen for 3 min. The procedure was repeated for a total of three cycles of boiling-freezing. Supernatants were collected and used as PCR templates. Cycles were carried out using Taq polymerase under the following conditions: 94° C. for 3 min and then 35 cycles of 94° C. for 30 s, 54° C. for 45 s, and 72° C. for 1 min, followed by 72° C. for 10 min. All amplified products were sequenced to confirm identities. To determine putative transcription factor binding sites, 1.5 kb of the region upstream of the cry5B start codon was entered into the DBTBS database (31; http://dbtbs.hgc.jp/), and the P value was set to 0.05. Two putative sigma E binding sites were revealed, 43 and 712 bases upstream of the start codon.

The identity of the strains was further confirmed by analysis of selected proteins. Cell lysates were fractionated by 8% SDS-PAGE, and protein bands were excised from the gels. Proteins were prepared for mass spectrometric sequencing by in-gel digestion with trypsin and then analyzed by high-pressure liquid chromatography (HPLC) in combination with tandem mass spectroscopy (MS/MS) using electrospray ionization as described previously (32). The collected data were analyzed using MASCOT (Matrix Sciences) and Protein Pilot 4.0 (AB Sciex) for peptide identifications.

SEM. In preparation for scanning electron microscopy (SEM) imaging, the samples were drop-cast on a polished Si chip and dried in a vacuum. The samples were then sputter coated with iridium in an Emitech K575X sputter coater. The sputter current was 85 mA, the argon pressure was 2 Pa, and the deposition time was 7 s, resulting in a film thickness of <10 nm. The samples were imaged with an FEI XL30 ESEM FEG instrument, using a 10-kV beam energy and a spot size of 3.

*C. elegans* bioassays and *A. ceylanicum* curative experiments. *Ancylostoma ceylanicum* hookworms were maintained in golden Syrian hamsters (14). All animal experiments were carried out under protocols approved by the UCSD Institutional Animal Care and Use Committees (IA-CUC). All housing and care of laboratory animals used in this study conformed to the *Guide for the Care and Use of Laboratory Animals* (33) and all requirements and regulations issued by the USDA, including regulations implementing the Animal Welfare Act (P.L. 89-544) as amended (see 18-F23). *Caenorhabditis elegans* was maintained according to standard procedures (34).

The concentration of Cry5B protein in PY79-Cry5B spore crystal lysates was determined as previously described for BtCry5B spore crystal lysates (13). Dose-dependent *C. elegans* mortality bioassays (three independent trials) were carried out as previously described (13), including use of tetracycline at 30 μg/ml, except that the assays were carried out for 6 days and each well contained-25 to 30 animals (with triplicate wells per experiment and three independent experiments). The 50% lethal concentration (LC50) was calculated using PROBIT (35).

For in vivo curative experiments, male hamsters were infected per os with 150 *A. ceylanicum* infectious larvae. On day 17 postinoculation (p.i.), a fecal sample was collected from each hamster, and the number of eggs was counted using the modified McMaster technique (13). On the basis of these fecal egg counts, the hamsters were segregated to ensure that the groups (control and treatment) had roughly equivalent infection levels. On day 18 p.i., hamsters were weighed individually and given either PY79-Cry5B spore lysate or a spore dose equivalent of PY79-vector spore lysate per os through a blunt-ended gavage needle. Feces were collected on days 1 and 3 post-treatment to determine fecal egg counts (13). The hamsters were sacrificed on day 22 p.i., and intestinal parasite burdens were determined as described previously (14). The one-tailed Mann-Whitney test was performed to compare the two groups for significance in the experiment using a dose of 10 mg/kg of body weight (data were calculated and plotted using Prism 5 [GraphPad Software Inc., La Jolla, Calif.]). Fecal egg counts were compared using one-tailed Student's t test. For the dose-response experiment, results for each treatment group were compared to those for the control group by one-way analysis of variance and Dunnett's method.

Results

Cry5B was well produced in *Bacillus subtilis* PY79. A recombinant cry5B plasmid engineered for *B. thuringiensis* (29) was purified from *B. thuringiensis* and transformed into *B. subtilis* strain PY79 by standard transformation techniques. This plasmid, based upon the *E. coli-B. thuringiensis* shuttle vector pHT3101 (36), contained the endogenous Cry5B promoter and 3'-untranslated region driving expression of the wild-type cry5B gene (29). To generate an empty vector control strain, empty vector pHT3101 was also transformed into PY79. The presence of the cry5B gene in the PY79-Cry5B strain and its absence from both the parent PY79 strain and the control strain (PY79-vector) were confirmed by PCR. PCR detection of the plasmid in the PY79-vector strain and its absence from the parent PY79 strain were also confirmed. PY79 was able to maintain both the cry5B plasmid and pHT3101 under standard antibiotic selection with erythromycin, indicating that the origin of replication for *B. thuringiensis* functioned in *B. subtilis*, as demonstrated previously (37).

The PY79-Cry5B and PY79-vector strains were sporulated. Robust expression of a protein of the size of Cry5B was detected by PAGE only in the PY79-Cry5B strain. Mass spectroscopy confirmed that the protein was indeed Cry5B. On the basis of quantitation relative to bovine serum albumin (BSA) standards on polyacrylamide gels, Cry5B was expressed at 10 mg/liter culture, which was ~7.5-fold lower than the Cry5B expression level in *B. thuringiensis* (75 mg/liter) (29). Two other bands common to both PY79-vector and PY79-Cry5B were identified by mass spectroscopy as the 60-kDa chaperonin protein and an oligopeptide-binding protein from *B. subtilis* 168, the parent strain of PY79 (38). These assays confirmed that Cry5B was expressed in the PY79-Cry5B strain and that the strain was *B. subtilis* PY79.

Crystal proteins expressed during sporulation of *B. thuringiensis* assemble into crystalline inclusions in the mother cell compartment that are often bipyramidal in shape (39). This assembling is also true of Cry5B produced in *B. thuringiensis* (40). Whereas no crystals were detected by SEM upon sporulation of the PY79-vector strain, many SEM-detectable small crystalline inclusions were present upon sporulation of the PY79-Cry5B strain. Some of these crystals were bipyramidal in shape; others appeared to be truncated versions of such crystals. Thus, Cry5B not only was expressed in PY79 but also assembled into crystalline inclusions.

Cry5B made by PY79 was bioactive. To test whether or not Cry5B made by PY79 was bioactive, dose-dependent mortality assays were set up using the laboratory roundworm *C. elegans* in a standard 48-well format (13, 41). The Cry5B component of PY79-Cry5B spore crystal lysates was quantitated relative to BSA standards on polyacrylamide gels. Fourth-stage larvae were incubated for 6 days in wells containing PY79-Cry5B spore crystal lysates containing fixed amounts of Cry5B. Antibiotics were included to prevent infection of the roundworms by bacteria (42). Cry5B made by PY79 was found to kill *C. elegans*, with an LC50 of 4.3 μg/ml (95% confidence interval, 3.6 to 5.0 μg/ml) (FIG. 11). This LC50 was similar to the LC50 of Cry5B purified from *B. thuringiensis* (7 to 9 μg/ml) (35) under comparable conditions (25° C., 6 days). Conversely, *C. elegans* exposed to PY79-vector spore lysates (with a spore count equivalent to the highest dose used with PY79-Cry5B) was >99% viable (122/123 worms were alive). Thus, PY79 spore lysates were not lethal to *C. elegans*, and PY79 was able to produce bioactive Cry5B.

PY79-Cry5B was therapeutic against experimental hookworm infection in hamsters. Nine hamsters were infected with the hookworm parasite *A. ceylanicum*. At 18 days post-inoculation, five hamsters were treated per os with a single dose of PY9-vector spore lysate, and four were treated with a single dose of PY79-Cry5B spore crystal lysate (equivalent spore counts were used in both treatment groups; the amount of Cry5B was determined relative to BSA standards on protein gels). The single dose of Cry5B used was 10 mg/kg, chosen based on published doses of clinical anthelmintics used in the same model of hookworm disease (Table 3). Feces were collected before and after treatment in order to determine worm loading and changes to parasite egg output. At 22 days post-infection, animals were sacrificed and intestinal worm burdens determined. With a single dose, hookworm burdens were reduced 93% relative to those of the control group (P=0.009) (FIG. 12A). Strong effects could also be seen in the reduction of parasite eggs excreted into feces (91% reduction) (FIG. 12B). To determine if there was an effective dose-response relationship and if significant therapy could be provided at lower doses, another experiment was carried out with three hamsters per group and Cry5B doses of 0.4, 1.4, and 4 mg/kg. Significant clearance of parasites was seen at 1.4 and 4 mg/kg Cry5B in PY79 (69% and 79% reductions, with P values of 0.023 and 0.012, respectively).

The experiments in this Example demonstrated for the first time that *Bacillus subtilis* can be engineered to provide a significant therapeutic effect against an existing parasitic disease. This pilot study employed PY79, a laboratory strain of *B. subtilis* that has been used as a model for the delivery of viable bacterial therapies in humans and livestock and that is closely related to a food-grade *B. subtilis* species. PY79 was made to express and correctly present the BtCry5B protein in a manner that was bioactive against the laboratory roundworm *C. elegans*. A single 10-mg/kg dose (71 nmol/kg) of Cry5B administered as a Cry5B-PY79 spore crystal lysate reduced *A. ceylanicum* hookworm burdens in hamsters by 93%, and a dose as small as 1.4 mg/kg was able to provide significant therapy. In previously published data, purified Cry5B delivered at 10 mg/kg reduced hookworm burdens by 65% (14); the data disclosed herein suggest that delivery of Cry5B via PY79 spore crystal lysates was superior to delivery via purified protein.

The expression of Cry5B in *B. subtilis* employed the endogenous BtCry5B promoter and may have been influenced at least partly by two putative sigma E elements upstream of the cry5B start codon. Sigma E is a sporulation-specific promoter that is active in *B. subtilis* and is also known to be involved in crystal protein production in *B. thuringiensis* (43, 44). The engineered strain used for the present study included antibiotic resistance genes associated with the cry5B plasmid. Given the genetic tools associated with *B. subtilis* (45), a Cry5B-expressing *B. subtilis* therapeutic product for humans is contemplated that includes the cry5B gene integrated into the genome and that lacks any antibiotic resistance genes The 93% elimination (P=0.0.009) of *A. ceylanicum* hookworm parasites from hamsters by use of a single 10-mg/kg (71 nmol/kg) dose compared favorably to the results of anthelmintics used clinically (Table 3). For example, a 10-mg/kg (49 μmol/kg) dose of levamisole resulted in a 60% reduction of *A. ceylanicum* burdens in hamsters, a 10-mg/kg (17 μmol/kg) dose of pyrantel resulted in an 87% reduction in *A. ceylanicum* burdens, a 10-mg/kg (22 μmol/kg) dose of tribendimidine resulted in a 75% reduction of *A. ceylanicum* burdens, and a 1.25-mg/kg (4.7 μmol/kg) dose of albendazole resulted in an 88% reduction of *A. ceylanicum* burdens (46, 47). In addition to high efficacy, Cry5B had a different mechanism of action from that of chemical anthelmintics; Cry5B has been shown to be a pore-forming protein that binds to invertebrate-specific glycolipids and attacks the plasma membrane of the nematode intestine (34, 35, 48-50).

As described herein PY79-Cry5B was comparable to many current drugs in its efficacy on a mg/kg basis, and on a molar level, it appeared to be superior (e.g., the molar dose of Cry5B used in the present experiments was 66 times lower than the molar dose of albendazole mentioned above). The present results validated the *B. subtilis*-Cry5B approach.

Also contemplated are increasing *B. subtilis*-Cry5B specific activity, e.g., by Cry5B point mutations that increase roundworm-killing activity (51) and by optimization of fermentation conditions that can also increase crystal protein specific activity (52). Given that *Bacillus* bacteria can be produced and stored cheaply and in large quantities (53), the present results demonstrated the feasibility of Cry5B delivery by food-grade *B. subtilis* for the treatment of STH diseases.

TABLE 3

Comparison of efficacies of PY79-Cry5B and clinically used anthelmintics against *A. ceylanicum* infections in hamsters

| Treatment[a] | Dose (µmol/kg) | % Parasite reduction | P value | Reference |
|---|---|---|---|---|
| Levamisole | 49 | 60 | 0.057 | 47 |
| Pyrantel | 17 | 87 | 0.057 | 47 |
| Tribendimidine | 22 | 75 | >0.05? | 46 |
| Albendazole (1.25 mg/kg) | 4.7 | 88 | <0.001 | 47 |
| Cry5B | 0.071 | 93 | 0.009 | This Example |

[a]Treatments were administered at 10 mg/kg unless otherwise stated.

REFERENCES

Figure 13:
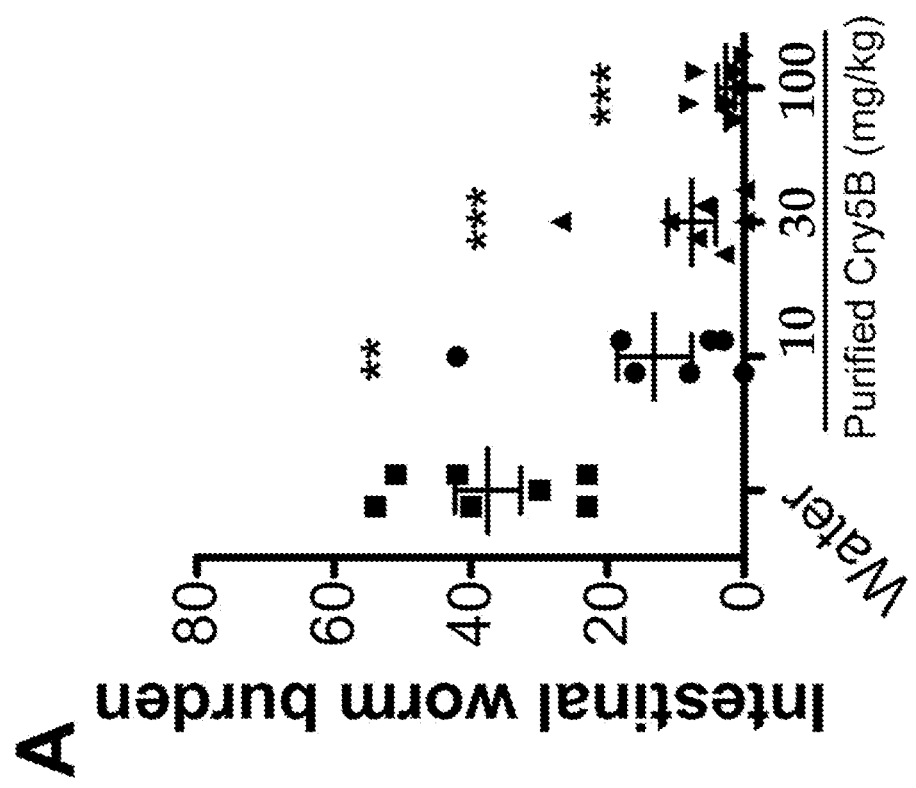
FIG. 13 shows results from an in vivo bioassay of intestinal worm burdens in golden Syrian hamsters infected with *Ancylostoma ceylanicum* hookworms as described by Hu et al. (2012 *PLoS Negl. Trop. Dis.* 6:e1900. doi:10.137/journal.pntd.0001900). The four groups (in black, n=7 per group) shown are the intestinal worm burdens from the groups of infected hamsters treated with purified full-length *B. thuringiensis* Cry5B protein (prepared according to Griffitts et al., 2001 *Science* 293:860; for sequence see FIG. 2) at a single dose of 1 mg (solid circles, 10 mg/kg), 3 mg (solid upright triangles, 30 mg/kg), or 10 mg (solid inverted triangles, 100 mg/kg) (715 nmoles/kg), or with placebo (solid squares, ddH$_2$O), respectively. The treatments were conducted on day 16 P.I. and intestinal worm burdens assessed on day 21 P.I. The worm burdens in each hamster are indicated with a separate symbol. Long horizontal bars represent mean worm burdens; smaller bars indicate SEM (standard error of the mean).

1. Bethony J, Brooker S, Albonico M, Geiger S M, Loukas A, Diemert D, Hotez P J. 2006. Soil-transmitted helminth infections: ascariasis, trichuriasis, and hookworm. Lancet 367:1521-1532.
2. Hall A, Hewitt G, Tuffrey V, de Silva N. 2008. A review and metaanalysis of the impact of intestinal worms on child growth and nutrition. Matern. Child Nutr. 4(Suppl 1):118-236.
3. Knopp S, Steinmann P, Keiser J, Utzinger J. 2012. Nematode infections: soil-transmitted helminths and trichinella. Infect. Dis. Clin. North Am. 26:341-358.
4. Tchuem Tchuente L A. 2011. Control of soil-transmitted helminths in sub-Saharan Africa: diagnosis, drug efficacy concerns and challenges. Acta Trop. 120(Suppl 1):S4-S11.
5. Hotez P J. 2008. Forgotten people, forgotten diseases: the neglected tropical diseases and their impact on global health and development. ASM Press, Washington, D.C.
6. Keiser J, Utzinger J. 2010. The drugs we have and the drugs we need against major helminth infections. Adv. Parasitol. 73:197-230.
7. Humphries D, Mosites E, Otchere J, Twum W A, Woo L, Jones-Sanpei H, Harrison L M, Bungiro R D, Benham-Pyle B, Bimi L, Edoh D, Bosompem K, Wilson M, Cappello M. 2011. Epidemiology of hookworm infection in Kintampo North Municipality, Ghana: patterns of malaria coinfection, anemia, and albendazole treatment failure. Am. J. Trop. Med. Hyg. 84:792-800.
8. Soukhathammavong P A, Sayasone S, Phongluxa K, Xayaseng V, Utzinger J, Vounatsou P, Hatz C, Akkhavong K, Keiser J, Odermatt P. 2012. Low efficacy of single-dose albendazole and mebendazole against hookworm and effect on concomitant helminth infection in Lao P D R. PLoS Negl. Trop. Dis. 6:e1417. doi:10.1371/journal.pntd.0001417.
9. Stothard J R, Rollinson D, Imison E, Khamis I S. 2009. A spot-check of the efficacies of albendazole or levamisole, against soil-transmitted helminthiases in young Ungujan children, reveals low frequencies of cure. Ann. Trop. Med. Parasitol. 103:357-360.
10. Geary T G, Woo K, McCarthy J S, Mackenzie C D, Horton J, Prichard R K, de Silva N R, Olliaro P L, Lazdins-Helds J K, Engels D A, Bundy D A. 2010. Unresolved issues in anthelmintic pharmacology for helminthiases of humans. Int. J. Parasitol. 40:1-13.
11. Holden-Dye L, Walker R J. 2007. Anthelmintic drugs. WormBook 2007: 1-13.
12. Cappello M, Bungiro R D, Harrison L M, Bischof L J, Griffitts J S, Barrows B D, Aroian R V. 2006. A purified *Bacillus thuringiensis* crystal protein with therapeutic activity against the hookworm parasite *Ancylostoma ceylanicum*. Proc. Natl. Acad. Sci. U.S.A 103:15154-15159.
13. Hu Y, Georghiou S B, Kelleher A J, Aroian R V. 2010. *Bacillus thuringiensis* Cry5B protein is highly efficacious as a single-dose therapy against an intestinal roundworm infection in mice. PLoS Negl. Trop. Dis. 4:e614. doi: 10.1371/journal.pntd.0000614.
14. Hu Y, Zhan B, Keegan B, Yiu Y Y, Miller M M, Jones K, Aroian R V. 2012. Mechanistic and single-dose in vivo therapeutic studies of Cry5B anthelmintic action against hookworms. PLoS Negl. Trop. Dis. 6:e1900. doi:10.1371/journal.pntd.0001900.
15. Cutting S M. 2011. *Bacillus* probiotics. Food Microbiol. 28:214-220.
16. Casula G, Cutting S M. 2002. *Bacillus* probiotics: spore germination in the gastrointestinal tract. Appl. Environ. Microbiol. 68:2344-2352.
17. Duc L H, Hong H A, Barbosa T M, Henriques A O, Cutting S M. 2004. Characterization of *Bacillus* probiotics available for human use. Appl. Environ. Microbiol. 70:2161-2171.
18. Hoa N T, Baccigalupi L, Huxham A, Smertenko A, Van P H, Ammendola S, Ricca E, Cutting A S. 2000. Characterization of *Bacillus* species used for oral bacteriotherapy and bacterioprophylaxis of gastrointestinal disorders. Appl. Environ. Microbiol. 66:5241-5247.
19. Hoa T T, Duc L H, Isticato R, Baccigalupi L, Ricca E, Van P H, Cutting S M. 2001. Fate and dissemination of *Bacillus subtilis* spores in a murine model. Appl. Environ. Microbiol. 67:3819-3823.
20. Hong H A, Huang J M, Khaneja R, Hiep L V, Urdaci M C, Cutting S M. 2008. The safety of *Bacillus subtilis* and *Bacillus indicus* as food probiotics. J. Appl. Microbiol. 105:510-520.
21. D'Arienzo R, Maurano F, Mazzarella G, Luongo D, Stefanile R, Ricca E, Rossi M. 2006. *Bacillus subtilis* spores reduce susceptibility to *Citrobacter rodentium*-mediated enteropathy in a mouse model. Res. Microbiol. 157: 891-897.
22. Duc L H, Hong H A, Fairweather N, Ricca E, Cutting S M. 2003. Bacterial spores as vaccine vehicles. Infect. Immun. 71:2810-2818.
23. Hoang T H, Hong H A, Clark G C, Titball R W, Cutting S M. 2008. Recombinant *Bacillus subtilis* expressing the *Clostridium perfringens* alpha toxoid is a candidate orally delivered vaccine against necrotic enteritis. Infect. Immun. 76:5257-5265.

24. La Ragione R M, Casula G, Cutting S M, Woodward M J. 2001. *Bacillus subtilis* spores competitively exclude *Escherichia coli* O78:K80 in poultry. Vet. Microbiol. 79:133-142.
25. La Ragione R M, Woodward M J. 2003. Competitive exclusion by *Bacillus subtilis* spores of *Salmonella enterica* serotype *Enteritidis* and *Clostridium perfringens* in young chickens. Vet. Microbiol. 94:245-256.
26. Permpoonpattana P, Hong H A, Phetcharaburanin J, Huang J M, Cook J, Fairweather N F, Cutting S M. 2011. Immunization with *Bacillus* spores expressing toxin A peptide repeats protects against infection with *Clostridium difficile* strains producing toxins A and B. Infect. Immun. 79: 2295-2302.
27. Song M, Hong H A, Huang J M, Colenutt C, Khang D D, Nguyen T V, Park S M, Shim B S, Song H H, Cheon I S, Jang J E, Choi J A, Choi Y K, Stadler K, Cutting S M. 2012. Killed *Bacillus subtilis* spores as a mucosal adjuvant for an H5N1 vaccine. Vaccine 30:3266-3277.
28. Conlan J V, Khamlome B, Vongxay K, Elliot A, Pallant L, Sripa B, Blacksell S D, Fenwick S, Thompson R C. 2012. Soil-transmitted helminthiasis in Laos: a community-wide cross-sectional study of humans and dogs in a mass drug administration environment. Am. J. Trop. Med. Hyg. 86:624-634.
29. Marroquin L D, Elyassnia D, Griffitts J S, Feitelson J S, Aroian R V. 2000. *Bacillus thuringiensis* (Bt) toxin susceptibility and isolation of resistance mutants in the nematode *Caenorhabditis elegans*. Genetics 155:1693-1699.
30. Dubnau D, Davidoff-Abelson R. 1971. Fate of transforming DNA following uptake by competent *Bacillus subtilis*. I. Formation and properties of the donor-recipient complex. J. Mol. Biol. 56:209-221.
31. Sierro N, Makita Y, de Hoon M, Nakai K. 2008. DBTBS: a database of transcriptional regulation in *Bacillus subtilis* containing upstream intergenic conservation information. Nucleic Acids Res. 36:D93-D96.
32. Shevchenko A, Wilm M, Vorm O, Mann M. 1996. Mass spectrometric sequencing of proteins silver-stained polyacrylamide gels. Anal. Chem. 68:850-858.
33. National Research Council. 1996. Guide for the care and use of laboratory animals. National Academies Press, Washington, D C.
34. Hu Y, Xiao S H, Aroian R V. 2009. The new anthelmintic tribendimidine is an L-type (levamisole and pyrantel) nicotinic acetylcholine receptor agonist. PLoS Negl. Trop. Dis. 3:e499. doi:10.1371/journal.pntd.0000499.
35. Hu Y, Platzer E G, Bellier A, Aroian R V. 2010. Discovery of a highly synergistic anthelmintic combination that shows mutual hypersusceptibility. Proc. Natl. Acad. Sci. U.S.A 107:5955-5960.
36. Lereclus D, Arantes O, Chaufaux J, Lecadet M. 1989. Transformation and expression of a cloned delta-endotoxin gene in *Bacillus thuringiensis*. FEMS Microbiol. Lett. 51:211-217.
37. Yang Y, Qi Y, Huang Y. 1996. Cloning and expression of full-length delta-endotoxin cryIA(c) gene in three kinds of prokaryotic systems using shuttle vector pHT3101. Wei Sheng Wu Xue Bao 36:173-180.
38. Youngman P, Perkins J B, Losick R. 1984. Construction of a cloning site near one end of Tn917 into which foreign DNA may be inserted without affecting transposition in *Bacillus subtilis* or expression of the transposonborne erm gene. Plasmid 12:1-9.
39. Cannon R J C. 1996. *Bacillus thuringiensis* use in agriculture: a molecular perspective. Biol. Rep. 71:561-636.
40. Hu Y, Aroian R V. 2012. Promise of *Bacillus thuringiensis* crystal proteins as anthelmintics, p 267-281. In Caffrey C R (ed), Parasitic helminths: targets, screens, drugs, and vaccines. Wiley-VCH Verlag Gmh & Co, KGaA, Weinheim, Germany.
41. Bischof L J, Huffman D L, Aroian R V. 2006. Assays for toxicity studies in *C. elegans* with Bt crystal proteins. Methods Mol. Biol. 351:139-154.
42. Kho M F, Bellier A, Balasubramani V, Hu Y, Hsu W, Nielsen-LeRoux C, McGillivray S M, Nizet V, Aroian R V. 2011. The pore-forming protein Cry5B elicits the pathogenicity of *Bacillus* sp. against *Caenorhabditis elegans*. PLoS One 6:e29122. doi:10.1371/journal.pone.0029122.
43. Baum J A, Malvar T. 1995. Regulation of insecticidal crystal protein production in *Bacillus thuringiensis*. Mol. Microbiol. 18:1-12.
44. Buasri W, Panbangred W. 2012. Large crystal toxin formation in chromosomally engineered *Bacillus thuringiensis* subsp. *aizawai* due to sigmaE accumulation. Appl. Environ. Microbiol. 78:1682-1691.
45. Brans A, Filee P, Chevigne A, Claessens A, Joris B. 2004. New integrative method to generate *Bacillus subtilis* recombinant strains free of selection markers. Appl. Environ. Microbiol. 70:7241-7250.
46. Tritten L, Nwosu U, Vargas M, Keiser J. 2012. In vitro and in vivo efficacy of tribendimidine and its metabolites alone and in combination against the hookworms *Heligmosomoides bakeri* and *Ancylostoma ceylanicum*. Acta Trop. 122:101-107.
47. Tritten L, Silbereisen A, Keiser J. 2011. In vitro and in vivo efficacy of monepantel (AAD 1566) against laboratory models of human intestinal nematode infections. PLoS Negl. Trop. Dis. 5:e1457. doi:10.1371/journal.pntd.0001457.
48. Griffitts J S, Aroian R V. 2005. Many roads to resistance: how invertebrates adapt to Bt toxins. Bioessays 27:614-624.
49. Griffitts J S, Haslam S M, Yang T, Garczynski S F, Mulloy B, Morris H, Cremer P S, Dell A, Adang M J, Aroian R V. 2005. Glycolipids as receptors for *Bacillus thuringiensis* crystal toxin. Science 307:922-925.
50. Los F C, Kao C Y, Smitham J, McDonald K L, Ha C, Peixoto C A, Aroian R V. 2011. RAB-5- and RAB-11-dependent vesicle-trafficking pathways are required for plasma membrane repair after attack by bacterial pore-forming toxin. Cell Host Microbe 9:147-157.
51. Wang F, Liu Y, Zhang F, Chai L, Ruan L, Peng D, Sun M. 2012. Improvement of crystal solubility and increasing toxicity against *Caenorhabditis elegans* by asparagine substitution in block 3 of *Bacillus thuringiensis* crystal protein Cry5Ba. Appl. Environ. Microbiol. 78:7197-7204.

52. el-Bendary M A. 2006. *Bacillus thuringiensis* and *Bacillus sphaericus* biopesticides production. J. Basic Microbiol. 46:158-170.

53. Schallmey M, Singh A, Ward O P. 2004. Developments in the use of *Bacillus* species for industrial production. Can. J. Microbiol. 50:1-17.

Example 15

Bioactivity of Compositions Comprising Cry5b and Probiotic Bacteria

This example describes additional data that were obtained using the above-described bioassays for anthelmintic activity.

FIG. 13 shows results from an in vivo bioassay of intestinal worm burdens in golden Syrian hamsters infected with *Ancylostoma ceylanicum* hookworms as described by Hu et al. (2012 *PLoS Negl. Trop. Dis.* 6:e1900. doi:10.137/journal.pntd.0001900). The four groups (in black, n=7 per group) shown are the intestinal worm burdens from the groups of infected hamsters treated with purified full-length *B. thuringiensis* Cry5B protein (prepared according to Griffitts et al., 2001 *Science* 293:860; for sequence see FIG. 2) at a single dose of 1 mg (solid circles, 10 mg/kg), 3 mg (solid upright triangles, 30 mg/kg), or 10 mg (solid inverted triangles, 100 mg/kg) (715 nmoles/kg), or with placebo (solid squares, ddH$_2$O), respectively. The treatments were conducted on day 16 P.I. and intestinal worm burdens assessed on day 21 P.I. The worm burdens in each hamster are indicated with a separate symbol. Long horizontal bars represent mean worm burdens; smaller bars indicate SEM (standard error of the mean).

Figure 14:
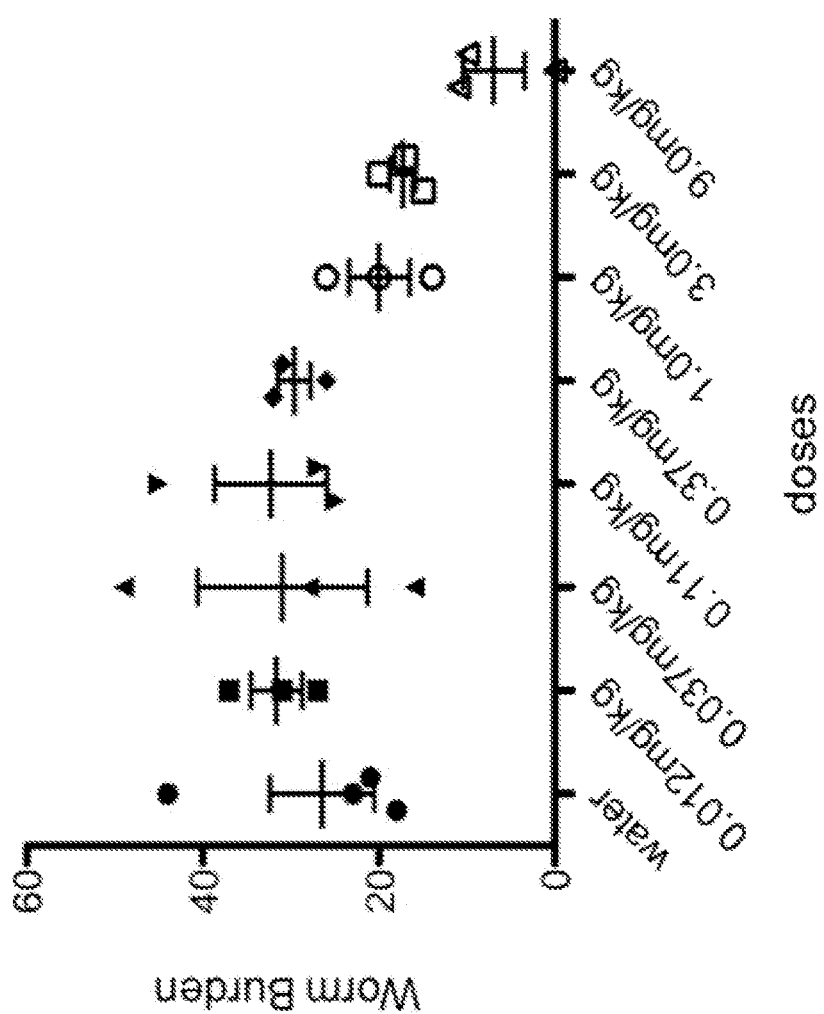
FIG. 14 shows dose-response results for indicated dosages of unfractionated Cry5B-containing spore-crystal lysates (SCL) in the in vivo bioassay of intestinal worm burdens in golden Syrian hamsters infected with *Ancylostoma ceylanicum* hookworms. The assay was performed according to Hu et al. (2012 *PLoS Negl. Trop. Dis.* 6:e1900. doi:10.137/journal.pntd.0001900) except instead of purified Cry5B protein the animals received the indicated dosages, via gavage, of Cry5B spore-crystal lysates obtained from cultured *Bacillus thuringiensis* cells that were transformed with a low copy plasmid that expressed *B. thuringiensis* Cry5B and then grown to sporulation phase, at which point the cells lysed releasing spores, crystals, and bacterial lysate (spore crystal lysate, SCL). The amounts of Cry5B gavaged were determined by taking known volumes of spore crystal lysates, resolving full length Cry5B protein by SDS PAGE, and quantitating the amount of protein in the Cry5B band relative to known amounts of bovine serum albumin (BSA) standards on the gel.

FIG. 14 shows dose-response results for indicated dosages of unfractionated Cry5B-containing spore-crystal lysates (SCL) in the in vivo bioassay of intestinal worm burdens in golden Syrian hamsters infected with *Ancylostoma ceylanicum* hookworms. The assay was performed according to Hu et al. (2012 *PLoS Negl. Trop. Dis.* 6:e1900. doi:10.137/journal.pntd.0001900) except instead of purified Cry5B protein the animals received the indicated dosages, via gavage, of Cry5B spore-crystal lysates obtained from cultured *Bacillus thuringiensis* cells that were transformed with a low copy plasmid that expressed *B. thuringiensis* Cry5B and then grown to sporulation phase. The amounts of Cry5B gavaged were determined by taking known volumes of spore crystal lysates, resolving full length Cry5B protein by SDS PAGE, and quantitating the amount of protein in the Cry5B band relative to known amounts of bovine serum albumin (BSA) standards on the gel.

Figure 15:
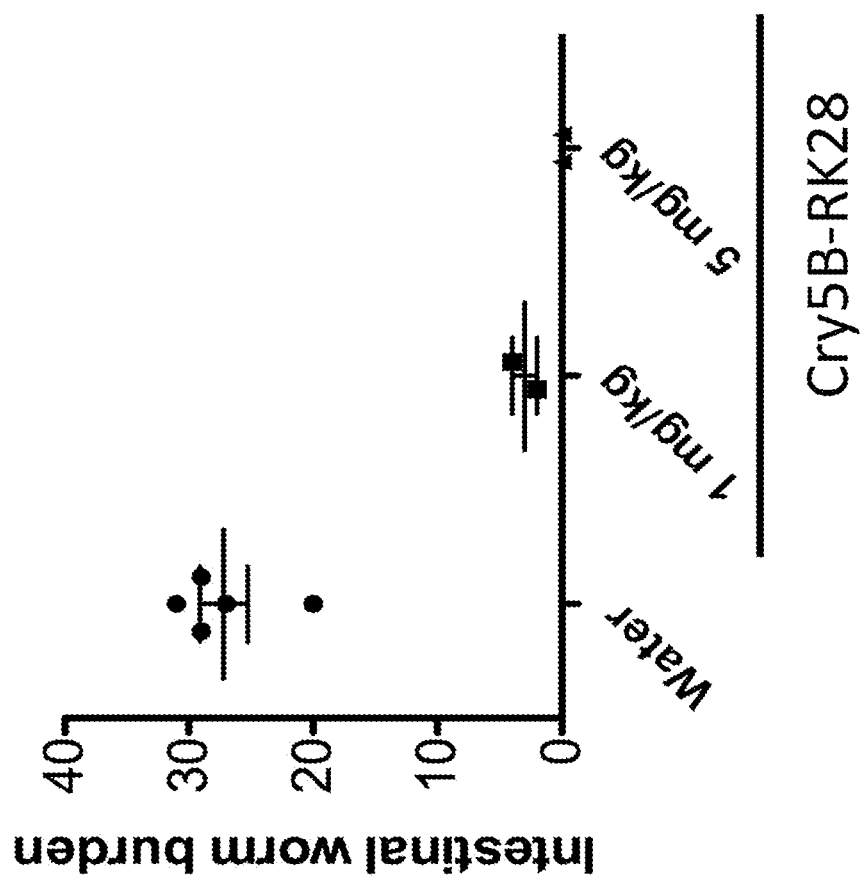
FIG. 15 shows results from the in vivo bioassay of intestinal worm burdens in golden Syrian hamsters infected with *Ancylostoma ceylanicum* hookworms (Hu et al., 2012 *PLoS Negl. Trop. Dis.* 6:e1900. doi:10.137/journal.pntd.0001900) following treatment with two different dosages of Cry5B spore-crystal lysates obtained from cultured *Bacillus thuringiensis* natto cells that were transformed with a low copy plasmid that expressed *B. thuringiensis* Cry5B and then grown to sporulation phase.

FIG. 15 shows results from the in vivo bioassay of intestinal worm burdens in golden Syrian hamsters infected with *Ancylostoma ceylanicum* hookworms (Hu et al., 2012 *PLoS Negl. Trop. Dis.* 6:e1900. doi:10.137/journal.pntd.0001900) following treatment with two different dosages of Cry5B spore-crystal lysates obtained from cultured *Bacillus thuringiensis* natto cells that were transformed with a low copy plasmid that expressed *B. thuringiensis* Cry5B and then grown to sporulation phase. *B. subtilis natto* was transformed with the same Cry5B expressing plasmid described in Example 14 (Hu et al. *Appl. Environ. Microbiol.* 2013, 79(18):5527). Because *B. subtilis natto* is not naturally competent, *B. subtilis natto* cells were made competent by artificially introducing the ComK competency plasmid into the *B. subtilis natto* strain via protoplast transformation (Ashikaga et al., *J Bacteriol.* 2000; 182(9):2411-5; Romero, D., et al *J Microbiol Meth.* 2006; 66(3):556-9). The resultant strain was able to take up any DNA and the ComK plasmid, being unstable, was readily lost by growing under non-selective pressure).

Figure 11:
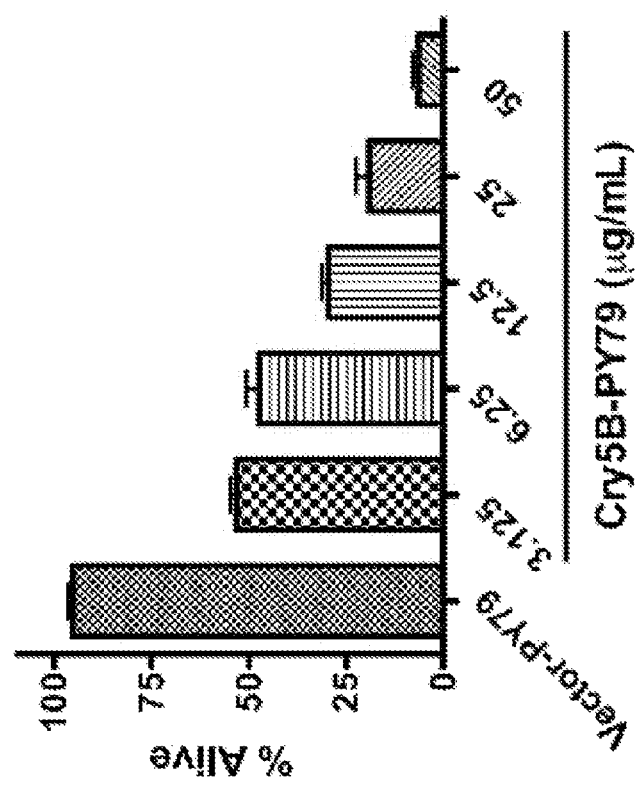
FIG. 11 depicts PY79-Cry5B bioactivity in vitro against *C. elegans*. The results shown are from dose-dependent mortality assays plotting % live *C. elegans* (y axis) versus Cry5B concentration (x axis). The PY79-vector strain (vector-PY79) lacked Cry5B (0 µg/ml). Each data point represents the average for three independent experiments with ~75 to 90 *C. elegans* organisms per experiment (~225 to 270 organisms per data point). Error bars represent standard errors.
Figure 12:
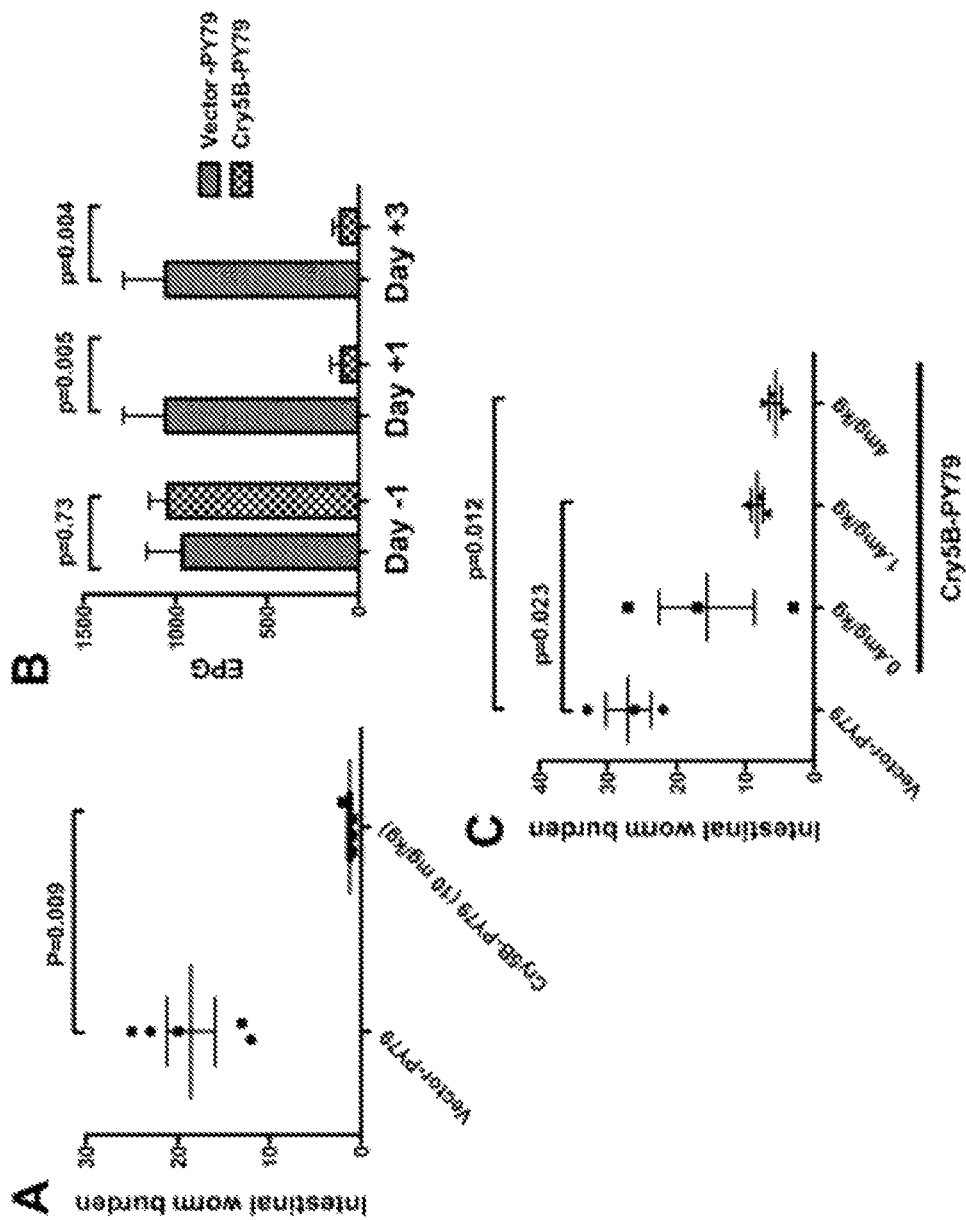
FIG. 12 (FIGS. 12A-12C) shows that PY79-Cry5B had a dose-dependent therapeutic effect against hookworm infection in hamsters. (A) Intestinal hookworm burdens in nine hamsters following treatment with PY79-vector or PY79-Cry5B (10 mg/kg Cry5B) (error bars in all panels show standard errors). The average worm burdens were 18.6±2.6 and 1.3±0.3 for PY79-vector and PY79-Cry5B, respectively. (B) Fecal egg counts on day−1, day+1, and day+3 relative to the day of treatment. The actual egg counts for PY79-vector and PY79-Cry5B were 965±193 and 1,044±99, respectively, on day−1, 1,055±230 and 94±60, respectively, on day+1, and 1,055±227 and 100±42, respectively, on day+3. EPG, eggs per gram of feces. (C) In vivo dose-response experiment with 12 hamsters. The average worm burdens for PY79-vector and PY79-Cry5B at Cry5B concentrations of 0.4 mg/kg, 1.4 mg/kg, and 4 mg/kg were 27.0±3.2, 15.7±7.0, 8.3±0.9, and 5.7±0.9, respectively.

FIG. 16 shows data obtained in vitro using the *C. elegans* mortality assay described in FIG. 11 to evaluate the effects on *C. elegans* of purified Cry5B protein (prepared according to Griffitts et al., 2001 *Science* 293:860; for sequence see FIG. 2) when combined in a mixture either with sporulated *B. thuringiensis* HD1 or with sporulated *B. subtilis* PY79. For each data point, the number of spores (HD1 or PY79) was held constant and the quantity of Cry5B was titrated (x-axis).

Figure 17:
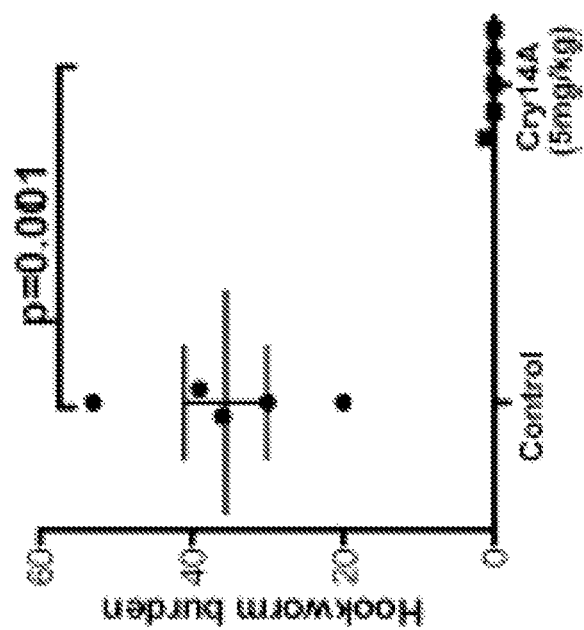
FIG. 17 shows the effects of Cry14A on an in vivo bioassay of intestinal worm burdens in golden Syrian hamsters infected with *Ancylostoma ceylanicum* hookworms.

FIG. 17 shows results from the in vivo bioassay of intestinal worm burdens in golden Syrian hamsters infected with *Ancylostoma ceylanicum* hookworms (Hu et al., 2012 *PLoS Negl. Trop. Dis.* 6:e1900. doi:10.137/journal.pntd.0001900) following treatment (5 mg/kg) by gavage on day 18 P.I. with either *B. thuringiensis* strain HD1 spore lysates transformed with empty vector ("control", spore lysates from the acrystaliferous mutant *B. thuringiensis* strain HD1, which does not produce any Cry proteins) or spore crystal lysates from *B. thuringiensis* strain HD1 that has been engineered to express Cry14A (for sequence see FIG. 4) using a plasmid encoding Cry14A under the control of the operably linked Cry3A promoter. Hookworm burdens were assessed on day 20 post-infection (P.I.).

Example 16

Gene Replacement and Generation of a *Bacillus Subtilis* Auxotroph cry5B gene was integrated into the *B. subtilis* genome by a strategy that simultaneously deleted the chromosomal thyA gene, which encodes thymidylate synthetase. A cry5B cassette, flanked by the upstream and downstream regions of *B. subtilis* thyA, was assembled in vitro by standard PCR techniques. *B. subtilis natto* was transformed with this construct in a single step. Transformants simultaneously acquired two properties: auxotrophy for thymine nucleotides and the production of Cry5B protein. Because thymine auxotrophs in *B. subtilis* are known to be naturally resistant to trimethoprim and other antifolate compounds, selection for growth in the presence of trimethoprim plus thymine selected for the desired integration event without the introduction of an antibiotic resistance marker. The construct contained no foreign DNA at all except for the cry5B gene itself. The auxotroph permitted easy replication under laboratory conditions but the strain was environmentally dead and unable to replicate in the wild (e.g., following defecation by a human).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating or reducing severity or likelihood of occurrence of a parasitic worm or helminth infection in a subject, the method comprising:
   administering to the subject a therapeutically effective amount of a composition comprising a recombinant bacterium that expresses a crystal protein.

2. The method of claim 1, wherein the crystal protein is selected from the group consisting of Cry5B, Cry21A, Cry14A, Cry13A, and Cry6A.

3. The method of claim 1, wherein the recombinant bacterium is a Gram-positive bacterium.

4. The method of claim 1, wherein the recombinant bacterium is a Gram-negative bacterium.

5. The method of claim 1, wherein the recombinant bacterium is a lactic acid fermenting bacterium.

6. The method of claim 5, wherein the lactic acid fermenting bacterium is a *Lactobacillus* species selected from the group consisting of *Lactobacillus acidophilus, Lactobacillus gasseri, Lactobacillus johnsonii,* and *Lactobacillus reuteri.*

7. The method of claim 1, wherein the recombinant bacterium is administered in combination with at least one additional therapeutic agent.

8. The method of claim 7, wherein the at least one additional therapeutic agent is a nicotinic acetylcholine receptor agonist.

9. The method of claim 8, wherein the at least one additional therapeutic agent is administered simultaneously with the therapeutically effective amount of the recombinant bacterium expressing the crystal protein.

10. The method of claim 8, wherein the at least one additional therapeutic agent is administered sequentially with the therapeutically effective amount of the recombinant bacterium expressing the crystal protein.

11. The method of claim 8, wherein the nicotinic acetylcholine receptor agonist is from the levamisole family of nicotinic acetylcholine receptor agonists.

12. The method of claim 8, wherein the nicotinic acetylcholine receptor agonist is pyrantel or tribendimidine.

13. The method of claim 1, wherein the parasitic worm or helminth infection is caused by a parasitic worm or helminth selected from the group consisting of Roundworm, Whipworm, Hookworm, *Ascaris, Pinworm, Strongyloides,* Schistosome, and Trematodes.

14. The method of claim 1, wherein the parasitic worm or helminth infection is caused by a parasitic worm or helminth selected from the group consisting of hookworm *Ancylostoma duodenale,* hookworm *Necator americanus,* whipworm *Trichuris trichiura,* roundworm *Ascaris lumbricoides,* threadworm *Strongyloides stercoralis,* and pinworm *Enterobius vermiculari.*

15. The method of claim 1, wherein the subject is a mammal selected from the group consisting of human being, feline, rodent, canine, bovine, equine, swine, caprine, ovine, and primate.

16. The method of claim 1, wherein the crystal protein is a truncated crystal protein.

17. The method of claim 1, wherein the crystal protein is a variant crystal protein.

18. The method of claim 1, wherein the crystal protein is Cry5B and wherein the Cry5B includes at least amino acids 30 through 693 of SEQ ID NO:1.

19. The method of claim 1, wherein the crystal protein is Cry13A and wherein the Cry13A includes at least amino acids 30 through 688 of SEQ ID NO:2.

20. The method of claim 1, wherein the crystal protein is Cry14A and wherein the Cry14A includes at least amino acids 30 through 675 of SEQ ID NO:3.

21. The method of claim 7, wherein the at least one additional therapeutic agent is a therapeutically effective amount of a second recombinant bacterium that expresses or is capable of expressing a second crystal protein.

22. The method of claim 21, wherein the first and second recombinant bacteria are Gram-positive bacteria.

23. The method of claim 21, wherein the first and second recombinant bacteria are Gram-negative bacteria.

24. The method of claim 21, wherein the first and second crystal proteins are different crystal proteins.

25. The method of claim 21, wherein the first and second crystal proteins are independently selected from the group consisting of Cry5B, Cry21A, Cry14A, Cry13A, and Cry6A.

26. The method of claim 21, wherein the bacterium is a lactic acid fermenting bacterium.

27. The method of claim 26, wherein the lactic acid fermenting bacterium is a *Lactobacillus* species selected from the group consisting of *Lactobacillus acidophilus, Lactobacillus gasseri, Lactobacillus johnsonii,* and *Lactobacillus reuteri.*

28. The method of claim 1 wherein the bacterium is selected from the group consisting of *B. subtilis, B. subtilis* PY79, *B. subtilis natto, B. cereus, B. cereus* var. *Toyoi*

(*Toyocerin*), *B. cereus* var. *toyoii, B. toyonensis, Lactobacillus rhamnosus, Lactobacillus casei*, and *Lactococcus lactis*.

29. The method of claim 21 wherein each of the first and second recombinant bacterium is independently selected from the group consisting of *B. subtilis, B. subtilis* PY79, *B. subtilis natto, B. cereus, B. cereus* var. *Toyoi* (*Toyocerin*), *B. cereus* var. *toyoii, B. toyonensis, Lactobacillus rhamnosus, Lactobacillus casei*, and *Lactococcus lactis*.

* * * * *

SEQUENCE LISTING

```
<160> NUMBER OF SEQ ID NOS: 34

<210> SEQ ID NO 1
<211> LENGTH: 1245
<212> TYPE: PRT
<213> ORGANISM: Bacillus thuringiensis
<220> FEATURE:
<223> OTHER INFORMATION: pesticidal crystal (Cry)

<400> SEQUENCE: 1

Met Ala Thr Ile Asn Glu Leu Tyr Pro Val Pro Tyr Asn Val Leu Ala
1               5                   10                  15

His Pro Ile Lys Glu Val Asp Asp Pro Tyr Ser Trp Ser Asn Leu Leu
            20                  25                  30

Lys Gly Ile Gln Glu Gly Trp Glu Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60

Gly Lys Leu Asp Tyr Phe Ala Leu Thr Lys Ala Ser Ile Ser Leu Ile
65                  70                  75                  80

Gly Phe Ile Pro Gly Ala Glu Ala Ala Val Pro Phe Ile Asn Met Phe
                85                  90                  95

Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
        115                 120                 125

Asp Asn Lys Phe Leu Ser Tyr Asn Leu Ser Thr Leu Asn Lys Thr Ile
    130                 135                 140

Glu Gly Leu Gln Gly Asn Leu Gly Leu Phe Gln Asn Ala Ile Gln Val
145                 150                 155                 160

Ala Ile Cys Gln Gly Ser Thr Pro Glu Arg Val Asn Phe Asp Gln Asn
                165                 170                 175

Cys Thr Pro Cys Asn Pro Asn Gln Pro Cys Lys Asp Asp Leu Asp Arg
            180                 185                 190

Val Ala Ser Arg Phe Asp Thr Ala Asn Ser Gln Phe Thr Gln His Leu
        195                 200                 205

Pro Glu Phe Lys Asn Pro Trp Ser Asp Glu Asn Ser Thr Gln Glu Phe
    210                 215                 220

Lys Arg Thr Ser Val Glu Leu Thr Leu Pro Met Tyr Thr Thr Val Ala
225                 230                 235                 240

Thr Leu His Leu Leu Leu Tyr Glu Gly Tyr Ile Glu Phe Met Thr Lys
                245                 250                 255

Trp Asn Phe His Asn Glu Gln Tyr Leu Asn Asn Leu Lys Val Glu Leu
            260                 265                 270

Gln Gln Leu Ile His Ser Tyr Ser Glu Thr Val Arg Thr Ser Phe Leu
        275                 280                 285

Gln Phe Leu Pro Thr Leu Asn Asn Arg Ser Lys Ser Ser Val Asn Ala
    290                 295                 300

Tyr Asn Arg Tyr Val Arg Asn Met Thr Val Asn Cys Leu Asp Ile Ala
305                 310                 315                 320

Ala Thr Trp Pro Thr Phe Asp Thr His Asn Tyr His Gln Gly Gly Lys
                325                 330                 335

Leu Asp Leu Thr Arg Ile Ile Leu Ser Asp Thr Ala Gly Pro Ile Glu
            340                 345                 350

Glu Tyr Thr Thr Gly Asp Lys Thr Ser Gly Pro Glu His Ser Asn Ile
```

```
            355                 360                 365
Thr Pro Asn Asn Ile Leu Asp Thr Pro Ser Pro Thr Tyr Gln His Ser
370                 375                 380

Phe Val Ser Val Asp Ser Ile Val Tyr Ser Arg Lys Glu Leu Gln Gln
385                 390                 395                 400

Leu Asp Ile Ala Thr Tyr Ser Thr Asn Ser Asn Asn Cys His Pro
            405                 410                 415

Tyr Gly Leu Arg Leu Ser Tyr Thr Asp Gly Ser Arg Tyr Asp Tyr Gly
            420                 425                 430

Asp Asn Gln Pro Asp Phe Thr Thr Ser Asn Asn Asn Tyr Cys His Asn
            435                 440                 445

Ser Tyr Thr Ala Pro Ile Thr Leu Val Asn Ala Arg His Leu Tyr Asn
            450                 455                 460

Ala Lys Gly Ser Leu Gln Asn Val Glu Ser Leu Val Val Ser Thr Val
465                 470                 475                 480

Asn Gly Gly Ser Gly Ser Cys Ile Cys Asp Ala Trp Ile Asn Tyr Leu
            485                 490                 495

Arg Pro Pro Gln Thr Ser Lys Asn Glu Ser Arg Pro Asp Gln Lys Ile
            500                 505                 510

Asn Val Leu Tyr Pro Ile Thr Glu Thr Val Asn Lys Gly Thr Gly Gly
            515                 520                 525

Asn Leu Gly Val Ile Ser Ala Tyr Val Pro Met Glu Leu Val Pro Glu
530                 535                 540

Asn Val Ile Gly Asp Val Asn Ala Asp Thr Lys Leu Pro Leu Thr Gln
545                 550                 555                 560

Leu Lys Gly Phe Pro Phe Glu Lys Tyr Gly Ser Glu Tyr Asn Asn Arg
            565                 570                 575

Gly Ile Ser Leu Val Arg Glu Trp Ile Asn Gly Asn Asn Ala Val Lys
            580                 585                 590

Leu Ser Asn Ser Gln Ser Val Gly Ile Gln Ile Thr Asn Gln Thr Lys
            595                 600                 605

Gln Lys Tyr Glu Ile Arg Cys Arg Tyr Ala Ser Lys Gly Asp Asn Asn
            610                 615                 620

Val Tyr Phe Asn Val Asp Leu Ser Glu Asn Pro Phe Arg Asn Ser Ile
625                 630                 635                 640

Ser Phe Gly Ser Thr Glu Ser Ser Val Val Gly Val Gln Gly Glu Asn
            645                 650                 655

Gly Lys Tyr Ile Leu Lys Ser Ile Thr Thr Val Glu Ile Pro Ala Gly
            660                 665                 670

Ser Phe Tyr Val His Ile Thr Asn Gln Gly Ser Ser Asp Leu Phe Leu
            675                 680                 685

Asp Arg Ile Glu Phe Val Pro Lys Ile Gln Phe Gln Phe Cys Asp Asn
            690                 695                 700

Asn Asn Leu His Cys Asp Cys Asn Asn Pro Val Asp Thr Asp Cys Thr
            705                 710                 715                 720

Phe Cys Cys Val Cys Thr Ser Leu Thr Asp Cys Asp Cys Asn Asn Pro
                        725                 730                 735

Arg Gly Leu Asp Cys Thr Leu Cys Cys Gln Val Glu Asn Gln Leu Pro
            740                 745                 750

Ser Phe Val Thr Leu Thr Asp Leu Gln Asn Ile Thr Thr Gln Val Asn
            755                 760                 765

Ala Leu Val Ala Ser Ser Glu His Asp Thr Leu Ala Thr Asp Val Ser
770                 775                 780
```

```
Asp Tyr Glu Ile Glu Glu Val Val Leu Lys Val Asp Ala Leu Ser Gly
785                 790                 795                 800

Glu Val Phe Gly Lys Glu Lys Lys Ala Leu Arg Lys Leu Val Asn His
            805                 810                 815

Thr Lys Arg Leu Ser Lys Ala Arg Asn Leu Leu Ile Gly Gly Asn Phe
        820                 825                 830

Asp Asn Leu Asp Ala Trp Tyr Arg Gly Arg Asn Val Val Asn Val Ser
    835                 840                 845

Asp His Glu Leu Phe Lys Ser Asp His Val Leu Leu Pro Pro Pro Thr
850                 855                 860

Leu Tyr Ser Ser Tyr Met Phe Gln Lys Val Gly Glu Ser Lys Leu Lys
865                 870                 875                 880

Ala Asn Thr Arg Tyr Thr Val Ser Gly Phe Ile Ala His Ala Glu Asp
                885                 890                 895

Leu Glu Ile Val Val Ser Arg Tyr Gly Gln Glu Val Lys Lys Val Val
                900                 905                 910

Gln Val Pro Tyr Gly Glu Ala Phe Pro Leu Thr Ser Arg Gly Ala Ile
            915                 920                 925

Cys Cys Pro Pro Arg Ser Thr Ser Asn Gly Lys Pro Ala Asp Pro His
930                 935                 940

Phe Phe Ser Tyr Ser Ile Asp Val Gly Thr Leu Asp Val Glu Ala Asn
945                 950                 955                 960

Pro Gly Ile Glu Leu Gly Leu Arg Ile Val Glu Arg Thr Gly Met Ala
                965                 970                 975

Arg Val Ser Asn Leu Glu Ile Arg Glu Asp Arg Pro Leu Lys Lys Asn
                980                 985                 990

Glu Leu Arg Asn Val Gln Arg Ala  Ala Arg Asn Trp Arg  Thr Ala Tyr
            995                 1000                1005

Asp Gln  Glu Arg Ala Glu Val  Thr Ala Leu Ile Gln  Pro Val Leu
    1010                1015                1020

Asn Gln  Ile Asn Ala Leu Tyr  Glu Asn Glu Asp Trp  Asn Gly Ala
    1025                1030                1035

Ile Arg  Ser Gly Val Ser Tyr  His Asp Leu Glu Ala  Ile Val Leu
    1040                1045                1050

Pro Thr  Leu Pro Lys Leu Asn  His Trp Phe Met Ser  Asp Met Leu
    1055                1060                1065

Gly Glu  Gln Gly Ser Ile Leu  Ala Gln Phe Gln Glu  Ala Leu Asp
    1070                1075                1080

Arg Ala  Tyr Thr Gln Leu Glu  Glu Ser Thr Ile Leu  His Asn Gly
    1085                1090                1095

His Phe  Thr Thr Asp Ala Ala  Asn Trp Thr Ile Glu  Gly Asp Ala
    1100                1105                1110

His His  Ala Ile Leu Glu Asp  Gly Arg Arg Val Leu  Arg Leu Pro
    1115                1120                1125

Asp Trp  Ser Ser Ser Val Ser  Gln Thr Ile Glu Ile  Glu Asn Phe
    1130                1135                1140

Asp Pro  Asp Lys Glu Tyr Gln  Leu Val Phe His Ala  Gln Gly Glu
    1145                1150                1155

Gly Thr  Val Ser Leu Gln His  Gly Glu Glu Gly Glu  Tyr Val Glu
    1160                1165                1170

Thr His  Pro His Lys Ser Ala  Asn Phe Thr Thr Ser  His Arg Gln
    1175                1180                1185
```

-continued

Gly Val Thr Phe Glu Thr Asn Lys Val Thr Val Glu Ile Thr Ser
1190 1195 1200

Glu Asp Gly Glu Phe Leu Val Asp His Ile Ala Leu Val Glu Ala
1205 1210 1215

Pro Leu Pro Thr Asp Asp Gln Ser Ser Asp Gly Asn Thr Thr Ser
1220 1225 1230

Asn Thr Asn Ser Asn Thr Ser Met Asn Asn Asn Gln
1235 1240 1245

<210> SEQ ID NO 2
<211> LENGTH: 803
<212> TYPE: PRT
<213> ORGANISM: Bacillus thuringiensis
<220> FEATURE:
<223> OTHER INFORMATION: pesticidal crystal

<400> SEQUENCE: 2

Met Thr Cys Gln Leu Gln Ala Gln Pro Leu Ile Pro Tyr Asn Val Leu
1 5 10 15

Ala Gly Val Pro Thr Ser Asn Thr Gly Ser Pro Ile Gly Asn Ala Gly
20 25 30

Asn Gln Phe Asp Gln Phe Glu Gln Thr Val Lys Glu Leu Lys Glu Ala
35 40 45

Trp Glu Ala Phe Gln Lys Asn Gly Ser Phe Ser Leu Ala Ala Leu Glu
50 55 60

Lys Gly Phe Asp Ala Ala Ile Gly Gly Gly Ser Phe Asp Tyr Leu Gly
65 70 75 80

Leu Val Gln Ala Gly Leu Gly Leu Val Gly Thr Leu Gly Ala Ala Ile
85 90 95

Pro Gly Val Ser Val Ala Val Pro Leu Ile Ser Met Leu Val Gly Val
100 105 110

Phe Trp Pro Lys Gly Thr Asn Asn Gln Glu Asn Leu Ile Thr Val Ile
115 120 125

Asp Lys Glu Val Gln Arg Ile Leu Asp Glu Lys Leu Ser Asp Gln Leu
130 135 140

Ile Lys Lys Leu Asn Ala Asp Leu Asn Ala Phe Thr Asp Leu Val Thr
145 150 155 160

Arg Leu Glu Glu Val Ile Ile Asp Ala Thr Phe Glu Asn His Lys Pro
165 170 175

Val Leu Gln Val Ser Lys Ser Asn Tyr Met Lys Val Asp Ser Ala Tyr
180 185 190

Phe Ser Thr Gly Gly Ile Leu Thr Leu Gly Met Ser Asp Phe Leu Thr
195 200 205

Asp Thr Tyr Ser Lys Leu Thr Phe Pro Leu Tyr Val Leu Gly Ala Thr
210 215 220

Met Lys Leu Ser Ala Tyr His Ser Tyr Ile Gln Phe Gly Asn Thr Trp
225 230 235 240

Leu Asn Lys Val Tyr Asp Leu Ser Ser Asp Glu Gly Lys Thr Met Ser
245 250 255

Gln Ala Leu Ala Arg Ala Lys Gln His Met Arg Gln Asp Ile Ala Phe
260 265 270

Tyr Thr Ser Gln Ala Leu Asn Met Phe Thr Gly Asn Leu Pro Ser Leu
275 280 285

Ser Ser Asn Lys Tyr Ala Ile Asn Asp Tyr Asn Val Tyr Thr Arg Ala
290 295 300

-continued

Met Val Leu Asn Gly Leu Asp Ile Val Ala Thr Trp Pro Thr Leu Tyr
305                 310                 315                 320

Pro Asp Asp Tyr Ser Ser Gln Ile Lys Leu Glu Lys Thr Arg Val Ile
            325                 330                 335

Phe Ser Asp Met Val Gly Gln Ser Glu Ser Arg Asp Gly Ser Val Thr
            340                 345                 350

Ile Lys Asn Ile Phe Asp Asn Thr Asp Ser His Gln His Gly Ser Ile
            355                 360                 365

Gly Leu Asn Ser Ile Ser Tyr Phe Pro Asp Glu Leu Gln Lys Ala Gln
    370                 375                 380

Leu Arg Met Tyr Asp Tyr Asn His Lys Pro Tyr Cys Thr Asp Cys Phe
385                 390                 395                 400

Cys Trp Pro Tyr Gly Val Ile Leu Asn Tyr Asn Lys Asn Thr Phe Arg
            405                 410                 415

Tyr Gly Asp Asn Asp Pro Gly Leu Ser Gly Asp Val Gln Leu Pro Ala
            420                 425                 430

Pro Met Ser Val Val Asn Ala Gln Thr Gln Thr Ala Gln Tyr Thr Asp
            435                 440                 445

Gly Glu Asn Ile Trp Thr Asp Thr Gly Arg Ser Trp Leu Cys Thr Leu
    450                 455                 460

Arg Gly Tyr Cys Thr Thr Asn Cys Phe Pro Gly Arg Gly Cys Tyr Asn
465                 470                 475                 480

Asn Ser Thr Gly Tyr Gly Glu Ser Cys Asn Gln Ser Leu Pro Gly Gln
            485                 490                 495

Lys Ile His Ala Leu Tyr Pro Phe Thr Gln Thr Asn Val Leu Gly Gln
            500                 505                 510

Ser Gly Lys Leu Gly Leu Leu Ala Ser His Ile Pro Tyr Asp Leu Ser
    515                 520                 525

Pro Asn Asn Thr Ile Gly Asp Lys Asp Thr Asp Ser Thr Asn Ile Val
530                 535                 540

Ala Lys Gly Ile Pro Val Glu Lys Gly Tyr Ala Ser Ser Gly Gln Lys
545                 550                 555                 560

Val Glu Ile Ile Arg Glu Trp Ile Asn Gly Ala Asn Val Val Gln Leu
            565                 570                 575

Ser Pro Gly Gln Ser Trp Gly Met Asp Phe Thr Asn Ser Thr Gly Gly
            580                 585                 590

Gln Tyr Met Val Arg Cys Arg Tyr Ala Ser Thr Asn Asp Thr Pro Ile
    595                 600                 605

Phe Phe Asn Leu Val Tyr Asp Gly Gly Ser Asn Pro Ile Tyr Asn Gln
    610                 615                 620

Met Thr Phe Pro Ala Thr Lys Glu Thr Pro Ala His Asp Ser Val Asp
625                 630                 635                 640

Asn Lys Ile Leu Gly Ile Lys Gly Ile Asn Gly Asn Tyr Ser Leu Met
            645                 650                 655

Asn Val Lys Asp Ser Val Glu Leu Pro Ser Gly Lys Phe His Val Phe
            660                 665                 670

Phe Thr Asn Asn Gly Ser Ser Ala Ile Tyr Leu Asp Arg Leu Glu Phe
            675                 680                 685

Val Pro Leu Asp Gln Pro Ala Ala Pro Thr Gln Ser Thr Gln Pro Ile
            690                 695                 700

Asn Tyr Pro Ile Thr Ser Arg Leu Pro His Arg Ser Gly Glu Pro Pro
705                 710                 715                 720

Ala Ile Ile Trp Glu Lys Ser Gly Asn Val Arg Gly Asn Gln Leu Thr

-continued

```
                    725                 730                 735
Ile Ser Ala Gln Gly Val Pro Glu Asn Ser Gln Ile Tyr Leu Ser Val
                740                 745                 750

Gly Gly Asp Arg Gln Ile Leu Asp Arg Ser Asn Gly Phe Lys Leu Val
            755                 760                 765

Asn Tyr Ser Pro Thr Tyr Ser Phe Thr Asn Ile Gln Ala Ser Ser Ser
        770                 775                 780

Asn Leu Val Asp Ile Thr Ser Gly Thr Ile Thr Gly Gln Val Gln Val
785                 790                 795                 800

Ser Asn Leu

<210> SEQ ID NO 3
<211> LENGTH: 1186
<212> TYPE: PRT
<213> ORGANISM: Bacillus thuringiensis
<220> FEATURE:
<223> OTHER INFORMATION: pesticidal crystal

<400> SEQUENCE: 3

Met Asp Cys Asn Leu Gln Ser Gln Gln Asn Ile Pro Tyr Asn Val Leu
1               5                   10                  15

Ala Ile Pro Val Ser Asn Val Asn Ala Leu Val Asp Thr Ala Gly Asp
                20                  25                  30

Leu Lys Lys Ala Trp Glu Glu Phe Gln Lys Thr Gly Ser Phe Ser Leu
            35                  40                  45

Thr Ala Leu Gln Gln Gly Phe Ser Ala Ser Gln Gly Gly Ala Phe Asn
        50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Thr Thr Ile Asn Glu Tyr Thr Gln Arg Val Met Lys Val Phe Lys
            260                 265                 270

Asp Ser Lys Asn Met Pro Thr Ile Gly Thr Asn Lys Phe Ser Val Asp
        275                 280                 285
```

```
Ala Tyr Asn Val Tyr Val Lys Gly Met Thr Leu Asn Val Leu Asp Met
    290                 295                 300

Val Ala Ile Trp Ser Ser Leu Tyr Pro Asn Asp Tyr Thr Ser Gln Thr
305                 310                 315                 320

Ala Ile Glu Gln Thr Arg Val Thr Phe Ser Asn Met Val Gly Gln Glu
                325                 330                 335

Glu Gly Thr Asp Gly Thr Leu Lys Ile Tyr Asn Thr Phe Asp Ser Leu
            340                 345                 350

Ser Tyr Gln His Ser Leu Ile Pro Asn Asn Asn Val Asn Leu Ile Ser
        355                 360                 365

Tyr Tyr Thr Asp Glu Leu Gln Asn Leu Glu Leu Ala Val Tyr Thr Pro
370                 375                 380

Lys Gly Ser Gly Tyr Ala Tyr Pro Tyr Gly Phe Ile Leu Asn Tyr
385                 390                 395                 400

Ala Asn Ser Asn Tyr Lys Tyr Gly Asp Asn Asp Pro Thr Gly Lys Pro
                405                 410                 415

Leu Asn Lys Gln Asp Gly Pro Ile Gln Gln Ile Asn Ala Ala Thr Gln
            420                 425                 430

Asn Ser Lys Tyr Leu Asp Gly Glu Thr Ile Asn Gly Ile Gly Ala Ser
        435                 440                 445

Leu Pro Gly Tyr Cys Thr Thr Gly Cys Ser Ala Thr Glu Gln Pro Phe
450                 455                 460

Ser Cys Thr Ser Thr Ala Asn Ser Tyr Lys Ala Ser Cys Asn Pro Ser
465                 470                 475                 480

Asp Thr Asn Gln Lys Ile Asn Ala Leu Tyr Ala Phe Thr Gln Thr Asn
                485                 490                 495

Val Lys Gly Ser Thr Gly Lys Leu Gly Val Leu Ala Ser Leu Val Pro
            500                 505                 510

Tyr Asp Leu Asn Pro Lys Asn Val Phe Gly Glu Leu Asp Ser Asp Thr
        515                 520                 525

Asn Asn Val Ile Leu Lys Gly Ile Pro Ala Glu Lys Gly Tyr Phe Pro
530                 535                 540

Asn Asn Ala Arg Pro Thr Val Val Lys Glu Trp Ile Asn Gly Ala Ser
545                 550                 555                 560

Ala Val Pro Phe Tyr Ser Gly Asn Thr Leu Phe Met Thr Ala Thr Asn
                565                 570                 575

Leu Thr Ala Thr Gln Tyr Lys Ile Arg Ile Arg Tyr Ala Asn Pro Asn
            580                 585                 590

Ser Asp Thr Gln Ile Gly Val Leu Ile Thr Gln Asn Gly Ser Gln Ile
        595                 600                 605

Ser Asn Ser Asn Leu Thr Leu Tyr Ser Thr Thr Asp Ser Ser Met Ser
610                 615                 620

Ser Asn Leu Pro Gln Asn Val Tyr Val Thr Gly Glu Asn Gly Asn Tyr
625                 630                 635                 640

Thr Leu Leu Asp Leu Tyr Ser Thr Thr Asn Val Leu Ser Thr Gly Asp
                645                 650                 655

Ile Thr Leu Lys Leu Thr Gly Gly Asn Gln Lys Ile Phe Ile Asp Arg
            660                 665                 670

Ile Glu Phe Ile Pro Thr Met Pro Val Pro Ala Pro Thr Asn Asn Thr
        675                 680                 685

Asn Asn Asn Asn Gly Asp Asn Gly Asn Asn Asn Pro Pro His His Gly
690                 695                 700
```

-continued

Cys Ala Ile Ala Gly Thr Gln Gln Leu Cys Ser Gly Pro Pro Lys Phe
705                 710                 715                 720

Glu Gln Val Ser Asp Leu Glu Lys Ile Thr Thr Gln Val Tyr Met Leu
            725                 730                 735

Phe Lys Ser Ser Ser Tyr Glu Glu Leu Ala Leu Lys Val Ser Ser Tyr
        740                 745                 750

Gln Ile Asn Gln Val Ala Leu Lys Val Met Ala Leu Ser Asp Glu Lys
    755                 760                 765

Phe Cys Glu Glu Lys Arg Leu Arg Lys Leu Val Asn Lys Ala Asn
770                 775                 780

Gln Leu Leu Glu Ala Arg Asn Leu Leu Val Gly Gly Asn Phe Glu Thr
785                 790                 795                 800

Thr Gln Asn Trp Val Leu Gly Thr Asn Ala Tyr Ile Asn Tyr Asp Ser
            805                 810                 815

Phe Leu Phe Asn Gly Asn Tyr Leu Ser Leu Gln Pro Ala Ser Gly Phe
        820                 825                 830

Phe Thr Ser Tyr Ala Tyr Gln Lys Ile Asp Glu Ser Thr Leu Lys Pro
    835                 840                 845

Tyr Thr Arg Tyr Lys Val Ser Gly Phe Ile Gly Gln Ser Asn Gln Val
850                 855                 860

Glu Leu Ile Ile Ser Arg Tyr Gly Lys Glu Ile Asp Lys Ile Leu Asn
865                 870                 875                 880

Val Pro Tyr Ala Gly Pro Leu Pro Ile Thr Ala Asp Ala Ser Ile Thr
            885                 890                 895

Cys Cys Ala Pro Glu Ile Asp Gln Cys Asp Gly Gly Gln Ser Asp Ser
        900                 905                 910

His Phe Phe Asn Tyr Ser Ile Asp Val Gly Ala Leu His Pro Glu Leu
    915                 920                 925

Asn Pro Gly Ile Glu Ile Gly Leu Lys Ile Val Gln Ser Asn Gly Tyr
930                 935                 940

Ile Thr Ile Ser Asn Leu Glu Ile Ile Glu Glu Arg Pro Leu Thr Glu
945                 950                 955                 960

Met Glu Ile Gln Ala Val Asn Arg Lys Asp Gln Lys Trp Lys Arg Glu
            965                 970                 975

Lys Leu Leu Glu Cys Ala Ser Val Ser Glu Leu Leu Gln Pro Ile Ile
        980                 985                 990

Asn Gln Ile Asp Ser Leu Phe Lys Asp Ala Asn Trp Tyr Asn Asp Ile
    995                 1000                1005

Leu Pro His Val Thr Tyr Gln Thr Leu Lys Asn Ile Ile Val Pro
    1010                1015                1020

Asp Leu Pro Lys Leu Lys His Trp Phe Ile Asp His Leu Pro Gly
    1025                1030                1035

Glu Tyr His Glu Ile Glu Gln Lys Met Lys Glu Ala Leu Lys His
    1040                1045                1050

Ala Phe Thr Gln Leu Asp Glu Lys Asn Leu Ile His Asn Gly His
    1055                1060                1065

Phe Ala Thr Asn Leu Ile Asp Trp Gln Val Glu Gly Asp Ala Arg
    1070                1075                1080

Met Lys Val Leu Glu Asn Asn Ala Leu Ala Leu Gln Leu Ser Asn
    1085                1090                1095

Trp Asp Ser Ser Val Ser Gln Ser Ile Asp Ile Leu Glu Phe Asp
    1100                1105                1110

Glu Asp Lys Ala Tyr Lys Leu Arg Val Tyr Ala Gln Gly Ser Gly

-continued

```
                 1115                1120                1125

Thr Ile Gln Phe Gly Asn Cys Glu Asp Glu Ala Ile Gln Phe Asn
                 1130                1135                1140

Thr Asn Ser Phe Val Tyr Lys Glu Lys Ile Ile Tyr Phe Asp Thr
                 1145                1150                1155

Pro Ser Ile Asn Leu His Ile Gln Ser Glu Gly Ser Glu Phe Val
                 1160                1165                1170

Val Ser Ser Ile Asp Leu Val Glu Leu Ser Asp Asp Glu
                 1175                1180                1185

<210> SEQ ID NO 4
<211> LENGTH: 1167
<212> TYPE: PRT
<213> ORGANISM: Bacillus thuringiensis
<220> FEATURE:
<223> OTHER INFORMATION: pesticidal crystal

<400> SEQUENCE: 4

Met Thr Asn Pro Thr Ile Leu Tyr Pro Ser Tyr His Asn Val Leu Ala
1               5                   10                  15

His Pro Ile Arg Leu Asp Ser Phe Phe Asp Pro Phe Val Glu Thr Phe
                20                  25                  30

Lys Asp Leu Lys Gly Ala Trp Glu Glu Phe Gly Lys Thr Gly Tyr Met
            35                  40                  45

Asp Pro Leu Lys Gln His Leu Gln Ile Ala Trp Asp Thr Ser Gln Asn
        50                  55                  60

Gly Thr Val Asp Tyr Leu Ala Leu Thr Lys Ala Ser Ile Ser Leu Ile
65                  70                  75                  80

Gly Leu Ile Pro Gly Ala Asp Ala Val Val Pro Phe Ile Asn Met Phe
                85                  90                  95

Val Asp Phe Ile Phe Pro Lys Leu Phe Gly Arg Gly Ser Gln Gln Asn
                100                 105                 110

Ala Gln Ala Gln Phe Phe Glu Leu Ile Ile Glu Lys Val Lys Glu Leu
            115                 120                 125

Val Asp Glu Asp Phe Arg Asn Phe Thr Leu Asn Asn Leu Leu Asn Tyr
        130                 135                 140

Leu Asp Gly Met Gln Thr Ala Leu Ser His Phe Gln Asn Asp Val Gln
145                 150                 155                 160

Ile Ala Ile Cys Gln Gly Glu Gln Pro Gly Leu Met Leu Asp Gln Thr
                165                 170                 175

Pro Thr Ala Cys Thr Pro Thr Thr Asp His Leu Ile Ser Val Arg Glu
                180                 185                 190

Ser Phe Lys Asp Ala Arg Thr Thr Ile Glu Thr Ala Leu Pro His Phe
            195                 200                 205

Lys Asn Pro Met Leu Ser Thr Asn Asp Asn Thr Pro Asp Phe Asn Ser
        210                 215                 220

Asp Thr Val Leu Leu Thr Leu Pro Met Tyr Thr Thr Gly Ala Thr Leu
225                 230                 235                 240

Asn Leu Ile Leu His Gln Gly Tyr Ile Gln Phe Ala Glu Arg Trp Lys
                245                 250                 255

Ser Val Asn Tyr Asp Glu Ser Phe Ile Asn Gln Thr Lys Val Asp Leu
                260                 265                 270

Gln Arg Arg Ile Gln Asp Tyr Ser Thr Thr Val Ser Thr Thr Phe Glu
            275                 280                 285

Lys Phe Lys Pro Thr Leu Asn Pro Ser Asn Lys Glu Ser Val Asn Lys
```

-continued

```
            290                 295                 300
Tyr Asn Arg Tyr Val Arg Ser Met Thr Leu Gln Ser Leu Asp Ile Ala
305                 310                 315                 320

Ala Thr Trp Pro Thr Leu Asp Asn Val Asn Tyr Pro Ser Asn Val Asp
                325                 330                 335

Ile Gln Leu Asp Gln Thr Arg Leu Val Phe Ser Asp Val Ala Gly Pro
                340                 345                 350

Trp Glu Gly Asn Asp Asn Ile Thr Ser Asn Ile Ile Asp Val Leu Thr
            355                 360                 365

Pro Ile Asn Thr Gly Ile Gly Phe Gln Glu Ser Ser Asp Leu Arg Lys
370                 375                 380

Phe Thr Tyr Pro Arg Ile Glu Leu Gln Ser Met Gln Phe His Gly Gln
385                 390                 395                 400

Tyr Val Asn Ser Lys Ser Val Glu His Cys Tyr Ser Asp Gly Leu Lys
                405                 410                 415

Leu Asn Tyr Lys Asn Lys Thr Ile Thr Ala Gly Val Ser Asn Ile Asp
                420                 425                 430

Glu Ser Asn Gln Asn Asn Lys His Asn Tyr Gly Pro Val Ile Asn Ser
            435                 440                 445

Pro Ile Thr Asp Ile Asn Val Asn Ser Gln Asn Ser Gln Tyr Leu Asp
450                 455                 460

Leu Asn Ser Val Met Val Asn Gly Gly Gln Lys Val Thr Gly Cys Ser
465                 470                 475                 480

Pro Leu Ser Ser Asn Gly Asn Ser Asn Ala Ala Leu Pro Asn Gln
                485                 490                 495

Lys Ile Asn Val Ile Tyr Ser Val Gln Ser Asn Asp Lys Pro Glu Lys
                500                 505                 510

His Ala Asp Thr Tyr Arg Lys Trp Gly Tyr Met Ser Ser His Ile Pro
            515                 520                 525

Tyr Asp Leu Val Pro Glu Asn Val Ile Gly Asp Ile Asp Pro Asp Thr
530                 535                 540

Lys Gln Pro Ser Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
                565                 570                 575

Val Lys Leu Thr Ser Tyr Gln Val Leu Gln Met Glu Val Thr Asn Gln
                580                 585                 590

Thr Thr Gln Lys Tyr Arg Ile Arg Ile Arg Tyr Ala Thr Gly Gly Asp
            595                 600                 605

Thr Ala Ala Ser Ile Trp Phe His Ile Ile Gly Pro Ser Gly Asn Asp
610                 615                 620

Leu Thr Asn Glu Gly His Asn Phe Ser Ser Val Ser Ser Arg Asn Lys
625                 630                 635                 640

Met Phe Val Gln Gly Asn Asn Gly Lys Tyr Val Leu Asn Ile Leu Thr
                645                 650                 655

Asp Ser Ile Glu Leu Pro Ser Gly Gln Gln Thr Ile Leu Ile Gln Asn
                660                 665                 670

Thr Asn Ser Gln Asp Leu Phe Leu Asp Arg Ile Glu Phe Ile Ser Leu
            675                 680                 685

Pro Ser Thr Ser Thr Pro Thr Ser Thr Asn Phe Val Glu Pro Glu Ser
690                 695                 700

Leu Glu Lys Ile Ile Asn Gln Val Asn Gln Leu Phe Ser Ser Ser
705                 710                 715                 720
```

```
Gln Thr Glu Leu Ala His Thr Val Ser Asp Tyr Lys Ile Asp Gln Val
            725                 730                 735

Val Leu Lys Val Asn Ala Leu Ser Asp Asp Val Phe Gly Val Glu Lys
            740                 745                 750

Lys Ala Leu Arg Lys Leu Val Asn Gln Ala Lys Gln Leu Ser Lys Ala
            755                 760                 765

Arg Asn Val Leu Val Gly Gly Asn Phe Glu Lys Gly His Glu Trp Ala
            770                 775                 780

Leu Ser Arg Glu Ala Thr Met Val Ala Asn His Glu Leu Phe Lys Gly
785                 790                 795                 800

Asp His Leu Leu Leu Pro Pro Thr Leu Tyr Pro Ser Tyr Ala Tyr
            805                 810                 815

Gln Lys Ile Asp Glu Ser Lys Leu Lys Ser Asn Thr Arg Tyr Thr Val
            820                 825                 830

Ser Gly Phe Ile Ala Gln Ser Glu His Leu Glu Val Val Ser Arg
            835                 840                 845

Tyr Gly Lys Glu Val His Asp Met Leu Asp Ile Pro Tyr Glu Glu Ala
            850                 855                 860

Leu Pro Ile Ser Ser Asp Glu Ser Pro Asn Cys Cys Lys Pro Ala Ala
865                 870                 875                 880

Cys Gln Cys Ser Ser Cys Asp Gly Ser Gln Ser Asp Ser His Phe Phe
            885                 890                 895

Ser Tyr Ser Ile Asp Val Gly Ser Leu Gln Ser Asp Val Asn Leu Gly
            900                 905                 910

Ile Glu Phe Gly Leu Arg Ile Ala Lys Pro Asn Gly Phe Ala Lys Ile
            915                 920                 925

Ser Asn Leu Glu Ile Lys Glu Asp Arg Pro Leu Thr Glu Lys Glu Ile
            930                 935                 940

Lys Lys Val Gln Arg Lys Glu Gln Lys Trp Lys Lys Ala Phe Asn Gln
945                 950                 955                 960

Glu Gln Ala Glu Val Ala Thr Thr Leu Gln Pro Thr Leu Asp Gln Ile
            965                 970                 975

Asn Ala Leu Tyr Gln Asn Glu Asp Trp Asn Gly Ser Val His Pro Ala
            980                 985                 990

Ser Asp Tyr Gln His Leu Ser Ala Val Val Val Pro Thr Leu Pro Lys
            995                 1000                1005

Gln Arg His Trp Phe Met Glu Gly Arg Glu Gly Glu His Val Val
            1010                1015                1020

Leu Thr Gln Gln Phe Gln Gln Ala Leu Asp Arg Ala Phe Gln Gln
            1025                1030                1035

Ile Glu Glu Gln Asn Leu Ile His Asn Gly Asn Leu Ala Asn Gly
            1040                1045                1050

Leu Thr Asp Trp Thr Val Thr Gly Asp Ala Gln Leu Thr Ile Phe
            1055                1060                1065

Asp Glu Asp Pro Val Leu Glu Leu Ala His Trp Asp Ala Ser Ile
            1070                1075                1080

Ser Gln Thr Ile Glu Ile Met Asp Phe Glu Gly Arg His Arg Ile
            1085                1090                1095

Gln Thr Ala Cys Thr Trp Lys Arg Gln Arg Asn Ser Tyr Arg Ser
            1100                1105                1110

Thr Trp Arg Lys Arg Leu Glu Thr Met Thr Phe Asn Thr Thr Ser
            1115                1120                1125
```

Phe Thr Thr Gln Glu Gln Thr Phe Tyr Phe Glu Gly Asp Thr Val
    1130                1135                1140

Asp Val His Val Gln Ser Glu Asn Asn Thr Phe Leu Ile Asp Ser
    1145                1150                1155

Val Glu Leu Ile Glu Ile Ile Glu Glu
    1160                1165

<210> SEQ ID NO 5
<211> LENGTH: 1167
<212> TYPE: PRT
<213> ORGANISM: Bacillus thuringiensis
<220> FEATURE:
<223> OTHER INFORMATION: pesticidal crystal

<400> SEQUENCE: 5

Met Thr Asn Pro Thr Ile Leu Tyr Pro Ser Tyr His Asn Val Leu Ala
1               5                   10                  15

His Pro Ile Arg Leu Asp Ser Phe Phe Asp Pro Phe Val Glu Thr Phe
            20                  25                  30

Lys Asp Leu Lys Gly Ala Trp Glu Glu Phe Gly Lys Thr Gly Tyr Met
        35                  40                  45

Asp Pro Leu Lys Gln His Leu Gln Ile Ala Trp Asp Thr Ser Gln Asn
50                  55                  60

Gly Thr Val Asp Tyr Leu Ala Leu Thr Lys Ala Ser Ile Ser Leu Ile
65                  70                  75                  80

Gly Leu Ile Pro Gly Ala Asp Ala Val Val Pro Phe Ile Asn Met Phe
                85                  90                  95

Val Asp Phe Ile Phe Pro Lys Leu Phe Gly Arg Gly Ser Gln Gln Asn
            100                 105                 110

Ala Gln Ala Gln Phe Phe Glu Leu Ile Ile Glu Lys Val Lys Glu Leu
        115                 120                 125

Val Asp Glu Asp Phe Arg Asn Phe Thr Leu Asn Asn Leu Leu Asn Tyr
130                 135                 140

Leu Asp Gly Met Gln Thr Ala Leu Ser His Phe Gln Asn Asp Val Gln
145                 150                 155                 160

Ile Ala Ile Cys Gln Gly Glu Gln Pro Gly Leu Met Leu Asp Gln Thr
                165                 170                 175

Pro Thr Ala Cys Thr Pro Thr Thr Asp His Leu Ile Ser Val Arg Glu
            180                 185                 190

Ser Phe Lys Asp Ala Arg Thr Thr Ile Glu Thr Ala Leu Pro His Phe
        195                 200                 205

Lys Asn Pro Met Leu Ser Thr Asn Asp Asn Thr Pro Asp Phe Asn Ser
210                 215                 220

Asp Thr Val Leu Leu Thr Leu Pro Met Tyr Thr Thr Ala Ala Thr Leu
225                 230                 235                 240

Asn Leu Ile Leu His Gln Gly Tyr Ile Gln Phe Ala Glu Arg Trp Lys
                245                 250                 255

Ser Val Asn Tyr Asp Glu Ser Phe Ile Asn Gln Thr Lys Val Asp Leu
            260                 265                 270

Gln Arg Arg Ile Gln Asp Tyr Ser Thr Thr Val Ser Thr Thr Phe Glu
        275                 280                 285

Lys Phe Lys Pro Thr Leu Asn Pro Ser Asn Lys Glu Ser Val Asn Lys
290                 295                 300

Tyr Asn Arg Tyr Val Arg Ser Met Thr Leu Gln Ser Leu Asp Ile Ala
305                 310                 315                 320

```
Ala Thr Trp Pro Thr Leu Asp Asn Val Asn Tyr Pro Ser Asn Val Asp
            325                 330                 335

Ile Gln Leu Asp Gln Thr Arg Leu Val Phe Ser Asp Val Ala Gly Pro
        340                 345                 350

Trp Glu Gly Asn Asp Asn Ile Thr Ser Asn Ile Ile Asp Val Leu Thr
    355                 360                 365

Pro Ile Asn Thr Gly Ile Gly Phe Gln Glu Ser Ser Asp Leu Arg Lys
370                 375                 380

Phe Thr Tyr Pro Arg Ile Glu Leu Gln Ser Met Gln Phe His Gly Gln
385                 390                 395                 400

Tyr Val Asn Ser Lys Ser Val Glu His Cys Tyr Ser Asp Gly Leu Lys
            405                 410                 415

Leu Asn Tyr Lys Asn Lys Thr Ile Thr Ala Gly Val Ser Asn Ile Asp
        420                 425                 430

Glu Ser Asn Gln Asn Asn Lys His Asn Tyr Gly Pro Val Ile Asn Ser
    435                 440                 445

Pro Ile Thr Asp Ile Asn Val Asn Ser Gln Asn Ser Gln Tyr Leu Asp
450                 455                 460

Leu Asn Ser Val Met Val Asn Gly Gly Gln Lys Val Ala Gly Cys Ser
465                 470                 475                 480

Pro Leu Ser Ser Asn Gly Asn Ser Asn Ala Ala Leu Pro Asn Gln
            485                 490                 495

Lys Ile Asn Val Ile Tyr Ser Val Gln Ser Asn Asp Lys Pro Glu Lys
        500                 505                 510

His Ala Asp Thr Tyr Arg Lys Trp Gly Tyr Met Ser Ser His Ile Pro
    515                 520                 525

Tyr Asp Leu Val Pro Glu Asn Val Ile Gly Asp Ile Asp Pro Asp Thr
530                 535                 540

Lys Gln Pro Ser Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
            565                 570                 575

Val Lys Leu Thr Ser Tyr Gln Val Leu Lys Met Glu Val Thr Asn Gln
        580                 585                 590

Thr Thr Gln Lys Tyr Arg Ile Arg Ile Arg Tyr Ala Thr Gly Gly Asp
    595                 600                 605

Thr Ala Ala Ser Ile Trp Phe His Ile Ile Gly Pro Ser Gly Asn Asp
610                 615                 620

Leu Thr Asn Glu Gly His Asn Phe Ser Ser Val Ser Ser Arg Asn Lys
625                 630                 635                 640

Met Phe Val Gln Gly Asn Asn Gly Lys Tyr Val Leu Asn Ile Leu Thr
            645                 650                 655

Asp Ser Ile Glu Leu Pro Ser Gly Gln Gln Thr Ile Leu Ile Gln Asn
        660                 665                 670

Thr Asn Ser Gln Asp Leu Phe Leu Asp Arg Ile Glu Phe Ile Ser Leu
    675                 680                 685

Pro Ser Thr Ser Thr Pro Thr Ser Thr Asn Phe Val Glu Pro Glu Ser
690                 695                 700

Leu Glu Lys Ile Ile Asn Gln Val Asn Gln Leu Phe Ser Ser Ser Ser
705                 710                 715                 720

Gln Thr Glu Leu Ala His Thr Val Ser Asp Tyr Lys Ile Asp Gln Val
            725                 730                 735

Val Leu Lys Val Asn Ala Leu Ser Asp Asp Val Phe Gly Val Glu Lys
```

-continued

```
            740                 745                 750
Lys Ala Leu Arg Lys Leu Val Asn Gln Ala Lys Gln Leu Ser Lys Ala
            755                 760                 765
Arg Asn Val Leu Val Gly Gly Asn Phe Glu Lys Gly His Glu Trp Ala
        770                 775                 780
Leu Ser Arg Glu Ala Thr Met Val Ala Asn His Glu Leu Phe Lys Gly
785                 790                 795                 800
Asp His Leu Leu Leu Pro Pro Pro Thr Leu Tyr Pro Ser Tyr Ala Tyr
                805                 810                 815
Gln Lys Ile Asp Glu Ser Lys Leu Lys Ser Asn Thr Arg Tyr Thr Val
            820                 825                 830
Ser Gly Phe Ile Ala Gln Ser Glu His Leu Glu Val Val Ser Arg
            835                 840             845
Tyr Gly Lys Glu Val His Asp Met Leu Asp Ile Pro Tyr Glu Ala
        850                 855             860
Leu Pro Ile Ser Ser Asp Glu Ser Pro Asn Cys Cys Lys Pro Ala Ala
865                 870                 875                 880
Cys Gln Cys Ser Ser Cys Asp Gly Ser Gln Ser Asp Ser His Phe Phe
                885                 890                 895
Ser Tyr Ser Ile Asp Val Gly Ser Leu Gln Ser Asp Val Asn Leu Gly
            900                 905                 910
Ile Glu Phe Gly Leu Arg Ile Ala Lys Pro Asn Gly Phe Ala Lys Ile
        915                 920                 925
Ser Asn Leu Glu Ile Lys Glu Asp Arg Pro Leu Thr Glu Lys Glu Ile
    930                 935                 940
Lys Lys Val Gln Arg Lys Glu Gln Lys Trp Lys Lys Ala Phe Asn Gln
945                 950                 955                 960
Glu Gln Ala Glu Val Ala Thr Thr Leu Gln Pro Thr Leu Asp Gln Ile
                965                 970                 975
Asn Ala Leu Tyr Gln Asn Glu Asp Trp Asn Gly Ser Val His Pro His
            980                 985                 990
Val Thr Tyr Gln His Leu Ser Ala  Val Val Pro Thr  Leu Pro Lys
        995                 1000                1005
Gln Arg  His Trp Phe Met Glu  Asp Arg Glu Gly Glu  His Val Val
    1010                1015                1020
Leu Thr  Gln Gln Phe Gln Gln  Ala Leu Asp Arg Ala  Phe Gln Gln
    1025                1030                1035
Ile Glu  Glu Gln Asn Leu Ile  His Asn Gly Asn Phe  Ala Asn Gly
    1040                1045                1050
Leu Thr  Asp Trp Thr Val Thr  Gly Asp Ala Gln Leu  Thr Ile Phe
    1055                1060                1065
Asp Glu  Asp Pro Val Leu Glu  Leu Ala His Trp Asp  Ala Ser Ile
    1070                1075                1080
Ser Gln  Thr Ile Glu Ile Met  Asp Phe Glu Glu Asp  Thr Glu Tyr
    1085                1090                1095
Lys Leu  Arg Val Arg Gly Lys  Gly Lys Gly Thr Val  Thr Val Gln
    1100                1105                1110
His Gly  Glu Glu Glu Leu Glu  Thr Met Thr Phe Asn  Thr Thr Ser
    1115                1120                1125
Phe Thr  Thr Gln Glu Gln Thr  Phe Tyr Phe Glu Gly  Asp Thr Val
    1130                1135                1140
Asp Val  His Val Gln Ser Glu  Asn Asn Thr Phe Leu  Ile Asp Ser
    1145                1150                1155
```

Val Glu Leu Ile Glu Ile Ile Glu Glu
    1160            1165

<210> SEQ ID NO 6
<211> LENGTH: 475
<212> TYPE: PRT
<213> ORGANISM: Bacillus thuringiensis
<220> FEATURE:
<223> OTHER INFORMATION: pesticidal crystal

<400> SEQUENCE: 6

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

```
Ser Asp Asp Ala Asp Glu Ile Gln Ile Glu Leu Glu Asp Ala Ser Asp
        355                 360                 365
Ala Trp Leu Val Val Ala Gln Glu Ala Arg Asp Phe Thr Leu Asn Ala
    370                 375                 380
Tyr Ser Thr Asn Ser Arg Gln Asn Leu Pro Ile Asn Val Ile Ser Asp
385                 390                 395                 400
Ser Cys Asn Cys Ser Thr Thr Asn Met Thr Ser Asn Gln Tyr Ser Asn
                405                 410                 415
Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460
Asp Trp Tyr Asn Asn Ser Asp Trp Tyr Asn Asn
465                 470                 475

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry1A

<400> SEQUENCE: 7

Val Tyr Ile Asp Arg Ile Glu Phe Val Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry3A

<400> SEQUENCE: 8

Val Tyr Ile Asp Lys Ile Glu Phe Ile Pro
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry4A

<400> SEQUENCE: 9

Val Leu Ile Asp Lys Ile Glu Phe Leu Pro
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry5A

<400> SEQUENCE: 10

Val Phe Leu Asp Arg Ile Glu Phe Ile Pro
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry5B

<400> SEQUENCE: 11

Leu Phe Leu Asp Arg Ile Glu Phe Val Pro
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry7A

<400> SEQUENCE: 12

Phe Tyr Val Asp Ser Ile Glu Phe Ile Pro
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry8A

<400> SEQUENCE: 13

Val Tyr Ile Asp Arg Ile Glu Phe Ile Pro
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry9A

<400> SEQUENCE: 14

Val Tyr Val Asp Arg Ile Glu Phe Ile Pro
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry10A

<400> SEQUENCE: 15

Ile Tyr Ile Asp Lys Ile Glu Phe Ile Pro
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic Block 5 Conserved Group for protein Cry12A

<400> SEQUENCE: 16

Met Val Leu Asp Arg Ile Glu Phe Val Pro
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry13A

<400> SEQUENCE: 17

Ile Tyr Leu Asp Arg Leu Glu Phe Val Pro
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry14A

<400> SEQUENCE: 18

Ile Phe Ile Asp Arg Ile Glu Phe Ile Pro
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry19A

<400> SEQUENCE: 19

Leu Ile Leu Asp Lys Ile Glu Phe Leu Pro
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry20A

<400> SEQUENCE: 20

Phe Val Leu Asp Lys Ile Glu Leu Ile Pro
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      Block 5 Conserved Group for protein Cry21A

<400> SEQUENCE: 21

Leu Phe Leu Asp Arg Ile Glu Phe Ile Ser
1               5                   10

<210> SEQ ID NO 22

```
<211> LENGTH: 10
<212> TYPE: PRT
<213> ORGANISM: Artificial Sequence
<220> FEATURE:
<223> OTHER INFORMATION: Description of Artificial Sequence: Synthetic
      Consensus sequence
<220> FEATURE:
<221> NAME/KEY: MOD_RES
<222> LOCATION: (2)..(2)
<223> OTHER INFORMATION: Any amino acid

<400> SEQUENCE: 22

Ile Xaa Ile Asp Lys Ile Glu Phe Ile Pro
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide motif

<400> SEQUENCE: 23

Asp Arg Ile Glu Phe
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide motif

<400> SEQUENCE: 24

Asp Arg Leu Glu Phe
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      original signal peptidase cleavage site

<400> SEQUENCE: 25

Asp Thr Asn Ser Asp
1               5

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 26
cgttcaaaat catccgtaaa tg                                            22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer
```

```
<400> SEQUENCE: 27
aaatgcatga accacttcca c                                              21

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 28
tggcaacaat taatgagttg tatccag                                        27

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 29
ctgccttgac aaatggctac t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 30
caccccaggc tttacacttt a                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 31
aggcgattaa gttgggtaac g                                              21

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 32

His His His His His His His His His His
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Met Gly Gly Gly Phe Ala
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Asn Leu Tyr Phe Gln
1               5
```